(12) United States Patent
Carder et al.

(10) Patent No.: US 10,975,404 B2
(45) Date of Patent: Apr. 13, 2021

(54) METHOD AND COMPOSITION COMPRISING HYDROLYZED STARCH

(71) Applicant: The Quaker Oats Company, Chicago, IL (US)

(72) Inventors: Gary Carder, Barrington Hills, IL (US); Robert E. Chatel, Hoffman Estates, IL (US); Yongsoo Chung, Palatine, IL (US); Justin A. French, Frisco, TX (US); Wesley Twombly, Fox River Grove, IL (US)

(73) Assignee: The Quaker Oats Company, Chicago, IL (US)

( * ) Notice: Subject to any disclaimer, the term of this patent is extended or adjusted under 35 U.S.C. 154(b) by 0 days.

(21) Appl. No.: 15/930,631

(22) Filed: May 13, 2020

(65) Prior Publication Data

US 2020/0270661 A1    Aug. 27, 2020

Related U.S. Application Data

(60) Division of application No. 15/077,758, filed on Mar. 22, 2016, now Pat. No. 10,689,678, which is a continuation-in-part of application No. 14/959,941, filed on Dec. 4, 2015, application No. 15/930,631, which is a continuation-in-part of application No. 14/959,941, which is a continuation-in-part of application No. 14/209,075, filed on Mar. 13, 2014, now Pat. No. 9,622,500, which is a continuation-in-part of application No. 14/209,000, filed on Mar. 13, 2014, now Pat. No. 9,510,614, application No. 15/930,631, which is a continuation-in-part of application No. 14/209,075, application No. 15/930,631, which is a continuation-in-part of application No. 14/059,566, filed on Oct. 22, 2013, now Pat. No. 9,149,060, and a continuation-in-part of application No. 14/059,566, which is a continuation of application No. 12/666,509, filed as application No. PCT/US2009/060016 on Oct. 8, 2009, now Pat. No. 8,591,970, which is a continuation-in-part of application No. 12/264,399, filed on Nov. 4, 2008, now Pat. No. 8,574,644.

(60) Provisional application No. 61/783,046, filed on Mar. 14, 2013.

(51) Int. Cl.
| | |
|---|---|
| *C12P 19/14* | (2006.01) |
| *C12P 19/02* | (2006.01) |
| *A23L 29/30* | (2016.01) |
| *C13K 1/06* | (2006.01) |
| *A23L 2/52* | (2006.01) |

(52) U.S. Cl.
CPC ............... *C12P 19/14* (2013.01); *A23L 2/52* (2013.01); *A23L 29/35* (2016.08); *C12P 19/02* (2013.01); *C13K 1/06* (2013.01)

(58) Field of Classification Search
CPC ........... C12P 19/14; C12P 19/04; C12P 19/02; A23L 29/35; C13K 1/06
USPC ........................................................ 426/598
See application file for complete search history.

(56) References Cited

U.S. PATENT DOCUMENTS

| | | |
|---|---|---|
| 1,163,175 A | 12/1915 | Rullman |
| 1,384,894 A | 7/1921 | Horlick |
| 3,116,150 A | 12/1963 | Baker |
| 3,317,402 A | 5/1967 | Smith et al. |
| 3,391,003 A | 7/1968 | Armstrong |
| 3,494,769 A | 2/1970 | Tressler |
| 3,579,352 A | 5/1971 | Bookwalter |
| 3,595,671 A | 7/1971 | Cooke |
| 3,732,109 A | 5/1973 | Poat |
| 3,753,728 A | 8/1973 | Bedenk |
| 3,851,085 A | 11/1974 | Rodgers et al. |
| 3,869,558 A | 3/1975 | Hampton et al. |
| 3,925,343 A | 12/1975 | Hampton et al. |
| 3,950,543 A | 4/1976 | Buffa et al. |
| 3,958,016 A | 5/1976 | Galle et al. |

(Continued)

FOREIGN PATENT DOCUMENTS

| | | |
|---|---|---|
| AU | 1989045913 | 5/1989 |
| CA | 1045890 | 1/1979 |

(Continued)

OTHER PUBLICATIONS

U.S. Appl. No. 15/077,758, filed Mar. 22, 2016.
U.S. Appl. No. 14/959,941, filed Dec. 4, 2015.
U.S. Appl. NO. 14/209,000, filed Mar. 13, 2014.
U.S. Appl. No. 14/059,566, filed Oct. 22, 2013.

(Continued)

*Primary Examiner* — Hamid R Badr
(74) *Attorney, Agent, or Firm* — Barnes & Thornburg LLP; G. Peter Nichols

(57) ABSTRACT

A method and composition comprising hydrolyzed starch. In a first aspect, the method comprises several steps. A first step comprises combining at least a portion of pulse and a suitable enzyme to form an enzyme-pulse starting mixture. The enzyme-pulse starting mixture comprises starch. A second step comprises heating the enzyme-pulse starting mixture to between about 48.89° C. and about 93.33° C. to begin to hydrolyze the starch, thereby providing a heated pulse mixture. A third step comprises extruding the heated pulse mixture to continue hydrolyzing the starch and further to gelatinize and cook the heated pulse mixture thereby providing a pulse product comprising gelatinized, hydrolyzed starch. In a second aspect, the invention provides a composition comprising at least a portion of pulse, and the at least a portion of pulse comprises gelatinized, hydrolyzed starch.

20 Claims, 10 Drawing Sheets

(56) References Cited

U.S. PATENT DOCUMENTS

| | | | |
|---|---|---|---|
| 4,028,468 A | 6/1977 | Hohner | |
| 4,038,427 A | 7/1977 | Martin | |
| 4,167,584 A | 9/1979 | Nelson | |
| 4,171,384 A | 10/1979 | Chwalek et al. | |
| 4,233,322 A * | 11/1980 | Fritze | A23L 11/05 426/46 |
| 4,247,561 A | 1/1981 | Nelson | |
| 4,259,358 A | 3/1981 | Duthie | |
| 4,266,027 A | 5/1981 | Muller et al. | |
| 4,282,319 A | 8/1981 | Conrad | |
| 4,330,625 A | 5/1982 | Miller et al. | |
| 4,377,602 A | 3/1983 | Conrad | |
| 4,431,674 A | 2/1984 | Fulger et al. | |
| 4,435,429 A | 3/1984 | Burrows et al. | |
| 4,435,430 A | 3/1984 | Fulger et al. | |
| 4,438,150 A | 3/1984 | Gantwerker | |
| 4,439,460 A | 3/1984 | Tsau et al. | |
| 4,500,558 A | 2/1985 | Fulger | |
| 4,551,347 A | 11/1985 | Karwowski | |
| 4,613,507 A | 9/1986 | Fulger et al. | |
| 4,656,040 A | 4/1987 | Fulger et al. | |
| 4,668,519 A | 5/1987 | Dartey | |
| 4,692,340 A | 9/1987 | Grutte | |
| 4,710,386 A | 12/1987 | Fulger et al. | |
| 4,777,056 A | 10/1988 | Buhler et al. | |
| 4,834,988 A | 5/1989 | Karwowski et al. | |
| 4,834,989 A | 5/1989 | Bolles et al. | |
| 4,886,665 A | 12/1989 | Kovacs | |
| 4,957,563 A | 9/1990 | Gallaher | |
| 4,996,063 A | 2/1991 | Inglett | |
| 4,999,208 A | 3/1991 | Lengerich et al. | |
| 4,999,298 A | 3/1991 | Wolfe | |
| 5,021,248 A | 6/1991 | Stark et al. | |
| 5,045,328 A | 9/1991 | Lewis | |
| 5,082,673 A | 1/1992 | Inglett | |
| 5,106,343 A | 4/1992 | Laufer | |
| 5,106,634 A | 4/1992 | Thacker | |
| 5,145,698 A | 9/1992 | Cajigas | |
| 5,225,219 A | 7/1993 | Inglett | |
| 5,234,704 A | 8/1993 | Devine | |
| 5,320,856 A | 6/1994 | Veronesi | |
| 5,334,407 A | 8/1994 | Donnelly | |
| 5,385,746 A | 1/1995 | De Almeida | |
| 5,395,623 A | 3/1995 | Kovach | |
| 5,407,694 A | 4/1995 | Devine | |
| 5,458,893 A | 10/1995 | Smith | |
| 5,476,675 A | 12/1995 | Lou | |
| 5,490,997 A | 2/1996 | Devine | |
| 5,523,109 A | 6/1996 | Hellweg | |
| 5,554,402 A | 9/1996 | Smith | |
| 5,571,334 A | 11/1996 | Dunn et al. | |
| 5,656,317 A | 8/1997 | Smits et al. | |
| 5,686,123 A | 11/1997 | Lindahl | |
| 5,744,187 A | 4/1998 | Gaynor | |
| 5,846,786 A | 12/1998 | Senkeleski et al. | |
| 5,849,090 A | 12/1998 | Haralampu et al. | |
| 5,863,590 A | 1/1999 | Alan | |
| 5,888,548 A | 3/1999 | Wongsuragrai et al. | |
| 5,912,031 A | 6/1999 | Fitchett | |
| 5,932,264 A | 8/1999 | Hurd | |
| 5,981,237 A | 11/1999 | Meagher | |
| 5,985,339 A | 11/1999 | Kamarei | |
| 5,997,917 A | 12/1999 | Uchida et al. | |
| 6,013,289 A | 1/2000 | Blank et al. | |
| 6,054,302 A | 4/2000 | Shi et al. | |
| 6,135,015 A | 10/2000 | Mendez | |
| 6,168,821 B1 | 1/2001 | Castleberry | |
| 6,190,708 B1 | 2/2001 | Triantafyllou | |
| 6,210,722 B1 | 4/2001 | Wullschleger et al. | |
| 6,210,738 B1 | 4/2001 | Chen | |
| 6,210,741 B1 | 4/2001 | Van Lengerich | |
| 6,224,106 B1 | 4/2001 | Meschonat | |
| 6,244,528 B1 | 6/2001 | Wallis et al. | |
| 6,287,621 B1 | 9/2001 | Lacourse et al. | |
| 6,287,626 B1 | 9/2001 | Fox | |
| 6,395,314 B1 | 5/2002 | Whalen | |
| 6,451,369 B1 | 9/2002 | Triantafyllou | |
| 6,482,459 B1 | 11/2002 | Anderson | |
| 6,551,366 B1 | 4/2003 | D'Souza et al. | |
| 6,592,914 B1 | 7/2003 | Triantafyllou | |
| 6,610,349 B1 | 8/2003 | Delrue et al. | |
| 6,617,446 B1 | 9/2003 | Papadopoulos | |
| 6,685,974 B2 | 2/2004 | Whalen | |
| 6,720,022 B1 | 4/2004 | Amaut et al. | |
| 6,723,358 B1 | 4/2004 | Van Lengerich | |
| 6,759,077 B1 | 7/2004 | Lewis et al. | |
| 6,797,307 B2 | 9/2004 | Malkki et al. | |
| 7,030,092 B1 | 4/2006 | Levine | |
| 7,160,564 B2 | 1/2007 | Oste | |
| 7,244,457 B2 | 7/2007 | Racicot | |
| 7,419,694 B2 | 9/2008 | Korolchuk | |
| 7,425,344 B2 | 9/2008 | Korolchuk et al. | |
| 7,754,270 B2 | 7/2010 | Wuersch et al. | |
| 7,794,774 B2 | 9/2010 | Foster | |
| 7,914,972 B2 | 3/2011 | Fujiwara | |
| 8,241,696 B2 | 8/2012 | Chung | |
| 8,518,469 B2 | 8/2013 | Macdonald | |
| 8,574,644 B2 | 11/2013 | Chatel | |
| 8,591,970 B2 | 11/2013 | Chatel | |
| 8,742,095 B2 | 6/2014 | Lehtomaki | |
| 9,011,947 B2 | 4/2015 | Carder | |
| 9,149,060 B2 | 10/2015 | Chatel | |
| 9,150,895 B2 | 10/2015 | Kurihara | |
| 2001/0002269 A1 | 5/2001 | Zhao | |
| 2001/0022986 A1 | 9/2001 | Girsh | |
| 2002/0127319 A1 | 9/2002 | Gare | |
| 2002/0187224 A1 | 12/2002 | Haefliger et al. | |
| 2003/0170362 A1 | 9/2003 | Manning et al. | |
| 2004/0028797 A1 | 2/2004 | Squire et al. | |
| 2004/0101935 A1 | 5/2004 | Vasanthan | |
| 2004/0140584 A1 | 7/2004 | Wang et al. | |
| 2004/0151805 A1 | 8/2004 | Gao et al. | |
| 2004/0156971 A1 | 8/2004 | Wuersch et al. | |
| 2004/0258829 A1 | 12/2004 | Zheng et al. | |
| 2005/0064080 A1 | 3/2005 | Creighton et al. | |
| 2005/0089602 A1 | 4/2005 | Kvist et al. | |
| 2005/0106216 A1 | 5/2005 | Maurer et al. | |
| 2005/0181114 A1 | 8/2005 | Bruemmer | |
| 2005/0191400 A1 | 9/2005 | Satyavolu et al. | |
| 2005/0214347 A1 | 9/2005 | Astrup et al. | |
| 2005/0238777 A1 | 10/2005 | Klingberg et al. | |
| 2005/0244563 A1 | 11/2005 | Cavalieri et al. | |
| 2005/0260305 A1 | 11/2005 | Adele et al. | |
| 2006/0008574 A1 | 1/2006 | Begli et al. | |
| 2006/0013940 A1 | 1/2006 | Mueller et al. | |
| 2006/0093720 A1 | 5/2006 | Tatz | |
| 2006/0115573 A1 | 6/2006 | Singer et al. | |
| 2006/0121174 A1 | 6/2006 | Franke | |
| 2006/0134299 A1 | 6/2006 | Lahteenmaki | |
| 2006/0141097 A1 | 6/2006 | Guo | |
| 2006/0240148 A1 | 10/2006 | Nguyen et al. | |
| 2006/0251791 A1 | 11/2006 | Rubio et al. | |
| 2006/0257548 A1 | 11/2006 | Crofskey | |
| 2006/0280838 A1 | 12/2006 | Kvist et al. | |
| 2006/0286269 A1 | 12/2006 | Shah et al. | |
| 2007/0014892 A1 | 1/2007 | Mitchell et al. | |
| 2007/0026105 A1 | 2/2007 | Seo | |
| 2007/0059340 A1 | 3/2007 | Bello et al. | |
| 2001/0104854 | 5/2007 | Foster | |
| 2007/0104854 A1 | 5/2007 | Foster et al. | |
| 2007/0141218 A1 | 6/2007 | Chatel | |
| 2007/0154609 A1 | 7/2007 | Li | |
| 2007/0172568 A1 | 7/2007 | Spelman | |
| 2007/0178199 A1 | 8/2007 | Minor et al. | |
| 2007/0184175 A1 | 8/2007 | Rubio et al. | |
| 2007/0212472 A1 | 9/2007 | Holenstein et al. | |
| 2007/0243301 A1 | 10/2007 | Barnett et al. | |
| 2007/0264400 A1 | 11/2007 | Milne | |
| 2007/0292583 A1 | 12/2007 | Haynes et al. | |
| 2008/0003340 A1 | 1/2008 | Karwowski et al. | |
| 2008/0008801 A1 | 1/2008 | Barnekow et al. | |
| 2008/0131582 A1 | 6/2008 | Karwowski et al. | |
| 2008/0171114 A1 | 7/2008 | Castillo Rodriguez et al. | |
| 2008/0260909 A1 | 10/2008 | Chung et al. | |

(56) References Cited

U.S. PATENT DOCUMENTS

| | | |
|---|---|---|
| 2008/0305212 A1 | 12/2008 | Wong |
| 2009/0053771 A1 | 2/2009 | Dale et al. |
| 2009/0148562 A1 | 6/2009 | Lin et al. |
| 2009/0181128 A1 | 7/2009 | Blumenthal et al. |
| 2009/0238935 A1 | 9/2009 | Haynes et al. |
| 2009/0311376 A1 | 12/2009 | Rao et al. |
| 2010/0015306 A1 | 1/2010 | Pereyra |
| 2010/0104718 A1 | 4/2010 | Durand |
| 2010/0112167 A1 | 5/2010 | Chatel |
| 2010/0316765 A1 | 12/2010 | French et al. |
| 2010/0330230 A1 | 12/2010 | Strozzi |
| 2011/0020523 A1 | 1/2011 | Pereyra et al. |
| 2012/0082740 A1 | 4/2012 | Collins et al. |
| 2012/0245111 A1 | 9/2012 | Hoebler |
| 2013/0017300 A1 | 1/2013 | Avila et al. |
| 2013/0183405 A1 | 7/2013 | Chatel et al. |
| 2013/0209610 A1 | 8/2013 | Carder et al. |
| 2013/0170362 A1 | 9/2013 | Manning |
| 2013/0323799 A1 | 12/2013 | Takaha |
| 2014/0017356 A1 | 1/2014 | Te Biesebeke |
| 2014/0050819 A1 | 2/2014 | Chatel |
| 2014/0193563 A1 | 7/2014 | Carder |
| 2014/0193564 A1 | 7/2014 | Carder |
| 2015/0183821 A1 | 7/2015 | Konstantinov |
| 2015/0191758 A1 | 7/2015 | Larsen |
| 2015/0351432 A1 | 12/2015 | Triantafyllou |
| 2016/0106125 A1 | 4/2016 | Rascon |
| 2016/0185641 A1 | 6/2016 | Zuback |

FOREIGN PATENT DOCUMENTS

| | | | |
|---|---|---|---|
| CA | 2015149 | 10/1990 | |
| CN | 1386446 | 12/2002 | |
| CN | 1499940 | 5/2004 | |
| DE | 970141 | 8/1958 | |
| EP | 0078782 | 5/1983 | |
| EP | 0231729 | 8/1987 | |
| EP | 0512249 | 11/1992 | |
| EP | 0897673 | 2/1994 | |
| EP | 0609169 | 8/1994 | |
| EP | 0634106 | 1/1995 | |
| EP | 0474230 | 3/1995 | |
| EP | 0806434 | 11/1997 | |
| EP | 1208752 A1 * | 5/2002 | ..... C12Y 302/01001 |
| EP | 1782699 | 5/2007 | |
| EP | 2205101 | 7/2010 | |
| FR | 2620906 | 3/1989 | |
| GB | 1168692 | 10/1969 | |
| JP | 63116657 | 5/1988 | |
| JP | 2000004852 | 1/2000 | |
| JP | 2002171920 | 6/2002 | |
| JP | 2005523331 | 8/2005 | |
| RU | 2237419 | 10/2001 | |
| TW | 58246 | 5/1984 | |
| WO | WO 9210106 | 6/1992 | |
| WO | WO 1993000826 | 1/1993 | |
| WO | WO 9604799 | 2/1996 | |
| WO | WO 2000030457 | 6/2000 | |
| WO | WO 02076244 | 10/2002 | |
| WO | WO 2003011052 | 2/2003 | |
| WO | WO 2003090557 | 11/2003 | |
| WO | WO 2004086878 | 10/2004 | |
| WO | WO 0609169 | 1/2006 | |
| WO | WO 2006009169 | 1/2006 | |
| WO | WO 2007020059 | 2/2007 | |
| WO | WO 2008028994 | 3/2008 | |
| WO | WO 2008096044 | 8/2008 | |
| WO | WO 2009077659 | 6/2009 | |
| WO | WO 2009109703 | 9/2009 | |
| WO | WO 2009127687 | 10/2009 | |
| WO | WO 2009158588 | 12/2009 | |
| WO | WO 2010108277 | 9/2010 | |
| WO | WO 2014160351 | 10/2014 | |

OTHER PUBLICATIONS

U.S. Appl. No. 12/666,509, filed Apr. 25, 2011.
U.S. Appl. No. 12/264,399, filed Nov. 4, 2008.
U.S. Appl. No. 14/209,075, filed Mar. 13, 2014.
Camire, Mary Ellen, et al. "Thermal Processing Effects on Dietary Fiber Composition and Hydration Capacity in Corn Meal, Oat Meal, and Potato Peels," Cereal Chemistry 68(6), pp. 645-647, vol. 68, No. 6, 1991 (3 pages).
Singh, Narpinder, et al., "A Composition of Wheat Starch, Whole Wheat Meal and Oat Flour in the Extrusion Cooking Process," J. Food Engineering 34 (1997) 15-32 (18 pages).
Tapola, N., et al. "Glycemic responses of oat brain products in type 2 diabetic patients," Nutrition, Metabolism & Cardiovascular Diseases (2005) 15, 255, 261 (7pages).
Vasanthan, et al. "Dietary fiber profile of barley flour as affected by extrusion cooking," Food Chemistry 77 (2002) pp. 35-40 (6 pages).
Hoseney, R. Carl, "Principles of Cereal Science and Technology," 1986, American Association of Cereal Chemists, Inc., St. Paul Minnesota 55121, pp. 148-149 (4 pages).
Grenus, Food Product Design, Applications, Agglomerations, Jul. 10, 2014, Weeks Publishing Co., pp. 1-4, www.foodproductdesign.com/articles/2004/07/food-design-applications.
PCT Application No. PCT/US2008/060323 International Search Report and Written Opinion dated Aug. 13, 2008.
PCT Application No. PCT/US2009/059916 International Search Report and Written Opinion dated Feb. 16, 2010.
PCT Application No. PCT/US2014/21913 International Search Report and Written Opinion dated Jun. 23, 2014.
Likimani, T.A., "Extrusion Cooking of Corn/Soybean Mix in Presense of Thermostable a-Amylase," Journal of Food Science, vol. 56, No. 1, 1991, pp. 99-105 (7 pages).
Davis, "The Effect of Cold on Micro-Organisms in Relation to Dairying," Express Dairy Co (London), Proceedings of the Society for Applied Bacteriology, vol. 14, Issue 2, pp. 216-242, Oct. 1951.
Food Reference, About.com "Why Does Milk Curdle," http://foodreference.about.com/od/Dairy/a/Why-Does-Milk-Curdle.htm, pp. 1-2.
PCT Application No. PCT/US2012/046450 International Search Report and Written Opinion dated Sep. 6, 2012.
Springer New York, "Milk and Milk Products," Essentials of Food Science, Food Science Texts Series, pp. 237-269.
Anderson, et al. "Gelatinazation of corn grits by roll cooking, extrusion cooking and steaming," Starche 22: 130-135.
Brenda, The comprehensive Enzyme Information System, BC 3.2.1.1.—alpha amylase; pp. 1 to 297; Retrieved from the internet: http://www.brenda-enzymes.info/php/result_flat.php4?ecno=3.2.1.1&organism_list= date unknown.
The Whole Grains Council, "What are the Health Benefits?," http://wholegrainscouncil.org/whole-grains-101/what-are-the-health-benefits, 2 page.
International Search Report and Written Opinion for PCT/US2014/26367 dated Sep. 9, 2014.
International Search Report and Written Opinion for PCT/US2014/17288 dated Jun. 13, 2014.
Chinese Patent Application 200880025660.8 Office Action dated Aug. 2, 2012.
Wang Changquing et al., Study on the Extruding Production Method of Soluble Oats Fiber, vol. 28, No. 2, pp. 45-48, dated Mar. 20, 2002, with English Abstract.
Vasanthan, V. et al., "Dextrinization of Starch in Barley Flours with Thermostable Alpha-Amylase by Extrusion Cooking," Starke-Starch, Wiley-VCH Verlag, Weinheim, DE, XP001110714, ISSN: 0038-9056, vol. 53, No. 12, pp. 616-622, dated Dec. 1, 2001 (Abstract Only).
Gutkoski, L.C., et al., "Effect of Extrusion Process Variables on Physical and Chemical Properties of Extruded Oat Products," Plant Foods for Human Nutrition, © 2000 Kluwer Academic Publishers, pp. 315-325, dated Dec. 31, 1999.
Inglett, G.E. et al. 1994. Oat beta-glucan-amylodextrin: Preliminary preparations and biological properties. Plant Fd. for Human Nutrition. 45: 53-61.
Linko Y Y et al., the effect of HTST-extrusion on retention of cereal alpha-amylase activity and on enzymatic hydrolisis of barley starch,

(56) References Cited

OTHER PUBLICATIONS

Food Processing Systems, Applied Science Publ, UK, Jan. 1, 1980 (Jan. 1, 1980), pp. Abstr, 4.2.25, 210-223, XP009127925, ISBN: 978-0-85334-896-2.

Peter Koelln KGAA: "Kochjule, Hafer-Getrank mit Fruchtsaft," XP002499645, Internet Citation, URL:http://www.koelln.de/downloads/37/Kochjule.pdf>, retrieved from the Internet on Oct. 14, 2008, pp. 1-19, dated Oct. 14, 2008, copy unavailable.

Peter Kolln KGAA: "KollnFlocken Instant," XP002499437, Internet Citation, URL:http://www.koelln.de/produkte/1/15/index.html>, retrieved from the Internet on Oct. 13, 2008, p. 1 dated Oct. 13, 2008.

Written Opinion and International Search Report for PCT Application No. PCT/US2010/038506 dated Aug. 10, 2010, 18 pages.

Zhang Haodong, "Starch Article Technology," Jilin Science and Technology Press, dated Feb. 29, 2008—copy unavailable.

Australian Patent Application No. 2010260219 Office Action dated Aug. 23, 2012.

Chinese Patent Application No. 201080022395.5 Office Action dated Nov. 8, 2012.

Canadian Patent Application No. 2761566 Office Action dated Dec. 27, 2012.

Russian Patent Application No. 2011145771 Office Action dated Jan. 21, 2013.

European Patent Application 09740225.9 Office Action dated May 16, 2011.

European Patent Application 09740225.9 Office Action dated Oct. 11, 2010.

Chinese Patent Application No. 200880025660.8, Office Action dated Apr. 11, 2013.

Russian Application No. 2011145771 Office Action dated Apr. 14, 2013.

Chinese Patent Application No. 200880025660.8 Office Action dated Oct. 10, 2013.

European Application No. 12188138.7 Office Action dated Nov. 13, 2013.

Mexican Application No. MX/a/2010/000255 Office Action dated Aug. 29, 2013.

Malaysian Application No. PI20095590 Office Action dated Apr. 15, 2014.

Australian Application No. 2009251225 Office Action dated Mar. 28, 2014.

Anonymous: "Ovsena nahradka mlieka," XP002561727, URL: http://web.archive.org/web/20080420075151/http://www.aspsk.sk/ovsene_mlieko.htm>, retrieved from the Internet on Dec. 18, 2009, pp. 1-1, dated Apr. 20, 2008.

Gualberto, D.G. et al., Effect of extrusion processing on the soluble and insoluble fiber, and phytic acid contents of cereal brans, dated Sep. 28, 1997.

PCT/US2009/060016, International Search Report, dated Feb. 8, 2010.

Peter Kolln KGAA: "Kolln Schmelzflocken Dinkel-Hafer," XP002499438, Internet Citation, URL:http://www.koelln.de/produkte/2/103/index.html>, retrieved from the Internet on Oct. 13, 2008, p. 1, dated Oct. 13, 2008.

Wang, Ming-chun, et al, Extrusion Technology Applied in the Nutritional Health Foods, College of Food Engineering & Biologic Technology, Tianjin University of Science and Technology, Tianjin 300457, pp. 63-66, dated Aug. 1, 2007, with English Abstract.

Anonymous: "Goldkill Instant Barley Drink," XP002561728, URL:http://web.archive.org/web/20060303003347/goldkill.com/goldkili_instant.php, retrieved from the Internet on Dec. 28, 2009, pp. 1-2, dated Mar. 3, 2006.

EP Application 14195125.1-1358, Extended Search Report, dated Jan. 29, 2015.

EP Application 14195095.6-1358 / 2842430, European Search Report, dated Jan. 23, 2015.

EP Application 14195129.3, European Search Report, dated Jan. 26, 2015.

EP Application 14195114.5, Extended European Search Report, dated Jan. 23, 2015.

EP Patent No. EP2205101 (Formerly Application No. EP09740225.9), Notice of Opposition to a European Patent dated Jul. 10, 2013.

Japanese Patent Application 2012-108270, Office Action dated Feb. 4, 2014 (with English Translation).

PCT/US2009/060016, International Preliminary Report on Patentability, dated May 19, 2011.

Office Action, U.S. Appl. No. 12/264,399, dated Jun. 5, 2012.

\* cited by examiner

METHOD AND COMPOSITION COMPRISING HYDROLYZED STARCH

CROSS-REFERENCE TO RELATED APPLICATIONS

This application is a divisional application of U.S. Nonprovisional patent application Ser. No. 15/077,758 filed Mar. 22, 2016, which is a continuation-in-part of U.S. Nonprovisional patent application Ser. No. 14/209,000, now U.S. Pat. No. 9,510,614, which is a continuation-in-part of U.S. Nonprovisional patent application Ser. No. 14/059,566 filed on Oct. 22, 2013, now U.S. Pat. No. 9,149,060, which is a continuation of U.S. Nonprovisional patent application Ser. No. 12/666,509, filed on Apr. 25, 2011, now U.S. Pat. No. 8,591,970, filed as Patent Application No. PCT/US2009/060016 on Oct. 8, 2009, which is a continuation-in-part of U.S. Nonprovisional patent application Ser. No. 12/264,399, filed on Nov. 4, 2008, now U.S. Pat. No. 8,574,644; additionally, this application is a continuation-in-part of U.S. Nonprovisional patent application Ser. No. 14/209,075, now U.S. Pat. No. 9,622,500, which is a continuation-in-part of U.S. Nonprovisional patent application Ser. No. 14/059,566, filed on Oct. 22, 2013, now U.S. Pat. No. 9,149,060, which is a continuation of U.S. Nonprovisional patent application Ser. No. 12/666,509, filed on Apr. 25, 2011, now U.S. Pat. No. 8,591,970, filed as Patent Application No. PCT/US2009/060016 on Oct. 8, 2009, which is a continuation-in-part of U.S. Nonprovisional patent application Ser. No. 12/264,399, filed on Nov. 4, 2008, now U.S. Pat. No. 8,574,644; additionally, U.S. Nonprovisional patent application Ser. No. 14/209,000 is a nonprovisional application of, and claims priority to, U.S. Provisional Patent Application No. 61/783,046 filed on Mar. 14, 2013; additionally, U.S. Nonprovisional patent application Ser. No. 14/209,075 is a nonprovisional application of, and claims priority to, U.S. Provisional Patent Application No. 61/783,046 filed on Mar. 14, 2013; additionally, this application is a divisional application of U.S. Nonprovisional patent application Ser. No. 15/077,758 filed Mar. 22, 2016, which is a continuation-in-part of U.S. Nonprovisional patent application Ser. No. 14/959,941, filed on Dec. 4, 2015, which is a continuation-in-part of U.S. Nonprovisional patent application Ser. No. 14/209,000 and Ser. No. 14/209,075, which applications further claim priority as indicated; additionally, this application claims priority to all of the above-referenced patent applications and incorporates all the above-referenced patent applications by reference in their entirety.

FIELD OF THE INVENTION

The present invention relates generally, for example, to food grade compositions comprising a hydrolyzed starch. As a further illustration, the invention relates to a composition comprising at least a portion of a grain and/or at least a portion of a pulse with hydrolyzed starch. For example, the present invention relates to pulse flour, grain flour, oat flour, barley flour, or bran flour (e.g., oat bran flour). The invention also relates to soluble grains, pulses, and/or at least a portion thereof. For example, the invention relates to food products prepared with pulse or whole grain having soluble components (hereinafter "soluble grain flour"). As another example, the present invention relates to food products prepared with whole oat flour having soluble components (hereinafter "soluble oat flour") or whole barley flour having soluble components (hereinafter "soluble barley flour"). As another illustration, the present invention relates to methods of making compositions comprising at least a portion of a grain and/or at least a portion of a pulse with hydrolyzed starch. For example, the present invention relates to methods of making soluble oat or barley flour.

BACKGROUND OF THE INVENTION

Products comprising at least a portion of a grain and/or at least a portion of a pulse can be desirable for nutritive and/or fiber content. However, these products can also have undesirable mouthfeel characteristics for some consumers. For example, such products can be too viscous, gritty, or result in a thick coating on the mouth upon consumption. Furthermore, products comprising grain and/or pulse that have better mouthfeel can be modified in a way that lacks certain nutritive or fiber-related components or benefits that would otherwise be present.

BRIEF SUMMARY OF THE INVENTION

In a first aspect, the invention provides a method comprising several steps. A first step comprises combining at least a portion of pulse and a suitable enzyme to form an enzyme-pulse starting mixture. The enzyme-pulse starting mixture comprises starch. A second step comprises heating the enzyme-pulse starting mixture to between about 48.89° C. and about 93.33° C. to begin to hydrolyze the starch, thereby providing a heated pulse mixture. A third step comprises extruding the heated pulse mixture to continue hydrolyzing the starch and further to gelatinize and cook the heated pulse mixture thereby providing a pulse product comprising gelatinized, hydrolyzed starch.

In a second aspect, the invention provides a composition comprising at least a portion of pulse, and the at least a portion of pulse comprises gelatinized, hydrolyzed starch.

These and other aspects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations. Every component of each embodiment of the invention is not shown where illustration is not necessary to allow those of ordinary skill in the art to understand the invention.

DETAILED DESCRIPTION OF THE INVENTION

Figure 1:
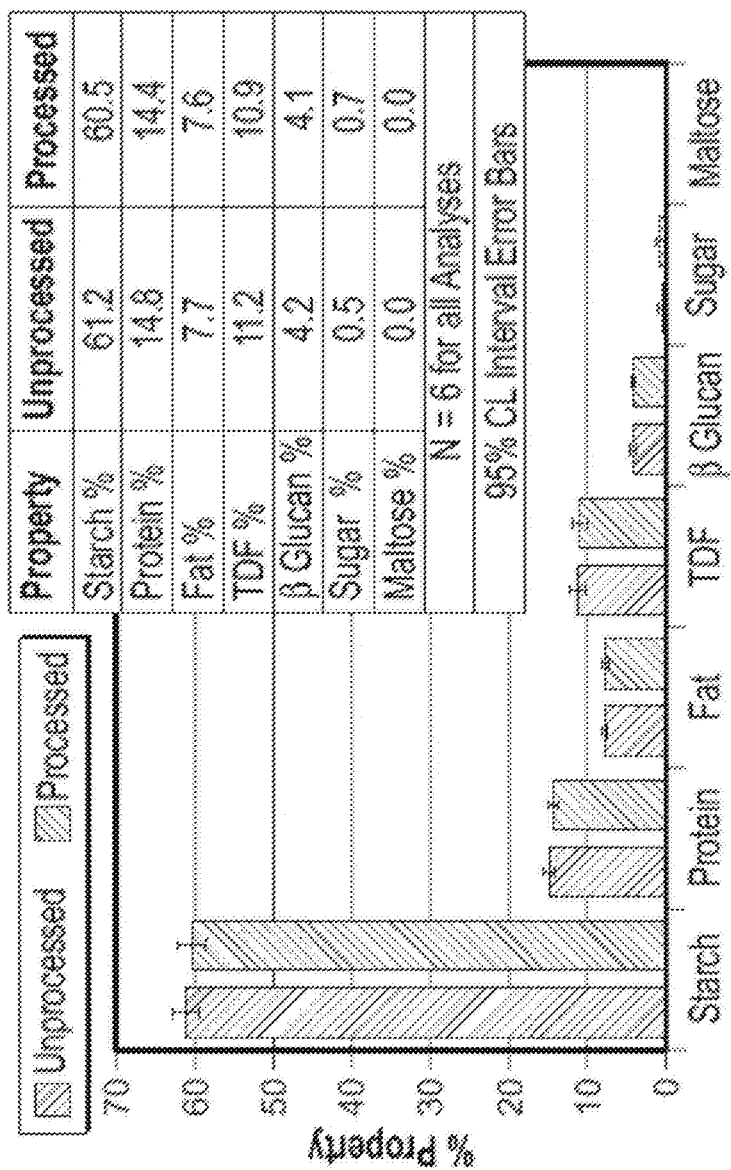
FIG. 1 depicts a proximate composition of unprocessed and processed whole oat flour.

Oatmeal has for many years been a staple of the human diet due to its health benefits. For example, numerous studies have shown that eating oatmeal on a daily basis can help lower blood cholesterol, reduce risk of heart disease, promote healthy blood flows as well as maintain healthy blood pressure levels. Additionally, oatmeal has a high content of complex carbohydrates and fibers, which facilitates slow digestion and stable blood-glucose levels.

With today's hectic lifestyle, consumers are demanding convenience, such as portability and ease of preparation. Consumers desire oatmeal from a variety of food sources including beverages and convenience foods such as bars, cookies, crackers, smoothies, shakes (e.g., breakfast shakes), and the like.

For example, it can be desirable to prepare a whole oat product that has sufficient soluble fiber to meet the FDA threshold necessary to justify a health claim. For example, a whole oat or barley product must have 0.75 g soluble beta-glucan fiber per serving of food to support a health claim under 21 C.F.R. 101.81, which is incorporated herein by reference as an example. To prepare an oat beverage that contains at least 0.75 g soluble oat fiber per serving (about 18 g of whole grain oats), it can be beneficial to use highly dispersible oat flour that also retains its whole grain standard (e.g., highly soluble whole grain oat flour). "Studies show that eating whole grains instead of refined grains lowers the risk of many chronic diseases. While benefits are most pronounced for those consuming at least 3 servings daily, some studies show reduced risks from as little as one serving daily." http://wholegrainscouncil.org/whole-grains-101/what-are-the-health-benefits. Note that 1 full serving of whole grain is 16 g.

The inventors have determined that it would be useful to produce different types of food products that are made with certain components and/or characteristics, for example, healthier components or components have suitable and/or desirable characteristics for consumers or manufacturers. As an example, it can be desirable to produce whole grain (e.g., whole oat or barley) flour that is highly dispersible in liquid, semisolid, or solid media, and maintains its standard of identity as whole grain.

In some embodiments, aspects of the invention relate to food products containing highly dispersible, soluble whole oat flour. The soluble whole oat flour maintains its standard of identity as whole grain and thus has the characteristics of whole grain oats.

In some embodiments, aspects of the present invention relate to the use of the soluble oat flour in various food products including liquid food products such as beverages, semi-solid food products such as yogurt, and solid food products such as bakery items in order to provide enhanced health benefits.

In some embodiments, the present invention relates to products comprising grains and pulses with hydrolyzed starch. For example, in some embodiments, the invention provides a soluble whole grain flour. As an illustration, the soluble whole grain flour can be prepared using an extruder or other suitable continuous cooker. In some embodiments, the process is easier, less expensive, and less time-consuming than prior art processes. An example of a process for preparing a grain flour comprising hydrolyzed starch (e.g., soluble oat or barley flour) is found in U.S. patent application Ser. No. 12/264,399 filed Nov. 4, 2008 and issued as U.S. Pat. No. 8,574,644 on Nov. 5, 2013, the contents of which is expressly incorporated herein by reference in its entirety as an example. In one embodiment, a method of producing soluble oat or barley flour comprises using a pre-conditioner and an extruder or other suitable continuous cooker.

In some embodiments, the soluble whole oat flour (or other whole grain) made in accordance with the methods described herein maintains its standard of identity as whole grain throughout processing (e.g., starch hydrolysis, pelletizing, drying, and/or grinding). "Whole grain" or "standard of identity as whole grain" shall mean that the cereal grain, for example, oat, "consists of the intact, ground cracked or flaked caryopsis, whose principal anatomical components—the starchy endosperm, germ and bran—are present in approximately the same relative proportions as they exist in the intact caryopsis." (See, AACC International's Definition of "Whole Grains," approved in 1999, available at http://www.aaccnet.org/initiatives/definitions/pages/wholegrain.aspx (last accessed Feb. 11, 2016).) Further, if the principal nutrients (i.e., starch, fat, protein, dietary fiber, beta-glucan, and sugar) are present in approximately the same relative proportions for a partially hydrolyzed grain and the original grain, it can be assumed that the processed grain (e.g., the partially hydrolyzed grain) maintains its whole grain status. However, since the average molecular weight of starch (e.g., amylopectin) in whole grains varies widely across the various types of whole grains (e.g., 1-400 million Dalton) and even among whole grain oat products, a shift in starch moieties from higher molecular weight to lower molecular weight does not alter whole grain status if the total starch content remains the same.

As shown, for example, in FIG. 1, the processed oat flour made in accordance with the instant disclosure maintains substantially the same levels of starch, protein, fat, total dietary fiber (TDF), glucan, sugar and maltose as the unprocessed oat flour when considered in terms of relative mass ratios of the components to starch. As used herein a mass ratio of X (e.g., starch) to Y (e.g., protein) in a composition (e.g., whole grain) is equal to the mass of X in the composition divided by the mass of Y in the composition. For example, in one embodiment illustrated in FIG. 1, the processed oat flour made in accordance with the instant disclosure experiences a change in the mass ratio of protein to starch of about −0.0038, a change in the mass ratio of fat to starch of about −0.0002, a change in the mass ratio of TDF to starch of about −0.0028, a change in the mass ratio of beta-glucan to starch of about −0.009, a change in the mass ratio of sugar to starch of about 0.0034, and no measurable change in the mass ratio of maltose to starch. Furthermore, in one embodiment the processed oat flour made in accordance with the instant disclosure experiences a relative change in the mass ratio of protein to starch of about −0.016, a relative change in the mass ratio of fat to starch of about −0.002, a relative change in the mass ratio of TDF to starch of about −0.016, a relative change in the mass ratio of beta-glucan to starch of about −0.013, a relative change in the mass ratio of sugar to starch of about 0.416, and no measurable relative change in the mass ratio of maltose to starch. As can be seen, the absolute change in the mass ratio is the better indicator of whether whole grain status is maintained because components that are initially present in small amounts can have significant relative increases (e.g., sugar or specific sugars such as maltose). However, when considered as a mass ratio of the component to other components at higher mass concentrations, the change is negligible. Put another way, in some embodiments starch is originally present, for example, at around 50 wt. % or more of a composition while sugar is only present at around 1 wt. % or less.

Accordingly, if a small percentage of the original mass of starch is converted to sugar, or if there is a small measurement error, then there can be what appears to be a significant change in the amount of sugar as measured relative to the original amount of sugar, but for practical purposes the absolute change in sugar is negligible (e.g., the total change of a component in wt. % is no more than about 3 wt. % and the change in the absolute mass ratio of the component to starch is no more than about 0.03). This is so because the total content of the principal nutrients can naturally vary among crops for an unprocessed grain. As a result, a certain degree of tolerance, as illustrated above, can be allowed in determining that the principal nutrients are present in the same relative proportions for a partially hydrolyzed grain and the original grain. In some embodiments, the degree of tolerance is equivalent to the naturally occurring variance in the mass ratios of the principal nutrients to starch in a species or variety of grain. Furthermore, a shift from high molecular weight starch (e.g., amylopectin) to low molecular weight starch (e.g., amylopectin) does not change the total starch content and does not impact whole grain status.

The term "soluble flour" (e.g., "soluble pulse flour," "soluble grain flour," soluble whole grain flour," "soluble bran flour," "soluble oat flour," or "soluble whole grain oat flour") refers to flour that maintains soluble components such as beta-glucan but also is highly dispersible in liquids such as water. The dispersibility of the flour was measured in water observing formation of a lump and size of the lumps on the top and bottom of the water after stirring for five (5) seconds. "Highly dispersible" therefore means that there are no lumps present or formed after stirring the mixture for about 5 seconds. As the skilled artisan would recognize, stirring can also be interchanged with shaking or some other specific movement to incorporate and mix the flour into the liquid.

The term "regular oat flour," "typical oat flour," and "unprocessed oat flour" refers to whole oat flour that is made by conventional or traditional milling methods and not "soluble oat flour" or oat flour made in accordance with the methods described herein, unless otherwise clear from context. For example, a whole oat flour with hydrolyzed starch (e.g., soluble oat flour made using the methods described herein) can still qualify as a whole oat flour. Accordingly, the term "whole oat flour" in isolation can refer to unprocessed whole oat flour or whole oat flour in which starch has been hydrolyzed without converting the starch to monosaccharides and disaccharides. For example, as discussed earlier, the soluble whole oat flour (or other whole grain) made in accordance with the methods described herein can maintain its standard of identity as whole grain throughout processing.

Also, for purposes of illustration, the invention is described with reference to "oat" or "barley" embodiments. However, in some embodiments, an "oat" component or "barley" component is replaced with another component or group of components that comprise starch. For example, in some embodiments, an "oat" component or "barley" component is replaced with at least one component selected from the group consisting of "grains," "one and only one grain," "pulses," "one and only one pulse," "a portion of a grain," "a portion of a pulse," and combinations thereof.

Furthermore, for purposes of illustration, some embodiments are described with reference to soluble flour. Examples of soluble flour include flour made from soluble grain (e.g., wheat, oat, barley, corn, white rice, brown rice, barley, millet, sorghum, rye, triticale, teff, spelt, buckwheat, *quinoa*, amaranth, kaniwa, cockscomb, green groat and combinations thereof) and flour made from soluble pulse (e.g., peas, lentils, chickpeas, navy beans, black turtle beans, cranberry beans, kidney beans, pinto beans, small red beans, Dutch brown beans, pink beans and combinations thereof). When the term soluble flour is used, flours of any of these whole grains, pulses, a portion of any of these grains, a portion of any of these pulses, and/or any combination thereof can be substituted as applicable in context.

With respect to the products of the soluble oat flour made in accordance with the methods disclosed herein, the term "hot beverage" or "hot comestible" shall mean a beverage or comestible that is typically served or consumed between about 55° C. and 85° C. Similarly "cold beverage" or "cold comestible" as used herein shall refer to a beverage or comestible that is typically served or consumed between about 4° C. and 25° C. The skilled food technician would recognize, however, that although the beverages and comestibles are intended to be consumed at the temperature ranges discussed above, the respective beverages and comestibles can be served and consumed at temperatures outside of these ranges based on consumer preference or circumstance.

Initially, enzyme-treated oat or barley flour can be prepared by combining a whole oat or barley flour starting mixture and a suitable enzyme solution in a mixer (e.g., a pre-conditioner) and then heating the mixture. The enzyme-treated mixture is then subjected to an extrusion process to gelatinize, hydrolyze, and cook the oat or barley flour mixture. In some embodiments, a suitable amount of time is provided before extrusion. Then, after a suitable amount of time to begin to break down and hydrolyze the oat or barley flour, the enzyme-treated mixture is subjected to an extrusion process to continue to break down and hydrolyze the oat or barley flour and to gelatinize and cook the mixture.

A suitable starting mixture can be prepared by combining the whole oat or barley flour with other desired ingredients. For example, a typical starting mixture contains whole oat or barley flour and granulated sugar. Maltodextrin and/or at least one antioxidant can also be added.

The whole oat or barley flour can be present in an amount of about 1% to about 100% or about 50% to about 100% by weight of the total weight of the starting composition. In further aspects, the whole oat flour can be present in amounts of about 80% to about 95% by weight or about 90% to about 95% by weight.

The sugar can be any suitable sugar known to those skilled in the art. Non-limiting examples of sugars include sucrose, fructose, dextrose, other sugars known in the art, and combinations thereof. Typically, the sugar is present in an amount of about 0% to about 15%, about 1% to about 15%, or about 3% to about 15% by weight of the total weight of the starting composition. In further aspects, the sugar is present in amounts of about 3% to about 7% by weight.

The maltodextrin can be present in an amount of about 0% to about 15% by weight of the total weight of the starting composition. In further aspects, the maltodextrin is present in amounts of about 3% to about 7% by weight.

The antioxidant can be any suitable antioxidant such as mixed natural tocopherols or artificial antioxidant such as BHT and BHA. The antioxidant can be present in an amount from 0.1% to 2% by weight. In further aspects, the antioxidant can be present in amounts of about 0.25% to about 0.75% by weight.

A suitable, but non-limiting, flour mix formula for extrusion process.

| Ingredient | % |
|---|---|
| Whole oat flour | 89.35 |
| Sugar | 5.00 |
| Maltodextrin | 5.00 |
| Mixed tocopherols | 0.50 |
| α-amylase | 0.15 |
| Total | 100.00 |

The enzyme can be any suitable enzyme to hydrolyze the starch in the oat or barley flour and does not change or adversely affect the beta-glucan that is present in the oat or barley flour. Suitable enzymes include α-amylase in the range of about 0.01-0.5%, for example about 0.1-0.2%. In one aspect of the present disclosure, the a-amylase used can be Validase 1000L having approximately 1,000,000 MWU/g (MWU—Modified Wohlgemuth Unit). Whether the beta-glucan has changed by the hydrolysis can be determined by any suitable method such as by analyzing the structure of the beta-glucan. This can be done by laser light scattering mass spectroscopy. The enzyme can be added to water to form an enzyme water solution. Then the enzyme-water solution can be combined with the starting mixture in the pre-conditioner.

In some embodiments, the starting mixture and enzyme solution is heated to at least about 120° F. (48.89° C.), 140° F. (60° C.), 200° F. (93.33° C.), or 212° F. (100° C.), or between about 120° F. (48.89° C.) and about 200° F. (93.33° C.), for example, between about 140° F. (60° C.) and about 180° F. (82.22° C.), e.g., 165° F. (73.89° C.) for about 3 to 5 minutes to initiate gelatinization of starch. The enzyme then reacts on gelatinized starches to hydrolyze (e.g., break down) some of the starch molecules, for example, the high molecular weight amylopectin starch fractions (e.g., having an average molecular weight of $5.8-6.2\times10^6$ Dalton) into low molecular weight starch molecules, for example, low molecular weight amylopectin starch fractions (e.g., having an average molecular weight of $1.7-2.0\times10^6$ Dalton).

In some embodiments, the starting mixture and enzyme solution can be mixed in any suitable vessel such as a high speed mixer that permits liquid to be added to free-flowing flour. In some embodiments, the suitable vessel is called a preconditioner. The output is a free-flowing wetted flour mixture having a moisture content of about 25 to about 40%. The residence time is the time sufficient to obtain the desired result and typically 1 to 5 min.

The enzyme-treated mixture is subsequently added to an extruder (continuous cooker) to gelatinize, hydrolyze, and cook the starch. The mixture resides in the extruder for a time sufficient to gelatinize and cook the starch, but not long enough to dextrinize or otherwise modify the starch to void the whole grain aspect, generally at least 30 seconds or at least 1 minute, typically, about 30 seconds to about 1.5 minutes or about 1 to about 1.5 minutes, to form a dough. Generally, the material is heated from an initial inlet temperature to a final exit temperature in order to provide the energy for starch gelatinization.

Starch gelatinization requires adequate water and heat. In some embodiments, the gelatinization temperature range for grains (e.g., oats, barley, wheat, etc.) is 127° F. to 160° F. (53-71° C.), or 127° F. to 138° F. (53-59° C.). If the moisture is less than about 60% then higher temperatures are required.

Heat can be applied through the extruder barrel wall such as with a jacket around the barrel through which a hot medium like steam, water or oil is circulated, or electric heaters imbedded in the barrel. Typically the extrusion occurs at barrel temperatures between 140° F. (60° C.) and 350° F. (176.67° C.), for example between 175° F. (79.44° C.) and 340° F. (171.11° C.), about 180° F. (82.22° C.) –300° F. (148.89° C.), or about 270° F. (132.22° C.) to about 310° F. (154.44°), or about 290° F. (143.33° C.). In some embodiments, the extrusion occurs at barrel temperatures between 140° F. (60° C.) and 300° F. (148.89° C.), or between 140° F. (60° C.) and 250° F. (121.11° C.). For example, in one embodiment, the wall temperature of the extruder barrel at the end of the extruder is about 280° F. (137.78° C.) to 300° F. (148.89° C.), or about 290° F. (143.33° C.), which can be useful to ensure that a hydrolysis-catalyzing enzyme is deactivated. Although, after reading this disclosure, a person skilled in the art would recognize that enzymes (e.g., amylases or cellulases) can be deactivated at different temperatures depending on which type of amylase or cellulase is used. Additionally, in some embodiments, the dough temperatures are approximately between 212° F. (100° C.) and 260° F. (126.67° C.).

Heat is also generated within the material by friction as it moves within the extruder by the dissipation of mechanical energy in the extruder, which is equal to the product of the viscosity and the shear rate squared for a Newtonian fluid. Shear is controlled by the design of the extruder screw(s) and the screw speed. Viscosity is a function of starch structure, temperature, moisture content, fat content and shear. The temperature of the dough increases in the extruder to about 212° F. (100° C.) to 350° F. (176.67° C.) or about 212° F. (100° C.) to 300° F. (148.89° C.). Although, in some embodiments, the dough temperatures are approximately between 212° F. (100° C.) and 260° F. (126.67° C.).

Extrusion conditions are chosen to adequately heat the extrudate to the desired temperature at the desired moisture content. Excessive cooked grain flavor can be generated if the combination of time and temperature of the extrudate exceeds some optimum. For some embodiments the moisture content of the extrudate is about 28% to about 33% with a wall temperature after the final barrel section is about 280° F. (137.78° C.) to about 330° F. (165.56° C.) or about 280° F. (137.78° C.) to about 305° F. (151.67° C.). Inadequate water addition for may result in dextrinization of the starch in the extrudate. For example, in one embodiment, low shear is applied to the mixture in the extruder. In some embodiments (e.g., where the enzyme has preconditioned the starch), high shear is not required. Additionally, in some embodiments, high shear makes it difficult to control the degree of hydrolysis. It can also increase the dough temperature excessively, which can overcook it resulting in too much cooked grain flavor. As another example, high shear can dextrinize the starch, which can be undesirable in some embodiments. It is noted that the barrel temperature and the dough temperature can be different.

In some embodiments, the process balances limiting the dough temperature to avoid too much cooked grain flavor and to keep the enzyme active. For example, the process can be balanced such that the dough temperature rises to a sufficient temperature to deactivate the enzyme. Such temperatures are at least 280° F. (137.78° C.), generally 212° F. (100° C.) to about 330° F. (165.56° C.), or about 212° F. (100° C.) to 300° F. (148.89° C.). A low shear extrusion process is characterized relative to high shear extrusion by high moisture and a low shear screw design versus low moisture and a high shear screw design.

Any suitable extruder can be used including suitable single screw or twin screw extruders. Typical, but not limiting, screw speeds are 200-350 rpm (e.g., 200-300 rpm).

The resulting product can be pelletized using a forming extruder and dried, typically to about 1.5 to about 12%, or about 1.5 to about 10%, for example 6.5 to 8.5%, moisture content by weight. The pellets can be granulated to a max 5% through a US 40 screen. The particle size of the resulting granulated product is about 10-500 microns, for instance, about 1-450 microns, more particularly about 30-420 microns. Although, in some embodiments, the pellets are granulated to a max 85% through a US 30 screen.

Jet milling can be used to mill the pellets produced in accordance with aspects of the present disclosure. Jet milling creates ultrafine particles. In particular, jet milling reduces the particle size of the pelletized soluble grain flour (e.g., oat, barley, or wheat flour) to less than about 90 micron, for example, less than about 50 microns, such as about 46 microns. As one of ordinary skill in the art would recognize, alternative milling processes can be used to reduce the particle size or micronize the flour to, 0.5-50 microns, such as between 10 to 50 microns.

The resulting soluble grain flour (e.g., oat flour) includes beta-glucan soluble fiber, such as beta-1, 3-glucan, beta-1, 6-glucan, or beta-1, 4-glucan or mixtures thereof. In addition to beta-glucan naturally present in the grain (e.g., oats), beta-glucan can also be added as approved by the FDA. In certain embodiments, the grain (e.g., oat flour) preferably contains at least about 3%, at least about 4%, or about 3% to 5% or about 3.7% to 4% beta-glucan on a dry weight basis. In certain embodiments, the grain (e.g., oat flour) containing liquid, semi-solid, or solid product contains 0.1% to about 1.5% beta-glucan, or about 0.8% to 1.3% beta-glucan. Other amounts of beta-glucan are also useful. Additionally, in some embodiments, the grain (e.g., oat flour) can contain at least about 8%, 9%, or 10% or about 8% to about 12% total dietary fiber by weight. Furthermore, for example, in accordance with 21 CFR 101.81 a whole oat flour can be produced from 100 percent dehulled, clean oat groats by steaming and grinding, such that there is no significant loss of oat bran in the final flour, the final flour provides at least 4% beta-glucan on a dry weight basis, and the final flour provides at least 10% total dietary fiber on a dry weight basis.

In some embodiments, the soluble grain flour (e.g., oat flour) disperses in less than about 5 seconds in a liquid media at 25° C.

The product (e.g., soluble oat or barley flour) prepared in accordance with the process described above can be utilized in a variety of products such as: fruit juices, dairy beverages, carbonated soft drinks, ready-to-drink (RTD) beverages (for example, dairy-based beverages and juice-based beverages); powders such as for cold and hot instant beverages, instant pudding, custards, mousses, or gelatin, or as an additive to smoothies or shakes for example; dairy products such as yogurt, ice cream, oat-milk, and processed cheeses such as cream cheese; bakery products such as crackers, cookies, muffins, breads, pizza crust, bagels, cakes, crepes, and pancakes; ready-to-eat (RTE) snacks such as pudding, fruit leather, and fruit gel snacks; starters or side dishes such as soups (including, without limitation instant soups and ready-to-eat soups) and congee; seasoning mixes, dressings, and sauces; grain-based foods such as upma and hummus; meat-based foods such as meat balls; polenta; and fillings for food products such as mousse, cream, and fudge. The soluble oat or barley flour can also be used as texture modifiers for bakery products or as a replacement for gums, such as guar gum, for instant oatmeal products. Moreover, the soluble oat or barley flour can be used as a fat replacer in products such as cream-based dips. This list is not all-inclusive and one skilled in the art would recognize that the soluble oat or barley flour can be added to other beverages and food products in accordance with the invention.

In some embodiments, a beverage, for example, contains from about 1% to about 25% soluble oat or barley flour and from about 70% to about 95% total water, typically about 75% to about 90% total water, based on weight of the total drinkable beverage. The balance can contain sweeteners, flavors, fruits and other materials as desired.

The water should be suitable for use in food. The total water can come in part or in whole from other parts of the drinkable food, especially if milk, juices, or other water containing components are used. For instance, the milk can be dairy (e.g., whole, 2%, 1%, or non-fat) or non-dairy (e.g., soy). The milk can also be produced from powdered milk and water.

The beverage can also include a fruit component. The fruit component can include fruit juice, yogurt containing fruit, fruit puree; fresh fruit, fruit preserves, fruit sorbet, fruit sherbet, dried fruit powder, and combinations thereof. Typically, the fruit component has particles sufficiently small that the component can be safely swallowed without chewing. The fruit component and/or an added acidulant can be adjusted to obtain a desired pH, for example a pH of less than about 4.6.

Food products include cereals and ready-to-eat snack bars. A suitable amount of the granulated product is added to the food mixture.

Additional ingredients can be added to the beverage and food products. Such ingredients can include non grain-based ingredients. For example, flavoring agents, coloring agents, sweeteners, salt, as well as vitamins and minerals can be included. In one embodiment of the invention, flavoring agents such as strawberry, chocolate or cinnamon flavor is added to enhance the taste of product. Other fruit flavoring agent can also be useful to provide different tastes to the food product, for example, strawberry, mango and banana and mixtures thereof. Spices, in particular, cinnamon, can be used. In addition, any desired flavor or flavors can be used. Suitable sweeteners—artificial or natural can be added in the food product to provide a desired sweetness. For example, brown sugar, maple sugar or fruit sugar can be used. The non-grain based food component can be added in the range of about 10 to 75 wt. % of the total weight of the product.

Other optional ingredients, include, but are not limited to, salt, hydrocolloids, polysaccharides, thickeners, caffeine, dairy, coffee solids, tea solids, herbs, nutraceutical compounds, electrolytes, vitamins, minerals, amino acids, preservatives, alcohol, colorants, emulsifiers, and oils as known in the art.

The soluble oat or barley flour includes beta-glucan soluble fiber, such as beta-1, 3-glucan, beta-1, 6-glucan, or beta-1, 4-glucan or mixtures thereof. In addition to beta-glucan naturally present in the oats or barley, beta-glucan can also be added as approved by the FDA. In certain embodiments, the oat flour preferably contains at least about 3% to 5% or about 3.7% to 4% beta-glucan. In certain embodiments, the oat flour containing liquid product contains 0.1% to about 1.5% beta-glucan, or about 0.8% to 1.3% beta-glucan. Other amounts of beta-glucan are also useful.

As described, the present invention provides both healthy drinkable and edible beverage and food products which are convenient to consume on-the-go, making it especially appealing to consumers with today's hectic lifestyle. Some embodiments of the invention will now be described with reference to examples of food and/or beverage products.

In one embodiment, a cracker formula is typically made using whole wheat flour or wheat gluten. Instead the formula would be replaced with this hydrolyzed oat flour (e.g., soluble oat flour) to improve nutritional benefits (heart health) as well as provide adequate strength to the dough be sheeted and cut into crackers. The formula would include:

| Ingredient | |
|---|---|
| Modified corn starch | 10.00 |
| Oat flour, Hydrolyzed | 48.00 |
| Oat flakes, old fashioned | 17.00 |
| Brown sugar, free-flowing | 12.00 |
| Malt powder, Briess #10001 | 4.00 |
| Lecithin, powdered, Centrolex | 2.00 |
| Sodium aluminum phosphate | 0.80 |
| Sodium bicarbonate | 0.70 |
| Salt, flour | 0.50 |
| Corn Oil, with TBHQ, ADM | 5.00 |
| Total | 100.00 |

As another example, one embodiment of the invention provides a formula for oat ice cream comprising hydrolyzed oat flour (e.g., soluble oat flour) as follows.

| Ingredient | % |
|---|---|
| 2% Milk | 87.0 |
| Oat flour, hydrolyzed | 6.5 |
| Sugar | 5.4 |
| Cocoa powder | 0.8 |
| Flavor | 0.2 |
| Modified starch | 0.1 |
| Total | 100.0 |

It was discovered that the use of the soluble flour (e.g., a soluble flour comprising, consisting essentially of, or consisting of pulse, grain, at least a portion of pulse and/or at least a portion of grain, for example bran) prepared in accordance with the method described above provides unexpected processing improvements and properties over unprocessed oat flour or soluble oat flour prepared by other methods.

For example, flour used in RTE or RTD products is typically pasteurized or sterilized in order to kill microorganisms that could cause disease or spoilage. This high heat process ensures that the flour is safe and healthy to consume. Such pasteurization and sterilization cannot be easily done on dry flour. Hence, prior to pasteurization or sterilization, the flour needs to be completely hydrated to ensure appropriate heat transfer through the flour during the kill step. Full hydration and complete gelatinization of the flour are desired to ensure the viscosity of the product will not dramatically increase during further processing.

Native flour is typically hydrated by dispersing the flour in water and heating the slurry using an appropriate time and temperature combination that results in starch gelatinization. Typically the temperature is 90° C. and the time to hydrate fully is at least 25 minutes. Lower hydration temperatures will require longer times. Then the slurry needs to be cooled down to blend the other ingredients. Then the flour slurry can be pasteurized or sterilized by any suitable means such as High Temperature Short time (HTST) pasteurization or Ultra High Temperature (UHT) sterilization. Pasteurization or sterilization can be a useful or a necessary step for RTD or RTE liquid or semi-solid foods.

It was discovered that soluble flour made in accordance with the process described above hydrates without the need of a lengthy heating process of standard or typical grain flour (e.g., oat, barley, or wheat flour). For example, in flour comprising at least a portion of a grain (e.g., bran, whole grain, etc.) and/or a pulse, the quality of the at least a portion of the grain and/or pulse is maintained, that is the integrity of the flour is maintained throughout the process. Accordingly, in some embodiments, although starch molecules in the flour can be hydrolyzed to smaller starch molecules with smaller molecular weights, the relative mass ratio of the starch to other components in the flour remains substantially constant, or essentially constant, or constant. As an illustration, when the flour is a grain flour, whole grain status can be maintained throughout the process (e.g., hydrolysis, pelletizing, grinding, and/or milling process). With soluble flour, the flour can be hydrated at a lower temperature, for example, the temperature can be around chilled to room temperature, typically 4 to 30° C. reducing the total processing time by 1.5 hours. Typically the amount of soluble flour in the water is 2 wt. % to 10 wt. %, or 3 wt. % to 9 wt. %, or 4 wt. % to 8 wt. %. Then the flour can be further processed to prepare the RTE or RTD product (for example, by pasteurization).

Figure 2:
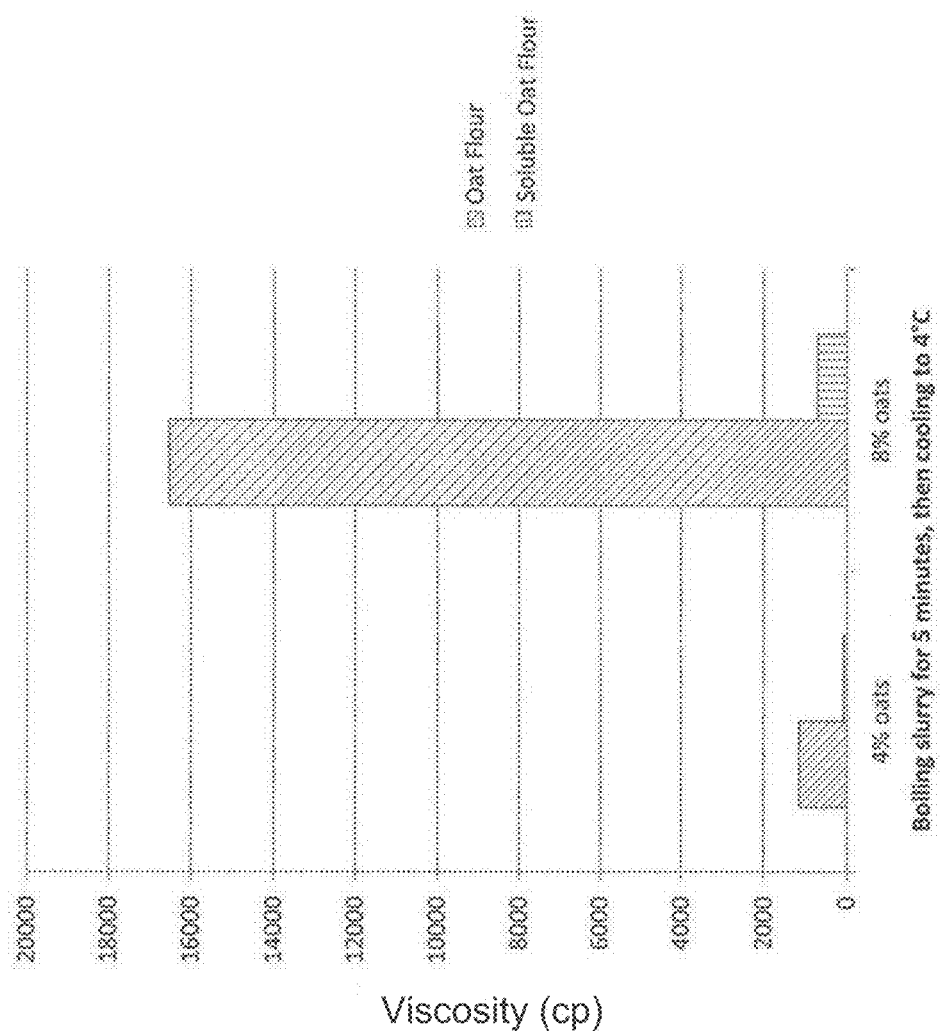
FIG. 2 depicts the viscosity of oat flour and soluble oat flour slurries after hydration.

Furthermore, it was discovered that after hydration, a slurry comprising, consisting essentially of, or consisting of a water and flour with gelatinized, hydrolyzed starch (e.g., the soluble flour slurry) has a much lower viscosity compared to a standard or typical flour slurry. For example, the soluble oat flour slurry has a much lower viscosity (in relative and/or absolute terms) compared to standard or typical oat flour slurry. Attention is drawn to FIG. 2 which demonstrates that standard oat flour produced a much higher viscosity than soluble oat flour especially at higher concentrations of oats. In fact, the viscosity of the soluble oat flour slurry at 8 wt. % oats is lower than the viscosity of oat flour at 4 wt. % oat concentration.

Such improved viscosity and hydration results were not expected and has thus allowed the soluble flour to be used in products to provide better properties such as better hydration and mixing properties, particularly without the need of elevated temperatures. The viscosity of hydrated soluble oat flour in water in amounts of 2 wt. % to 10 wt. % will generally range from 100 to 1600 cP at 24° C.

For typical oat flours, high shear mixing must be used with the hydrated flour prior to adding to beverage ingredients, to reduce viscosity. Because of the relatively low viscosity of the soluble oat flour, there is no need for such a high shear mechanical process step to reduce viscosity driven by starch. Gentle mixing is sufficient.

Therefore, benefits of using soluble flour, for example, soluble grain flour, for beverages instead of typical flour, for example, typical grain flour (e.g., typical oat flour), include simplified manufacturing processes and less capital investment for heating, mixing and cooling equipment.

Soluble flour, for example, soluble grain flour, is very effective in dairy beverages because no high temperature heating is required. As discussed above, typically high temperature and time is involved in grain flour hydration (e.g., oat flour hydration, barley flour hydration, etc.). If one wants to use typical grain flour (e.g., typical oat flour) in a dairy beverage, it is recommended to hydrate the grain flour (e.g., the oat flour) in water because heating fluid milk to the high temperatures required for hydration results in cooked milk flavors. To be able to produce a beverage with high concentration of dairy components, the dairy components must be added as a dairy powder. In contrast, soluble flour, for example, soluble grain flour, allows hydration to occur directly in the fluid milk, producing a product with better sensorial properties, for instance, a fresher flavor is associated with the product since the cold milk has not been subjected to a severe heat hydration treatment and therefore does not have the cooked notes commonly associated with heat treating milk. Attention is drawn to U.S. Ser. No. 13/547,733 which is hereby incorporated by reference in its entirety as an example and which describes the benefits of hydrolyzed oat flour in dairy beverages.

Soluble flour can also be used in juice beverages. In one embodiment, soluble flour, for example, soluble grain flour, can be hydrated in the juice at ambient temperatures or cold temperatures. The juice can be any suitable juice or juice/puree combination. Suitable juices can be acidic or non-acidic, fruit, vegetable, or combinations thereof. Non-limiting examples of juices and purees include, Acai, Aloe Vera Juice, Apple, Apricot Nectar, Bancha, Beet, Black Cherry, Black Currant, Blackberry, Blueberry, Boysenberry, Carrot, Celery, Coconut, Cranberry, Cucumber, Elderberry, Gogi Berry, Grape, Grapefruit, Kiwi, Strawberry, Tomato, Raspberry, Lemon, Lime, Mango, Orange, *Papaya* Nectar, Passion fruit, Pear, Pineapple, Plum, Pomegranate, Potato, Prune, Pummelo, Radish, Razzleberry, Sorrel, Spinach, Tangerine, Tomato, Turnip, Watercress, Watermelon, and Wheat Grass. Purees are well-known to those skilled in the art and are generally prepared from smashed or mashed fruits and vegetables.

As an example, suitable RTD juice products such as juice-based or milk-based smoothies can be prepared with ½ serving of whole grain oats per 8 oz. serving.

| Ingredient | wt. % |
| --- | --- |
| Fruit Juice | 65-80 |
| Fruit Puree | 10-30 |
| Soluble Oat Flour | 3.71 |

Flavors, colors, texturizers, anti-foaming agents, fruit pieces or other inclusions, and other additives can be added as is within the skill of the art. It is understood that the juice-based beverages can be made with many types of additives. Artificial and natural, non-nutritive and nutritive, sweeteners can be added if desired. Texturizers can be gums or starches. As noted below, the soluble oat flour can also wholly or partially replace certain texturizers such as gellan gum. The amount of soluble grains (e.g., soluble oats) added can be to provide up to 1 serving of whole grain (e.g., whole grain oats) per 8 oz. serving. Generally, the juice can include up to 8 wt. % soluble grain (e.g., soluble oats), generally 1 to 8%, or 2 to 4 wt. %.

Hence, soluble flour, for example, soluble grain flour, provides unexpected benefits for liquids such as beverages or yogurts. As discussed above, there is no need to hydrate soluble oat flour in water at high temperature. Instead room temperature or temperatures of 4 to 30° C. are suitable. Second, there is no need for a mechanical process step to reduce viscosity driven by starch. Third, there is no need of a cooling process of a heated oat slurry.

Figure 3:
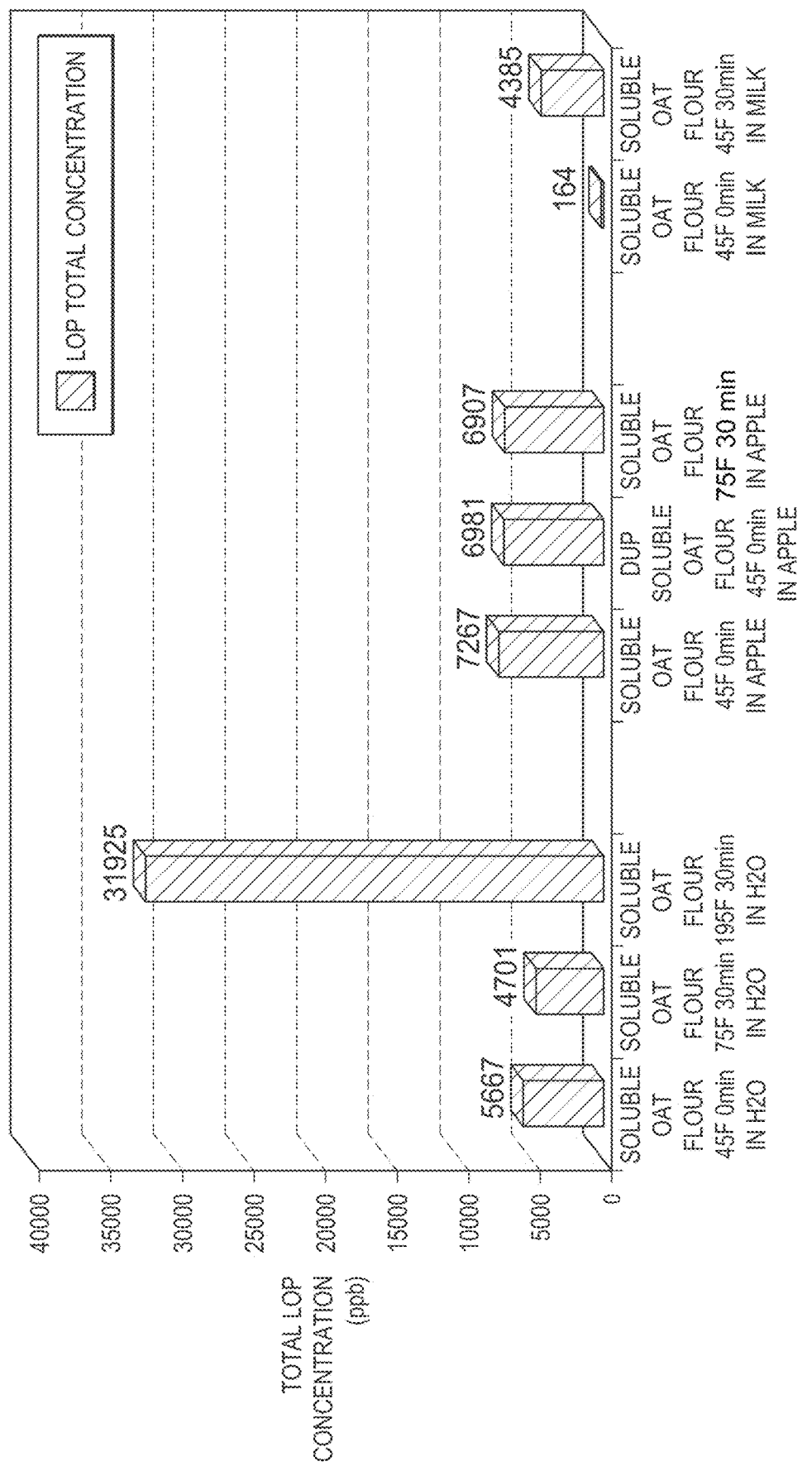
FIG. 3 depicts the analysis of lipid oxidation product ("LOP") in various hydration conditions for soluble oat flour.

FIG. 3 provides an analysis of lipid oxidation product under various hydration conditions. It is shown that the degree of oxidation of the soluble oat flour slurry is driven by hydration temperature and time. That is, FIG. 3 shows that a less oxidized compound was identified with juice samples prepared by cold juice hydration when compared to that prepared by high temperature water hydration. Note that the bar labeled "6981" represents a duplicate experiment for the bar labeled "7267."

Soluble flour, for example, soluble grain flour, as described herein can also be added to instant powders such as to provide instant cold beverages (e.g., chocolate milk) or whole grain oat "shots" for smoothie or other beverages. In some embodiments, the consumer purchases the instant powder and mixes it with a liquid, including, without limitation, water, juice, or milk. In some embodiments, soluble flour, for example, soluble grain flour, provides less and slower sedimentation of insoluble solids and further provides a less grainy or gritty mouthfeel compared to other flours, for example, grain flours (e.g., oat flours). Soluble oat flour also provides a slight oatmeal flavor bringing authenticity to the product versus a "raw flour" flavor when using oat flour. One aspect of the instant powder is provided below:

| Ingredient | wt % |
| --- | --- |
| Soluble Oat Flour | 50-70 |
| Sugar | 30-45 |
| Salt | 0.6-0.8 |
| Stabilizers | 0.7-0.9 |
| Flavors | 2.5-5 |

Figure 4:
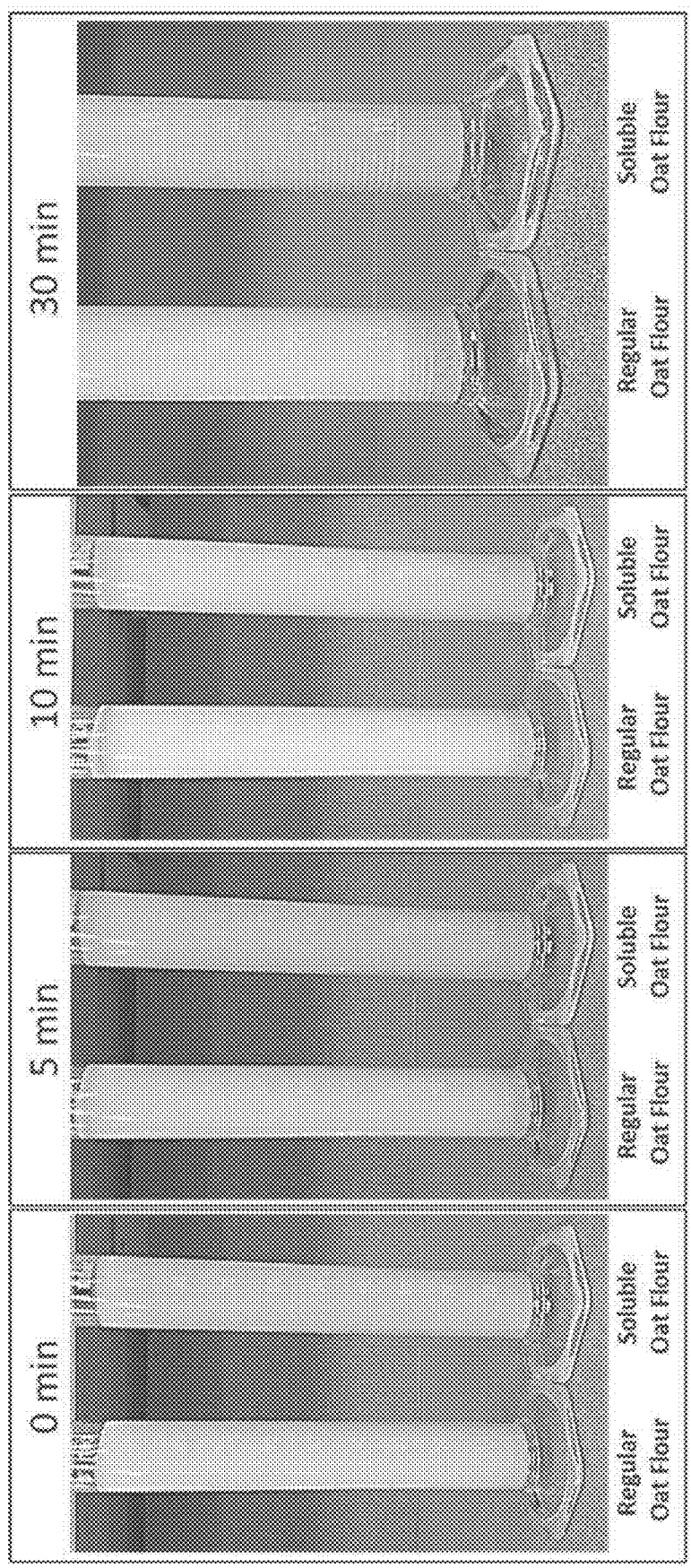
FIG. 4 is a photograph illustrating the amount of sedimentation observed when regular oat flour is mixed in cold water versus when the soluble oat flour is mixed with cold water.

Sensory testing (n=13) was performed on a cold instant beverage containing the soluble oat flour of the instant application compared to regular oat flour. FIG. 4 illustrates that the amount of sedimentation observed when regular oat flour was mixed with cold water was much greater than the sedimentation observed when soluble oat flour was mixed with cold water. Specifically, FIG. 4 shows the sedimentation of a sample containing regular oat flour and soluble oat flour suspensions after 5, 10 and 30 minutes following preparation. The separation of phases in the regular oat flour sample was observed after only 5 minutes following preparation. Additional results of the sensory tasting are shown in Table 1 below.

TABLE 1

Table 1

| Question | Regular Oat Flour | Soluble Oat Flour |
| --- | --- | --- |
| Which samples is grittier? | 58% | 42% |
| Which sample has a smoother mouthfeel? | 38% | 62% |
| Which sample has a more "raw flour" flavor? | 69% | 31% |

Figure 5:
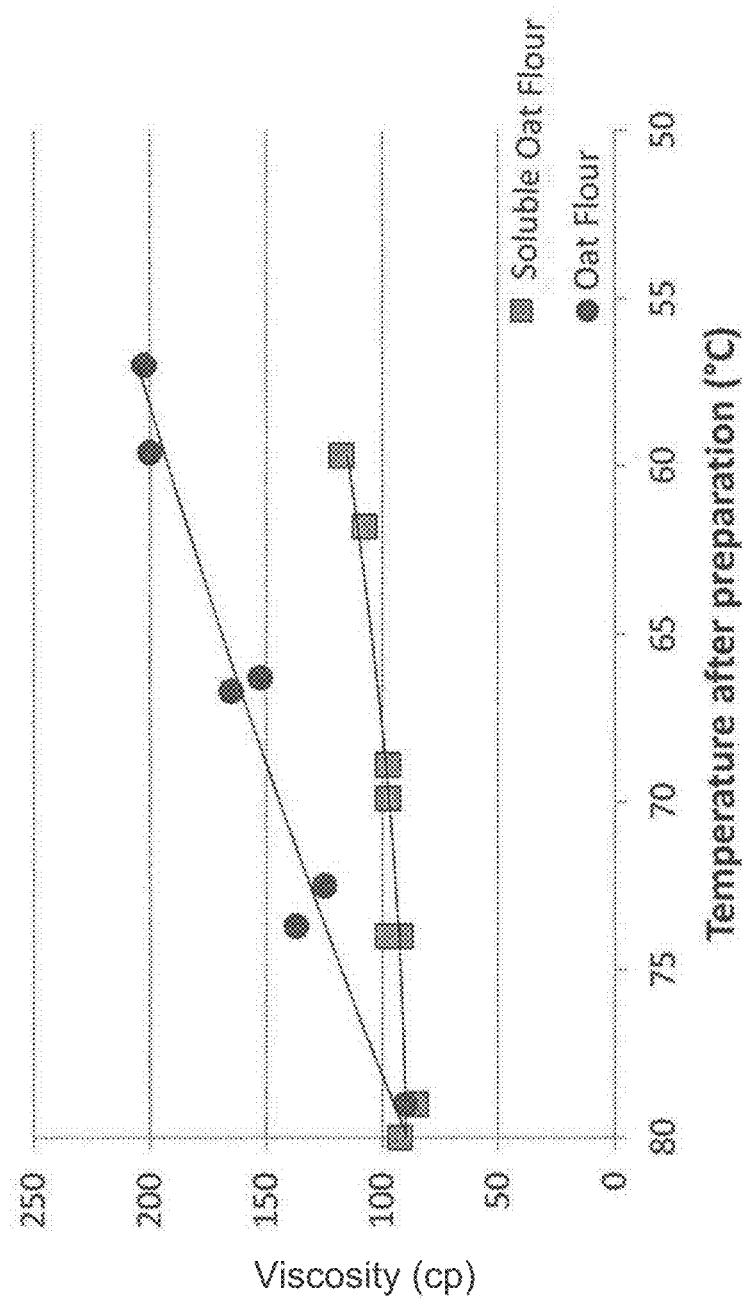
FIG. 5 depicts viscosity of instant hot beverages containing unprocessed oat flour and soluble oat flour after the beverages cool down.

Soluble flour, for example, soluble grain flour, as described herein can also be added to instant powders such as to provide instant hot beverages. Soluble flour, for example, soluble grain flour, provides less and slower sedimentation of insoluble solids and lower viscosity at temperatures at which hot beverages are customarily consumed. That is, there is a minimal viscosity increase as a beverage cools down when compared to typical flour processed by conventional oat milling methods. For example, FIG. 5 illustrates there is a minimal viscosity increase as a beverage comprising soluble oat flour cools down when compared to a beverage comprising typical flour processed by conventional oat milling methods.

Soluble flour, for example, soluble grain flour, included in powders for instant cold beverages can comprise 25 to 90 wt. % of the total powder weight. In particular, soluble flour, for example, soluble grain flour in a powder for instant cold beverages such as chocolate milk can comprise 50 to 70 wt. % of the total powder weight as noted in the example above. Additionally, soluble flour, for example, soluble grain flour, included in powders as shots for addition to already prepared beverages can comprise 50 to 100 wt. % of the total powder weight.

Notably, typical oat flour dispersed in hot water will significantly increase the viscosity of the liquid as the temperature decreases, typically, the viscosity will more than double as the temperature decreases (e.g., increases over 100%). In contrast, the soluble flour, for example, soluble grain flour, when dispersed in hot water in the same amount, will not significantly increase the viscosity of the liquid as the temperature decreases (e.g., increases no more than 40%.)

| Ingredient | wt % |
| --- | --- |
| Non-fat dry milk | 30-36 |
| Soluble Oat Flour | 28-32 |
| Sugar | 21-28 |
| Cocoa powder | 7-9 |
| Stabilizers | 1-4 |
| Salt | 0.1-.5 |

Flavors, colors, powdered milk, anti-foaming agents, stabilizers, salt, and other additives can be added to the instant powders for hot and cold beverages as is within the skill of the art. It is understood that the powders can be made with many types of additives. Artificial and natural, non-nutritive and nutritive, sweeteners can be used if desired. The amount of soluble oats depends on the amount desired in the final product. For example, a ½ to full serving of soluble whole grain (e.g., soluble oats) included in powders intended for hot beverages can comprise 25 to 50 wt. % of the total powder weight for instance 28 to 32 wt. % of the total powder weight. Again, a benefit to soluble powders, for example, soluble grain powders (e.g., soluble oat powders) is easy hydration when added to water or other liquids.

Figure 6:
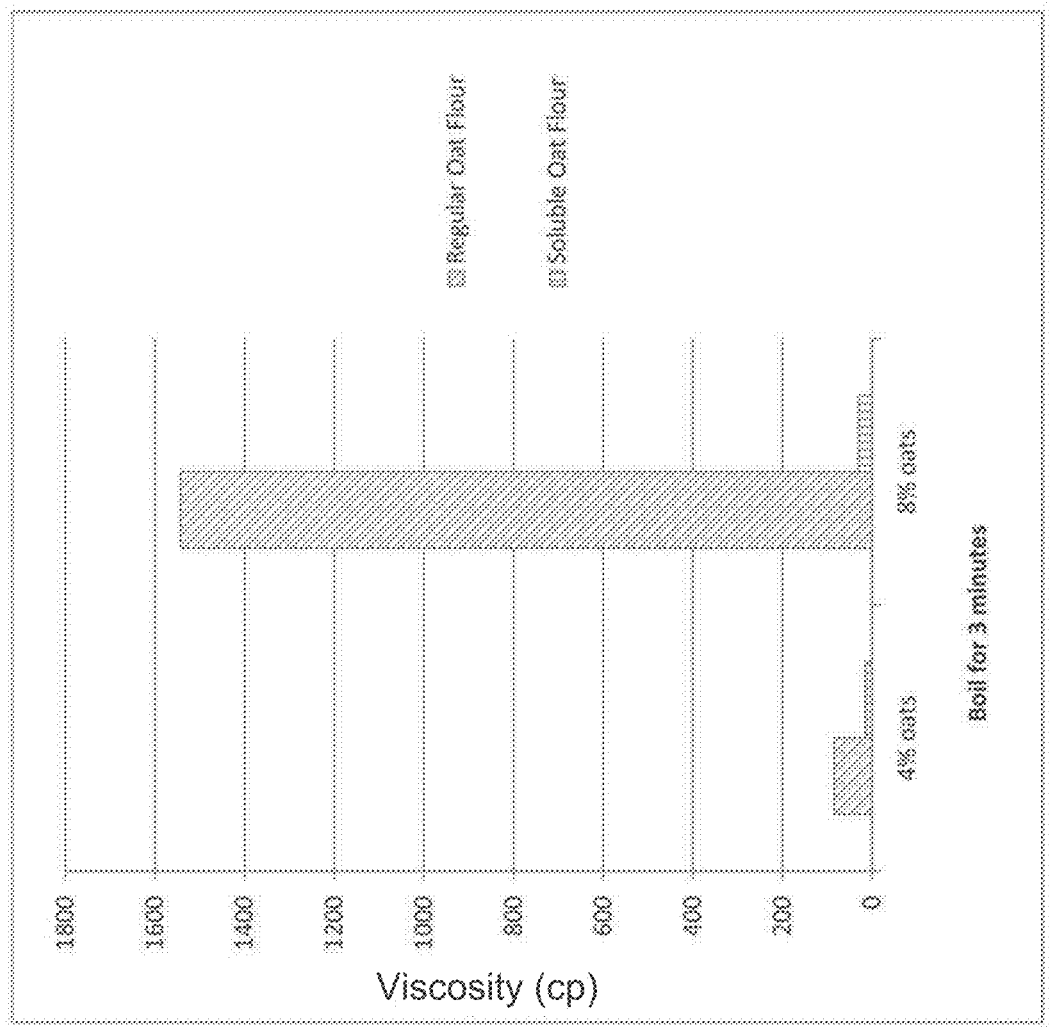
FIG. 6 depicts the viscosity of oat flour and soluble oat flour slurries after boiling in water for three (3) minutes.

Soluble flour, for example, soluble grain flour, can also be used in side dishes and entrees such as soups and congee. The easy hydration and lower viscosity of the soluble flour, for example, soluble grain flour, allows addition of higher amounts of whole grain (e.g., whole grain oats) per serving size providing increased health benefits. The soluble flour can be used in both instant soups and ready-to-eat soups. In one aspect, a ready-to-eat soup comprising about 2 to 10 wt. % of soluble oat flour based on total weight of the soup wherein the soluble oat flour provides at least ½ serving of whole grains can be prepared. Attention is drawn to FIG. 6 which demonstrates that standard oat flour produced a much higher viscosity than soluble oat flour especially at higher concentrations of oats. Further, 4% soluble oat flour per 8 oz. serving will ensure delivery of a ½ serving of whole grains which is about 8 grams of oats. Similarly, 8% soluble oat flour per 8 oz. serving will ensure delivery of 1 whole serving of whole grains which is about 16 grams of oats. The viscosity measurements shown in FIG. 6 were taken immediately after boiling for 3 minutes.

A butternut squash soup can be prepared as follows:

| Ingredient | wt % |
| --- | --- |
| Chicken or vegetable broth | 45-60 |
| Butternut squash | 30-40 |
| Onions | 7-10 |
| Soluble Oat Flour | 3-5 |
| Butter and oil | 1.2-1.5 |
| Garlic | 0.2-1 |
| Salt | 0.2-0.6 |
| Spices | 0.01-0.05 |

Suitable spices can be a combination of cinnamon, allspice, cayenne pepper, and black pepper. Any of the ingredients can be modified or replaced as appropriate for the particular desired result.

Soluble flour, for example, soluble grain flour, can also be used in semi-solid dairy products such as yogurt, ice cream, or spreads. In some embodiments, the benefits of using the soluble flour of the instant application in semi-solid dairy products include easy hydration and/or minimal to no increase of viscosity during processing as shown in FIG. 5. For example, yogurt can be prepared with a ½ serving of whole grain oats per 6 oz. serving:

| Ingredient | wt % |
| --- | --- |
| Milk/Other dairy | 89.1 |
| Soluble Oat Flour | 5.3 |
| Sugar | 5 |
| Texturizers | 0.6 |
| Yogurt Culture | Mfr spec. |

Flavors, colors, texturizers, fruit preparations, fruit pieces or other inclusions, and other additives can be added as is within the skill of the art. It is understood that the yogurt can be made with many types of additives and that the amounts of the ingredients can vary. The sugar can be wholly or partially replaced with any suitable artificial and natural, non-nutritive and nutritive, sweeteners. Texturizers can be gums or starches. As noted below, the soluble flour, for example, soluble grain flour, can also wholly or partially replace certain texturizers such as guar gum. The amount of soluble components, for example, soluble grain (e.g., oats) added can be to provide up to 1 serving of whole grain oats per 6 oz. serving. Generally, for example, the yogurt can include up to 11 wt. % soluble oats, generally 2 to 11%, or 2.5 to 6 wt. %.

Soluble flour, for example, soluble grain flour, as described herein can also be added to instant powders such as to provide instant puddings. Such products provide a smoother texture with a reduced grainy or gritty mouthfeel.

| Ingredient | wt % |
| --- | --- |
| Modified starches/maltodextrin | 45-50 |
| Sugar | 20-25 |
| Soluble Oat Flour | 20-25 |
| Tetrasodium pyrophosphate | 0.5-2.0 |
| Flavors | 0.1-2.0 |
| Color | 0.1-2.0 |
| Acetylated monoglycerides | 0.1-1.5 |
| Dipotassium phosphate | 0.1-1.5 |

Moreover, additional testing showed that the instant pudding product made with the soluble oat flour described herein provides a firmer, more pudding-like texture compared to the same product made with regular oat flour using the same amount of texturizers. Table 2 below identifies the result of a sensory testing of the pudding products.

Table 2: Sensory tasting of an instant pudding. Results show percent of responses (n=13).

TABLE 2

| Question | Regular Oat Flour | Soluble Oat Flour |
| --- | --- | --- |
| Which samples is grittier? | 77% | 23% |
| Which sample has a smoother texture? | 23% | 77% |

Flavors, colors, powdered milk, anti-foaming agents, stabilizers, salt, and other additives can be added to the instant powders for pudding as is within the skill of the art. It is understood that the powders can be made with many types of additives. Artificial and natural, non-nutritive and nutritive, sweeteners can be used if desired. The amount of soluble oats depends on the amount desired in the final product. For example, soluble oats included in powders intended for puddings can comprise 10 to 50 wt. % of the total powder weight, for instance, 20 to 25 wt. % of the total powder weight.

Soluble flour, for example, soluble grain flour, can be added to a variety of bakery products in combination with oat, wheat, and/or other grain and/or pulse flour. Baked products include, but are not limited to, cookies, muffins, breads, bagels, pizza crust, cakes, crepes, and pancakes. Soluble oat flour provides improved texture with typical commercial oat flour versus such oat flour alone.

Texturizers are typically gums or starches (e.g., corn starch). Instead of such typical texturizers, soluble flour, for example, soluble grain flour, can be used to improve the textural properties of baked products. For example, the soluble oat flour can be present in amounts of 2 to 10 wt. % as a texturizer.

As an illustration, soluble flour, for example, soluble grain flour, can be used as a texturizer in soft baked cookies. For example, cookies made with oat flour and/or oat flakes to provide ½ serving of whole grain oats (8 g) can have up to about 25 wt. % of the oat flour replaced with soluble oat flour. Replacement of a portion of the oat flour with soluble oat flour provides a moister texture. The cookie containing soluble oat flour can also provide a more crumbly texture. In limited instances a chewier texture was also observed. A suitable soft baked cookie recipe:

| Ingredient | wt. % |
| --- | --- |
| Oat flakes and Oat flour | 17-26 |
| Sugars: sucrose, invert sugar, | 17-26 |
| Wheat flour | 15-25 |
| Shortening and oils | 10-16 |
| Food fibers | 5-8 |
| Water | 5-7 |
| Soluble Oat Flour | 2-5 |
| Egg solids | 1.5-2.2 |
| Corn syrup | 1.3-2.0 |
| Leavening agents | 1.2-1.8 |
| Emulsifiers | 0.8-1.2 |
| Salt | 0.3-0.4 |

Sensory testing (n=13) was conducted on cookies made in accordance with the formula above along with cookies made by replacing the soluble oat flour with regular oat flour. The results are included in Table 3 below.

TABLE 3

| Question | Regular Oat Flour | Soluble Oat Flour |
| --- | --- | --- |
| When broken apart, which samples seems more crumbly? | 31% | 69% |
| Which sample has a moister texture? | 23% | 77% |

Any of the ingredients can be modified or replaced as appropriate for the particular desired result.

Soluble flour, for example, soluble grain flour, can be used in muffins. For example, muffins made with oat flour to provide 1 full serving of whole grain oats (16 g) can have up to about 50 wt. % of the oat flour replaced with soluble oat flour. Replacement of a portion of the oat flour with soluble oat flour provides a moister texture and more crumbly product. A suitable muffin recipe:

| Ingredient | wt. % |
| --- | --- |
| Wheat flour | 15-18 |
| Sugar | 6-8 |
| Leavening agents | 1.8-2.3 |
| Salt | 0.3-0.4 |
| Eggs | 6-8 |
| Milk | 22-28 |
| Butter | 7-9 |
| Blueberries | 9-12 |
| Oat flour | 7-9 |
| Soluble Oat Flour | 7-9 |
| Water | 4-5 |

Sensory testing (n=13) was conducted on muffins made in accordance with the formula above along with muffins made by replacing the soluble oat flour with regular oat flour. The results are included in Table 4 below. Further, the majority of panelists noted that the top of the muffins containing the soluble oat flour had a crustier texture and more coarse appearance.

TABLE 4

| Question | Regular Oat | Soluble Oat |
| --- | --- | --- |
| Which sample has a moister texture? | 42% | 58% |
| Which sample is more crumbly? | 42% | 58% |

Any of the ingredients can be modified or replaced as appropriate for the particular desired result.

Soluble flour, for example, soluble grain flour, can also be used in ready-to-eat high moisture snacks such as RTE puddings, fruit leather, and fruit gels. The lower viscosity of the gelatinized soluble flour, for example, hydrated pulse flour (e.g., pea flour) or hydrated grain flour (e.g., oat flour), dispersed in a liquid at the same concentration level as gelatinized typical pulse flour and/or grain (e.g., oats) allows the addition of higher amounts of whole pulse and/or whole grain (e.g., whole grain oats) per serving. Also, in some embodiments, soluble flour, for example, soluble grain flour, provides improved mouthfeel (less slimy or less slippery mouthfeel and lower undesirable mouthcoating).

A fruit Gel snack can be prepared as follows:

| Ingredient | wt. % |
| --- | --- |
| Fruit puree | 43-53 |
| Water | 28-34 |
| Soluble Oat Flour | 8-14 |
| Sugars: sucrose and fructose | 8-10 |
| Acidulants | 0.9-1.1 |
| Flavors | 0.9-1.1 |
| Texturizers | 0.25-0.5 |
| Calcium chloride | 0.1-0.2 |

Sensory testing (n=13) was conducted on fruit gels made in accordance with the formula above along with fruit gels made by replacing the soluble oat flour with regular oat flour. The results are included in Table 5 below.

TABLE 5

| Question | Regular Oat Flour | Soluble Oat Flour |
| --- | --- | --- |
| Which sample is slimier? | 62% | 38% |

Colors, preservatives, and other additives can be as needed or desired. Further, any of the ingredients can be modified or replaced as appropriate for the particular desired result.

Soluble flour, for example, soluble grain flour, can also be used in sauces and seasoning mixes for preparation of various foods such as gravies, creamy sauces, and seasoning mixes added during preparation of rice or pasta.

Grain and/or pulse flour with hydrolyzed starch can also be used as a texturizer. For example, soluble flour (e.g., soluble grain flour or soluble pulse flour) can be used as a texturizer in instant oatmeal products. Texturizers improve the overall texture of a bowl of instant oatmeal. The instant oatmeal comprises oat flakes and a powder comprising flavors, sweeteners, and texturizers such as guar gum. The texturizers are generally present in an amount of 0 to 1 wt. % based on the total weight of the instant oatmeal dry mix. Soluble flour, for example, soluble grain flour, can replace a portion or all of the guar gum. For example, a suitable instant oatmeal dry mix will contain 0 wt. % guar gum and 0.09 wt. % to 0.3 wt. % soluble oat flour based on total weight of the instant oatmeal dry mix.

Soluble oat flour was used to replace all of the guar gum in instant oatmeal in selected varieties. In some embodiments, soluble oat flour level was 50 to 75% guar gum usage rate. No significant differences were detected. A sensory discrimination test (Triangle test) was used with 60 panelists to evaluate if there were significant differences between oatmeal samples made with guar gum or soluble oat flour. Panelists were presented with 3 samples, from which 2 were the same and 1 was different. Panelists were asked to identify the different sample. No statistically significant differences were found between samples made with guar gum or soluble oat flour in two varieties of instant oatmeal.

Figure 7:
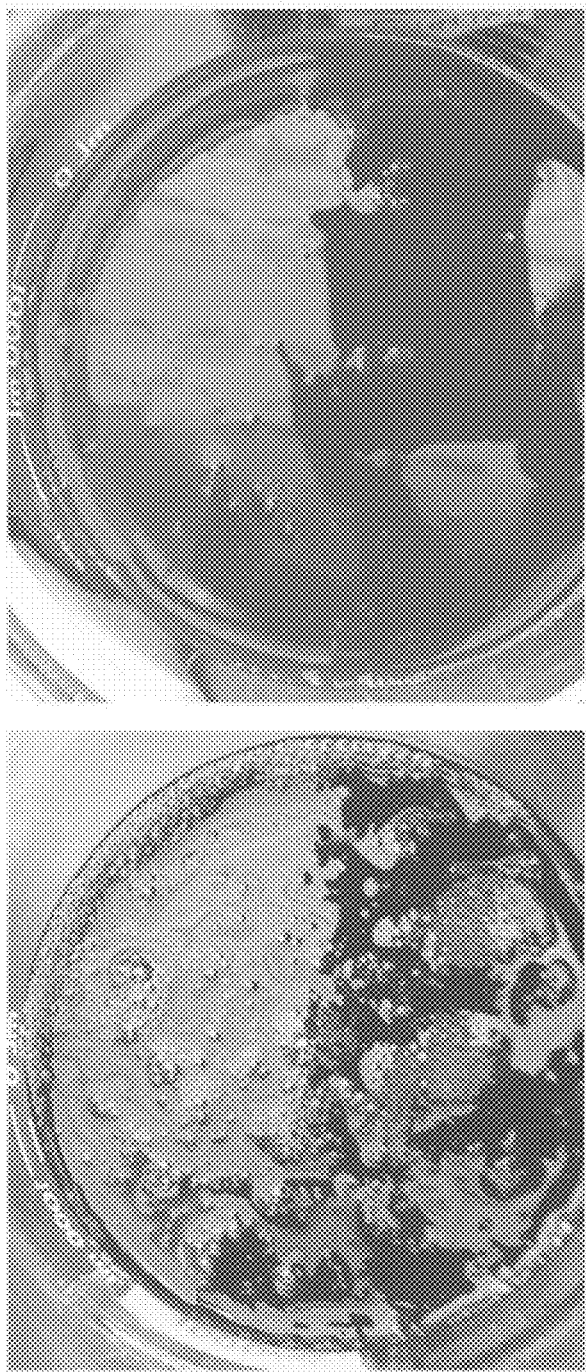
FIG. 7 is a photograph illustrating the antifoaming properties observed when the soluble oat flour is included in a slushie.
Figure 8:
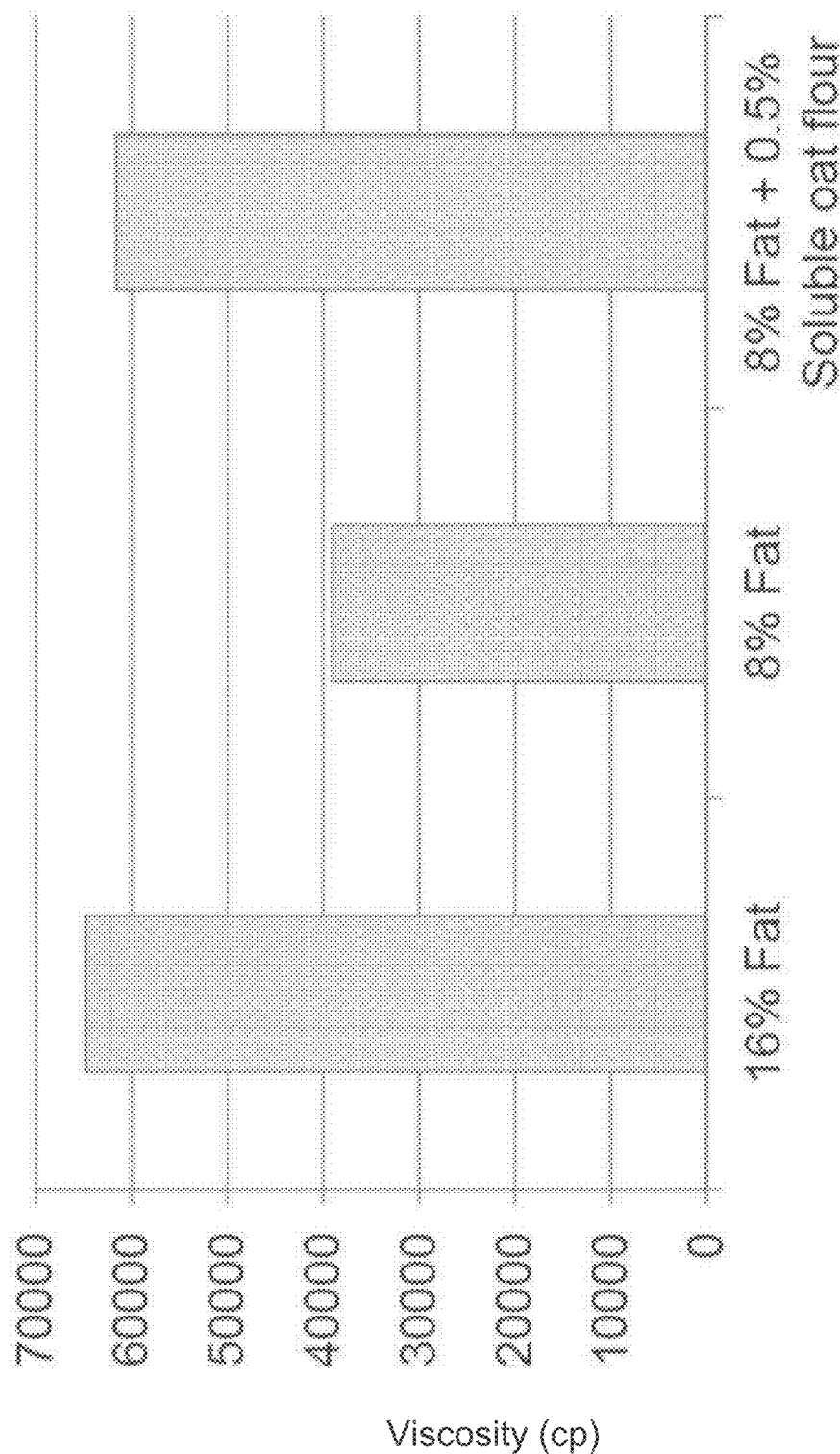
FIG. 8 depicts the viscosities of a full fat dip, a 50% reduced fat dip, and a 50% reduced fat dip containing soluble oat flour.

Soluble flour, for example, pulse flour and/or soluble grain flour with hydrolyzed starch, can be used in frozen commodities such as slushies and ice cream. In one aspect, a frozen commodity selected from the group consisting of ice cream and slushies comprising grain and/or pulse flour with hydrolyzed starch (e.g., soluble oat flour) in an amount of 2 to 10 wt. % based on total weight of the frozen commodity can be prepared. It was discovered, for example, that grain and/or pulse flour with hydrolyzed starch (e.g., soluble oat flour) can be used in slushie and ice cream products for not only the health benefits of the flour (e.g., whole grain oat flour), but because of the lower viscosity benefits during processing of these products, since the grain and/or pulse flour with hydrolyzed starch (e.g., soluble oat flour) does not require hydration like regular grain and/or starch flour (e.g., oat flour). Moreover, slushies made using the soluble oat flour of the instant invention exhibited antifoaming properties as illustrated in FIG. 7. The term "antifoaming properties" as used herein refers to the ability of a component to reduce or prevent the formation of air bubbles or foam during processing of liquids or semisolids.

A ready-to-eat mixed berry slushie can be prepared as follows:

| Ingredient | wt. % |
| --- | --- |
| Filtered water | 45 |
| Sucrose | 16 |
| Fruit purees | 14.8 |
| White grape juice | 12 |
| Soluble oat flour | 4.6 |
| Yellow carrot juice | 4.0 |
| Sweet potato concentrate | 2.4 |
| Ascorbic acid | 0.8 |
| Xanthan gum and others | 0.8 |

The water should be suitable for use in food such as water treated by reverse osmosis. The total water can be provided in part or in whole from other parts of the food, especially if milk, juices, or other water containing components are used. For instance, the milk can be dairy (e.g., whole, 2%, 1%, or non-fat) or non-dairy (e.g., soy). The milk can also be produced from powdered milk and water.

Additional ingredients can be added to the beverage and food products. Such ingredients can include pulse, non-pulse, grain and/or non-grain-based ingredients. For example, flavoring agents, coloring agents, sweeteners, and salts. Flavoring agents such as fruit flavors, chocolate flavors, or spice flavors can be added to enhance the taste of the product. Fruit flavoring agents include, for example, strawberry, mango, banana and mixtures thereof. Spices, in particular, cinnamon, can be used. In addition, any desired flavor or flavors can be used.

Suitable sweeteners—artificial or natural, nutritive or non-nutritive, can be added in the food product to provide a desired sweetness. For example, brown sugar, maple sugar or fruit sugar can be used. It is noted that the percentage of soluble grain flour (e.g., oat flour, barley flour, etc.) can increase if high intensity sweeteners are used.

Other optional ingredients can include, but are not limited to, hydrocolloids, polysaccharides, thickeners, caffeine, dairy, coffee solids, tea solids, herbs, nutraceutical compounds, electrolytes, vitamins, minerals, amino acids, preservatives, alcohol, colorants, emulsifiers, and oils as known in the art. Fruit and nut components can also be included as well as chips or pieces such as chocolate chips. Fruit components can include fruit puree; fresh fruit, fruit preserves, fruit sorbet, fruit sherbet, dried fruit powder, and combinations thereof. Typically, fruit or nut component have particles sufficiently small that the component can be safely swallowed without chewing. Acidulants can be used to adjust the pH, for example a pH of less than about 4.6 for an acidic beverage—e.g., juices or colas.

The grain and/or pulse flour with hydrolyzed starch, for example, soluble grain flour, also can be used as a fat replacer. For instance, the soluble oat fiber was used as a fat replacer in creamy dips to obtain a 50% fat reduction. FIG.

8 depicts the viscosities of a full fat dip, a 50% reduced fat dip, and a 50% reduced fat dip containing soluble oat flour. In particular, a 50% reduced fat dip containing the soluble oat flour described herein exhibited a viscosity similar to the full fat dip.

A reduced fat dip can be prepared as follows:

| Ingredient | wt. % |
|---|---|
| Water | 77.85 |
| Oil | 8 |
| Starch | 3 |
| Seasoning/flavorant | 4 |
| Protein | 3 |
| Acids | 1.5 |
| Salt | 1.5 |
| Emulsifier | 0.5 |
| Phosphate | 0.3 |
| Gums | 0.2 |
| Soluble oat flour | 0.15 |

Additional Examples

Aspects of the invention relate to food products containing highly dispersible, soluble whole oat flour. In some embodiments, the soluble whole oat flour maintains its standard of identity as whole grain and thus has the characteristics of whole grain oats.

Aspects of the present invention relate to the use of the soluble oat flour in various food products including liquid food products such as beverages, semi-solid food products such as yogurt, and solid food products such as bakery items in order to provide enhanced health benefits. Also, although the invention is described with reference to a composition comprising a grain (e.g., oat or barley), in some embodiments, any starch-containing component, for example, any food grade starch-containing component (e.g., one and only one grain, grains, one and only one pulse, pulses, a portion of a grain, a portion of each of a plurality of grains, a portion of each of a plurality of pulses, and/or combinations thereof) can be substituted for the grain described. For example, in some embodiments, a different grain can be substituted for the grain described. In addition, in some embodiments, a pulse can be substituted for the grain described. In some embodiments, a portion of a pulse is substituted for the grain described. Furthermore, in some embodiments, a pulse and a grain can be substituted for the grain described. Also, in some embodiments, a plurality of grains and/or a plurality of pulses can be substituted for the grain described. As another example, in some embodiments, a portion of a grain, for example, bran (e.g., from wheat, oat, corn, rye, rice, and/or barley) can be substituted for the grain described.

Additionally, in some embodiments, additional components can be added to the grain described. In some embodiments, a pulse can be added to the grain described. Furthermore, in some embodiments, a pulse and a grain can be added to the grain described. Also, in some embodiments, a plurality of grains and/or a plurality of pulses can be added to the grain described. As another example, in some embodiments, bran (e.g., wheat, oat and/or barley) can be added to the grain described.

Figure 9:
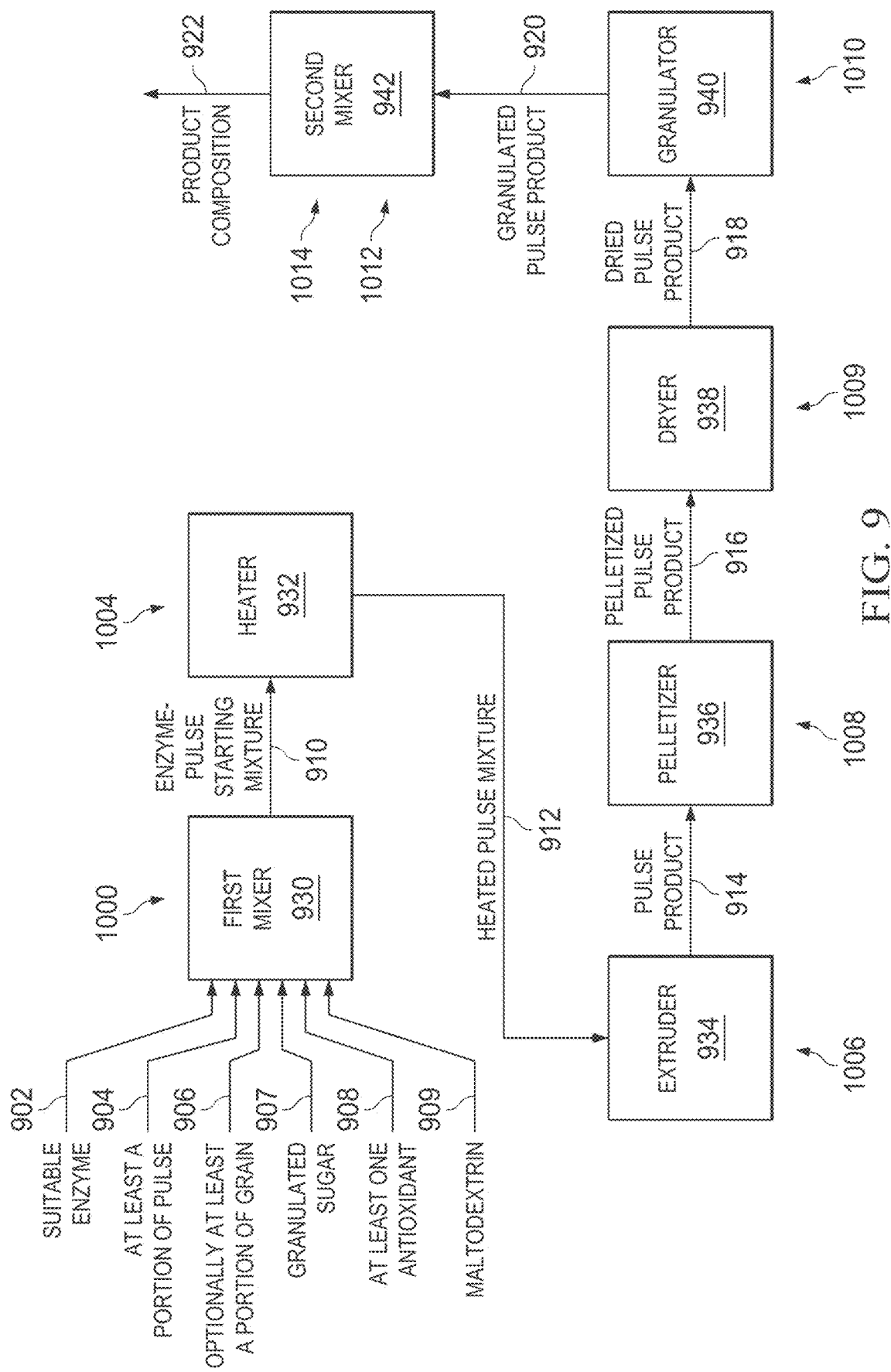
FIG. 9 depicts a block flow diagram illustrating one embodiment of a process for producing a composition comprising gelatinized, hydrolyzed starch.
Figure 10:
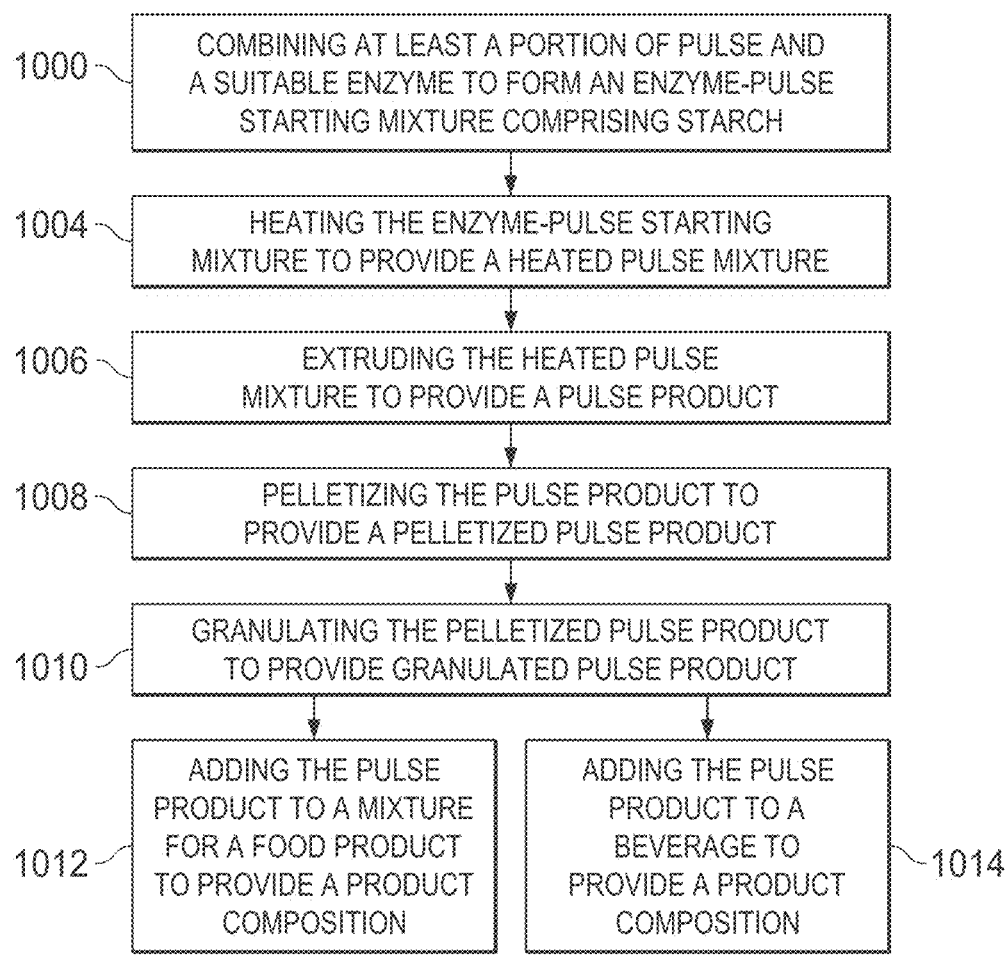
FIG. 10 depicts a schematic flow chart illustrating one embodiment of a process for producing a composition comprising gelatinized, hydrolyzed starch.

One embodiment of the invention will now be described with reference to FIG. 9 and FIG. 10. FIG. 9 depicts a block flow diagram illustrating one embodiment of a process for producing a composition comprising gelatinized, hydrolyzed starch. FIG. 10 depicts a method (e.g., for forming a composition comprising gelatinized, hydrolyzed starch) comprising a plurality of steps.

First, a combining step 1000 comprises combining at least a portion of pulse 904 (e.g., a portion of a pulse, whole pulse, or whole pulse flour) and a suitable enzyme 902 (e.g., endo-α-amylase) to form an enzyme-pulse starting mixture 910 comprising starch. As another example, the combining step 1000 can comprise combining at least a portion of pulse 904, at least a portion of grain 906 (e.g., a portion of a grain, whole grain, or whole grain flour) and a suitable enzyme 902. In some embodiments, a pulse starting mixture comprises the at least a portion of pulse 904, and the pulse starting mixture is combined with the suitable enzyme 902 to form the enzyme-pulse starting mixture 910. In some embodiments, the at least a portion of pulse 904, the suitable enzyme, and optionally other components, are combined in a mixer (e.g., a first mixer 930) to provide the enzyme-pulse starting mixture 910. In some embodiments, the enzyme-pulse starting mixture 910 comprises a mass ratio of granulated sugar 907 to pulse flour from about 0.03 to about 0.3; a mass ratio of maltodextrin 909 to pulse flour from about 0 to about 0.3; and an effective amount of at least one antioxidant 908. The pulse (e.g., from which the at least a portion of pulse 904 is derived) can be selected from the group consisting of peas, lentils, chickpeas, navy beans, black turtle beans, cranberry beans, kidney beans, pinto beans, small red beans, Dutch brown beans, pink beans and any combination thereof. Furthermore, the at least a portion of pulse 904 can be pulse flour (e.g., whole pulse flour). Additionally, in some embodiments, the pulse starting mixture comprises about 90 to about 95% (by total weight of the starting mixture) whole pulse flour. As used herein, "whole pulse" can be the whole edible portion of the pulse, for example, the whole grain seed, pea, or bean as applicable.

Second, a heating step 1004 comprises heating the enzyme-pulse starting mixture 910 (e.g., in a heater 932) to between about 120° F. (48.89° C.) and about 200° F. (93.33° C.) to begin to hydrolyze the starch (e.g., starch molecules), thereby providing a heated pulse mixture 912. In some embodiments, during the heating, the enzyme-pulse starting mixture 910 is heated to at least about 140° F. (60° C.), 180° F. (82.22° C.), 200° F. (93.33° C.), or 212° F. (100° C.), or about 140° F. (60° C.) to about 212° F. (100° C.), or about 140° F. (60° C.) to about 180° F. (82.22° C.).

Third, an extruding step 1006 comprises extruding the heated pulse mixture 912 (e.g., in an extruder 934 to continue hydrolyzing the starch and further to gelatinize and cook the heated pulse mixture 912), thereby providing a pulse product 914 (e.g., a product comprising at least a portion of pulse or whole pulse). For example, the pulse product 914 can comprise hydrolyzed starch (e.g., gelatinized, hydrolyzed starch). In some embodiments, the extruding occurs at a barrel temperature of about 140° F. (60° C.) to about 350° F. (176.67° C.), or about 140° F. (60° C.) to about 250° F. (121.11° C.). In some embodiments, during the extruding step 1006, the heated pulse mixture 912 is heated to a temperature of about 212° F. (100° C.) to about 320° F. (160° C.), or about 212° F. (100° C.) to about 260° F. (126.67° C.).

Fourth, an optional pelletizing step 1008 comprises pelletizing the pulse product 914 (e.g., in a pelletizer 936) to form pelletized pulse product 916 (e.g., pulse flour).

Fifth, an optional drying step 1009 comprises drying the pelletized pulse product 916 (e.g., in a dryer 938) to provide a dried pulse product 918 (e.g., a dried pelletized pulse product). In some embodiments, the dried pulse product 918 is granulated after it is dried.

Sixth, an optional granulating step 1010 comprises granulating the pelletized pulse product 916 or dried pulse product 918 (e.g., in a granulator 940) to form granulated pulse product 920 (e.g., granulated pulse flour).

Seventh, some embodiments comprise an optional adding step (e.g., a first adding step 1012 and/or a second adding step 1014). For example, a first adding step 1014 can comprise adding the pulse product 914 (e.g., the pulse product 914 from the extruder, pelletized pulse product 916, dried pulse product 918, and/or granulated pulse product 920) to a beverage to provide a product composition 922 (e.g., a beverage comprising pulse). In some embodiments, the beverage is selected from the group consisting of fruit juices, dairy beverages, and carbonated soft drinks. In some embodiments, the pulse product 914 is added to the beverage to provide the product composition 922 with 1 to 25% soluble fiber based on total weight of the product composition 922. As another example, a second adding step 1012 can comprise adding the pulse product 914 to a mixture for a food product (e.g. to provide a product composition 922). In some embodiments, the food product is selected from the group consisting of bars, cereals, puddings, smoothies, ice cream, cookies, and crackers. In some embodiments, the adding step occurs in a mixer (e.g., a second mixer 942).

In some embodiments, a composition comprising at least a portion of pulse 904 (e.g., a pulse composition) is also a composition comprising at least a portion of pulse 904 and at least a portion of grain 906 (e.g., a pulse-and-grain composition). For example, in some embodiments, the enzyme-pulse starting mixture 910 is an enzyme-pulse-and-grain starting mixture; the heated pulse mixture 912 is a heated pulse-and-grain mixture; the pulse product 914 is a pulse-and-grain product; the pelletized pulse product 916 is a pelletized pulse-and-grain product; the dried pulse product 918 is a dried pulse-and-grain product; the granulated pulse product 920 is a granulated pulse-and-grain product; and/or any combination thereof.

In some embodiments, the invention provides a method (e.g., for providing a pulse product) with several steps. For example, a first step comprises combining at least a portion of pulse (e.g., a portion of a pulse, whole pulse, or whole pulse flour) and a suitable enzyme to form an enzyme-pulse starting mixture comprising starch. In some embodiments the enzyme-pulse starting mixture further comprises sugar (e.g., granulated sugar), at least one antioxidant, a maltodextrin, and/or any combination thereof. Furthermore, the pulse can be selected from the group consisting of peas, lentils, chickpeas, navy beans, black turtle beans, cranberry beans, kidney beans, pinto beans, small red beans, Dutch brown beans, pink beans, and any combination thereof. Additionally, in some embodiments, the at least a portion of pulse is pulse flour (e.g., whole pulse flour).

In some embodiments, the enzyme-pulse starting mixture comprises: a mass ratio of sugar (e.g., granulated sugar) to pulse flour from about 0.03 to about 0.3; a mass ratio of maltodextrin to pulse flour from about 0 to about 0.3; and an effective amount of at least one antioxidant. Furthermore, in some embodiments, a pulse starting mixture comprises the at least a portion of pulse, and the pulse starting mixture is combined with the suitable enzyme to form the enzyme-pulse starting mixture. As an example, the pulse starting mixture can comprise about 90 to about 95% by weight whole pulse flour.

A second step comprises heating the enzyme-pulse starting mixture to between about 120° F. (48.89° C.) and about 200° F. (93.33° C.) to begin to hydrolyze the starch (e.g., starch molecules), thereby providing a heated pulse mixture.

In some embodiments, during the heating the enzyme-pulse starting mixture is heated to at least about 140° F. (60° C.), 180° F. (82.22° C.), 200° F. (93.33° C.), or 212° F. (100° C.) or about 140° F. (60° C.) to about 212° F. (100° C.), or about 140° F. (60° C.) to about 180° F. (82.22° C.).

A third step comprises extruding the heated pulse mixture to continue hydrolyzing the starch and further to gelatinize and cook the heated pulse mixture thereby providing a pulse product (e.g., at least a portion of pulse) comprising gelatinized, hydrolyzed starch. In some embodiments, the extruding occurs at a barrel temperature of about 140° F. (60° C.) to about 350° F. (176.67° C.), or about 180° F. (82.22° C.) to about 320° F. (100° C.), or about 140° F. (60° C.) to about 250° F. (121.11° C.). Additionally, in some embodiments, during the extruding, the heated pulse mixture is heated to a temperature of about 212° F. (100° C.) to about 260° F. (126.67° C.).

Some embodiments further comprise pelletizing the pulse product to form pelletized pulse product (e.g., pellets or pelletized pulse flour) and optionally granulating the pelletized pulse product to form granulated pulse product (e.g., granulated pulse flour).

Some embodiments comprise adding the pulse product (optionally, pelletized or in flour form) to a beverage to provide a product composition. For example, the beverage can be selected from the group consisting of fruit juices, dairy beverages, and carbonated soft drinks. Furthermore, the pulse product can be added to the beverage to provide the product composition with, for example, 1 to 25% soluble fiber and/or 1 to 25% protein based on total weight of the product composition. Although a wide range has been given, as with the other ranges given herein, any smaller range (e.g., 2-3%, 12-15%, etc.) contained within the larger range can also be achieved and is considered to be an additional embodiment disclosed herein. As an example, the smaller values of a pulse content range can be useful for a beverage that is intended to have a lower viscosity, yet nonetheless provide benefits of adding a pulse product (e.g., soluble fiber) to the beverage. Meanwhile, a higher end of the pulse content range can be useful for providing substantial pulse-related benefits while still having a low enough viscosity to be drinkable as a beverage.

Some embodiments comprise adding the pulse product to a mixture for a food product (e.g. to provide a product composition). For example, the food product can be selected from the group consisting of bars, cereals, puddings, smoothies, ice cream, cookies, and crackers.

Additionally, in some embodiments, the invention provides a method (e.g., for providing a pulse-and-grain product). For example, in some embodiments, the combining step comprises combining the at least a portion of pulse, at least a portion of grain, and the suitable enzyme to form the enzyme-pulse starting mixture. As an illustration, the enzyme-pulse starting mixture can be an enzyme-pulse-and-grain starting mixture. In some embodiments, the enzyme-pulse-and-grain starting mixture further comprises sugar (e.g., granulated sugar), at least one antioxidant, a maltodextrin, and/or any combination thereof.

As used herein, grain is generally used to refer to cereal grains and pulse is generally used to refer to legumes, beans, peas, etc. As examples, the pulse can be selected from the group consisting of peas, lentils, chickpeas, navy beans, black turtle beans, cranberry beans, kidney beans, pinto beans, small red beans, Dutch brown beans, pink beans, and any combination thereof. Furthermore, the grain can be selected, for example, from the group consisting of wheat, oat, barley, corn, white rice, brown rice, barley, millet, sorghum, rye, triticale, teff, spelt, buckwheat, *quinoa*, amaranth, kaniwa, cockscomb, green groat, and any combination thereof. Additionally, in some embodiments, the at least a portion of pulse is pulse flour (e.g., whole pulse flour) and/or the at least a portion of grain is grain flour (e.g., whole grain flour).

In some embodiments the enzyme-pulse-and-grain starting mixture comprises: a mass ratio of sugar (e.g., granulated sugar) to the combined pulse flour and grain flour from about 0.03 to about 0.3, optionally 0.03 to 0.15; a mass ratio of maltodextrin to the combined pulse flour and grain flour from about 0 to about 0.3, optionally 0.03 to 0.15; and an effective amount of at least one antioxidant. Furthermore, in some embodiments, a pulse starting mixture comprises the at least a portion of pulse; a grain starting mixture comprises the at least a portion of grain; and the pulse starting mixture and the grain starting mixture are combined with the suitable enzyme to form the enzyme-pulse-and-grain starting mixture. As an example, the pulse starting mixture can comprise at least about 90% by weight whole pulse flour, or the pulse starting mixture can comprise about 90 to about 99.5%, or about 90 to about 95% by weight whole pulse flour.

In some embodiments, the heating step comprises heating the enzyme-pulse-and-grain starting mixture to between about 120° F. (48.89° C.) and about 200° F. (93.33° C.) to begin to hydrolyze the starch (e.g., starch molecules), thereby providing a heated pulse-and-grain mixture. In some embodiments, during the heating the enzyme-pulse-and-grain starting mixture is heated to at least about 140° F. (60° C.), 180° F. (82.22° C.), 200° F. (93.33° C.), or 212° F. (100° C.), or about 140° F. (60° C.) to about 212° F. (100° C.), or about 140° F. (60° C.) to about 180° F. (82.22° C.).

Furthermore, in some embodiments, the extruding step comprises extruding the heated pulse-and-grain mixture to continue hydrolyzing the starch and further to gelatinize and cook the heated pulse-and-grain mixture thereby providing a pulse-and-grain product (e.g., at least a portion of pulse) comprising gelatinized, hydrolyzed starch. In some embodiments, the extruding occurs at a barrel temperature of about 140° F. (60° C.) to about 350° F. (176.67° C.), or about 140° F. (60° C.) to about 320° F. (160° C.), or about 140° F. (60° C.) to about 250° F. (121.11° C.). Additionally, in some embodiments, during the extruding the heated pulse-and-grain mixture is heated to a temperature of about 212° F. (100° C.) to about 260° F. (126.67° C.).

Some embodiments further comprise pelletizing the pulse-and-grain product to form pelletized pulse-and-grain product (e.g., pulse-and-grain pellets or pulse-and-grain flour), and optionally granulating the pelletized pulse-and-grain product to form granulated pulse-and-grain product (e.g., granulated pulse-and-grain flour).

Some embodiments comprise adding the pulse-and-grain product to a beverage to provide a product composition. For example, the beverage can be selected from the group consisting of fruit juices, dairy beverages, and carbonated soft drinks. Furthermore, the pulse-and-grain product can be added to the beverage to provide the product composition with 1 to 25% soluble fiber based on total weight of the product composition. As an example, the smaller values of the range can be useful for a beverage that is intended to have a lower viscosity, yet nonetheless provide benefits of adding a pulse product (e.g., soluble fiber) to the beverage. Meanwhile, a higher end of the range can be useful for providing substantial pulse-related benefits while still having a low enough viscosity to be drinkable as a beverage.

Some embodiments comprise adding the pulse-and-grain product to a mixture for a food product (e.g., to provide a product composition). For example, the food product can be selected from the group consisting of bars, cereals, puddings, smoothies, ice cream, cookies, and crackers.

In some embodiments, the invention provides a composition comprising at least a portion of pulse (e.g., whole pulse, whole pulse flour, extruded whole pulse flour), and the at least a portion of pulse comprises gelatinized, hydrolyzed starch. For example, the at least a portion of pulse can be made by hydrolyzing starch in whole pulse. The composition can further comprise, for example, deactivated amylase enzyme (e.g., α-amylase enzyme), and/or water. For example, in some embodiments, the composition comprises at least 80 wt. % water. The water can come from a water-based liquid such as pure water, milk, fruit juice, etc.

In some embodiments, the composition comprises at least about 3.0 wt. % of the at least a portion of pulse (e.g., whole pulse flour), which can provide mouthfeel benefits (e.g., less viscosity) over a composition with a non-hydrolyzed pulse flour at the same concentration. For example, a composition (e.g., food product) comprising at least 3.0 wt. % non-hydrolyzed pulse flour can result in noticeable mouthfeel effects (e.g., increase in viscosity) in the composition if the composition has a liquid phase (e.g., food product, such as soup or beverage).

Additionally, in some embodiments, the composition comprises at least about 10 wt. % of the at least a portion of pulse (e.g., whole pulse flour), which can provide mouthfeel benefits (e.g., less viscosity) over a composition with a non-hydrolyzed pulse flour at the same concentration. For example, a composition (e.g., food product) comprising at least 10 wt. % non-hydrolyzed pulse flour can have an undesirable mouthfeel (e.g., undesirably high viscosity) for some consumers in some applications if the composition has a liquid phase (e.g., food product, such as soup or beverage).

Furthermore, in some embodiments, the composition comprises about 3.3 wt. % to about 6.6 wt. % of the at least a portion of pulse (e.g., whole pulse flour), and, optionally, the composition is a beverage. Additionally, in some embodiments, a composition comprises grain (e.g., cereal grains) and pulse at a mass ratio of about 1:1. This can be useful, for example, to provide a composition with certain desirable attributes. As an illustration, it can be desirable to provide a certain amount of whole grain (e.g., about 3.3 wt. % to about 6.6 wt. %) to provide a desired amount of soluble fiber. It can also be desirable to provide a certain quantity and quality of protein. While the grain can provide the desired amount of soluble fiber by itself, it can fail to provide the desired protein quality. For example, certain cereal grains (e.g., oat grain) have a protein digestibility-corrected amino acid score ("PDCAAS") that is less than 1.0. This occurs, for example, because oat grain comprises insufficient lysine even though it has more than sufficient methionine. The problem can be addressed by combining oat grain with yellow peas and/or pinto beans, even though they also have a PDCAAS score of less than 1.0. The combination is useful because, while yellow peas and/or pinto beans comprise insufficient methionine, they have more than sufficient amounts of lysine to make up for the deficiency in oat grain. Accordingly, oat grain can be combined with yellow peas and/or pinto beans at a mass ratio of about 1:1 to provide a combined PDCAAS score that is greater than the PDCAAS score of the individual components.

In some embodiments the at least a portion of pulse in the composition comprises (or optionally, consists of) whole pulse selected from the group consisting of peas, lentils, chickpeas, navy beans, black turtle beans, cranberry beans, kidney beans, pinto beans, small red beans, Dutch brown beans, pink beans and combinations thereof.

In some embodiments, the at least a portion of pulse can be hydrolyzed-starch whole pulse (e.g., beans, peas, chickpeas, etc.) comprising gelatinized, hydrolyzed starch. Furthermore, the hydrolyzed-starch whole pulse can have, within a tolerance of +/−20%, 15%, 10%, 5%, 2% or 1%, at least one mass ratio selected from the group consisting of: (i) a mass ratio of starch to protein equal to a mass ratio of starch to protein of unhydrolyzed whole pulse (e.g., whole pulse comprising gelatinized, unhydrolyzed starch) equivalent in kind (for example, species, subspecies, variety, or plurality of species, subspecies, or varieties) and condition (for example, ripeness, lack of rottenness, level of processing (e.g., harvesting, threshing, grinding, milling, cracking, flaking, separation to remove non-pulse components, steaming, rolling, cutting)) to the hydrolyzed-starch whole pulse; (ii) a mass ratio of fat to protein equal to a mass ratio of fat to protein of unhydrolyzed whole pulse equivalent in kind and condition to the hydrolyzed-starch whole pulse; (iii) a mass ratio of dietary fiber to protein equal to a mass ratio of dietary fiber to protein of unhydrolyzed whole pulse equivalent in kind and condition to the hydrolyzed-starch whole pulse; and (iv) any combination thereof.

Furthermore, the at least a portion of pulse can comprise whole pulse. For example, the composition can comprise about 90 to 99.94 wt. % whole pulse on a dry basis, at least about 90, 95, 96, 97, 98, 99, 99.94 wt. % whole pulse on a dry basis, or any range formed by values contained within the listed ranges up to 100 wt. %. Furthermore, in some embodiments, the at least a portion of pulse can comprise each component in an original set of components (e.g., comprising starch and protein) at an original mass ratio relative to protein within a tolerance of +/−20%, 15%, 10%, 5%, 2% or 1%. For example, the original mass ratio can be the mass ratio of each component relative to protein at a time of harvesting, although it can also be at another reference time, for example, before processes including separation of the anatomical components of the whole pulse, grinding, cooking, gelatinization of the starch in the whole pulse, hydrolysis of the starch in the whole pulse, and/or any combination thereof.

In some embodiments, the composition comprising the at least a portion of pulse is a first composition with a viscosity at 25° C. (e.g., an RVA viscosity at 25° C.) that is at most 75%, 70%, 60%, 50%, 40%, 30%, 20%, 10% or 5%, or equal to about 75-5%, 75-10%, 70-20% (or any range contained in the listed ranges) of a viscosity at 25° C. (e.g., an RVA viscosity at 25° C.) of a second composition that is equivalent to the first composition except that the second composition comprises gelatinized, unhydrolyzed starch in place of gelatinized, hydrolyzed starch. Additionally, although specific ranges have been discussed, for example, 75% to any smaller reasonable value (e.g., a value greater than zero because viscosity will be greater than zero), additional embodiments can be formed by any range contained within the previously mentioned ranges (e.g. 64% to 3%). This is also true of the other ranges discussed herein, as a skilled person would understand after reading this disclosure.

Additionally, in some embodiments, the viscosity (e.g., RVA viscosity at 25° C. or peak RVA viscosity) of a composition (e.g., before or after hydrolysis, as applicable) is equal to any viscosity (e.g., RVA viscosity at 25° C. or peak RVA viscosity, respectively) for a composition (e.g., before or after hydrolysis, as applicable) described herein (e.g., in the tables or elsewhere), or any viscosity range whose endpoints are selected from values described herein. Furthermore, in some embodiments, the viscosity of a composition after hydrolysis can be any value between a value before hydrolysis and a value obtained after a certain degree of hydrolysis. For example, in light of the present specification, a skilled person would understand that the degree of hydrolysis can be adjusted using factors such as temperature, time, moisture level, enzyme level, and other factors, which can in turn be used to adjust the viscosity of a composition after hydrolysis.

In some embodiments, the composition is a first composition comprising a viscosity at 25° C. (e.g., an RVA viscosity at 25° C.) that is at most 75%, 70%, 60%, 50%, 40%, 30%, 20%, 10%, or 5% or equal to about 75-5%, 75-10%, 70-20% (or any range contained in the listed ranges) of a viscosity at 25° C. (e.g., an RVA viscosity at 25° C.) of a second composition. For example, the first composition can consist of each ingredient in a first set of ingredients at a specified weight percentage, and the first set of ingredients can comprise the at least a portion of pulse and water. Furthermore, the second composition can consist of the first set of ingredients in the specified weight percentages, except that the at least a portion of pulse comprising gelatinized, hydrolyzed starch is replaced with at least a portion of pulse comprising gelatinized, unhydrolyzed starch.

In some embodiments, the invention provides a composition comprising at least a portion of grain (e.g., starchy endosperm, germ, bran, whole grain, or whole grain flour), and the at least a portion of grain comprises gelatinized, hydrolyzed starch. For example, the at least a portion of grain can be made by hydrolyzing starch in whole grain. The composition can further comprise, for example, deactivated amylase enzyme (e.g., α-amylase), and/or water. For example, in some embodiments, the composition comprises at least 80 wt. % water. The water can come from a water-based liquid such as pure water, milk, fruit juice, etc.

In some embodiments, the composition comprises at least about 1 wt. % of the at least a portion of grain (e.g., whole grain flour), which can provide mouthfeel benefits (e.g., less viscosity) over a composition with a non-hydrolyzed grain flour at the same concentration. As an illustration, a composition (e.g., food product) comprising at least 1 wt. % non-hydrolyzed grain flour can result in noticeable mouthfeel effects (e.g., increase in viscosity) in the composition if the composition has a liquid phase (e.g., food product, such as soup or beverage).

Additionally, in some embodiments, the composition comprises about 6.6 wt. % to about 15 wt. % of the at least a portion of grain (e.g., whole grain flour), about 6.6 wt. % to about 12 wt. %, or about 12 wt. % to about 15 wt. %), which can provide mouthfeel benefits (e.g., less viscosity) over a composition with a non-hydrolyzed grain flour at the same concentration. For example, for some consumers, a composition (e.g., food product) comprising at least 6.6 wt. % non-hydrolyzed grain flour can have an undesirable mouthfeel (e.g., undesirably high viscosity) if the composition has a liquid phase (e.g., food product, such as soup or beverage).

Furthermore, in some embodiments, the composition comprises about 3.3 wt. % to about 6.6 wt. % of the at least a portion of grain (e.g., whole pulse flour). Additionally, in some embodiments, a composition comprises grain (e.g., cereal grains) and pulse at a mass ratio of about 1:1. This can be useful, for example, to provide a composition with certain desirable attributes, such as fiber content and protein quality, as described herein.

In some embodiments, the at least a portion of grain is an extruded whole grain flour.

In some embodiments, the composition comprises at least about 90, 95, 96, 97, 98, 99, or 99.94 wt. % a combination of whole pulse flour and whole grain flour on a dry basis. Furthermore, in some embodiments, the composition comprises at least about 90 to 99.94 wt. % a combination of whole pulse flour and whole grain flour on a dry basis. The composition can also comprise a combination of whole pulse flour and whole grain flour in an amount given by any range formed using values contained within the listed ranges.

In some embodiments, the at least a portion of grain comprises whole grain selected from the group consisting of wheat, oat, barley, corn, white rice, brown rice, barley, millet, sorghum, rye, triticale, teff, spelt, buckwheat, *quinoa*, amaranth, kaniwa, cockscomb, green groat (e.g., dehulled oats that are not heat treated by kilning or otherwise) and combinations thereof.

In some embodiments, the at least a portion of grain can be hydrolyzed-starch bran (e.g., oat bran, rice bran, wheat bran, sorghum bran, etc.) comprising gelatinized, hydrolyzed starch. Furthermore, the hydrolyzed-starch bran can have, within a tolerance of +/−20%, 15%, 10%, 5%, 2% or 1%, at least one mass ratio selected from the group consisting of: (i) a mass ratio of starch to protein equal to a mass ratio of starch to protein of unhydrolyzed bran (e.g., bran comprising gelatinized, unhydrolyzed starch) equivalent in kind (for example, species or recognized subspecies or plurality of species or plurality of recognized subspecies) and condition (for example, ripeness, lack of rottenness, level of processing (e.g., harvesting, threshing, grinding, milling, cracking, flaking, separation to remove non-grain components, steaming, rolling, cutting)) to the hydrolyzed-starch bran; (ii) a mass ratio of fat to protein equal to a mass ratio of fat to protein of unhydrolyzed bran equivalent in kind and condition to the hydrolyzed-starch bran; (iii) a mass ratio of dietary fiber to protein equal to a mass ratio of dietary fiber to protein of unhydrolyzed bran equivalent in kind and condition to the hydrolyzed-starch bran; and (iv) any combination thereof.

In some embodiments of the composition comprising hydrolyzed-starch bran, the hydrolyzed-starch bran is oat bran. Furthermore, the oat bran can comprise: at least about 5.5 wt. % beta-glucan on a total dry weight basis (e.g., after removing any water by dehydrating); and at least about 16.0 wt. % dietary fiber on a total dry weight basis. Additionally, at least one-third of the total dietary fiber can be soluble fiber. For example, this is consistent with the 1989 AACC definition of oat bran, which states: "Oat Bran is the food which is produced by grinding clean oat groats or rolled oats and separating the resulting oat flour by sieving bolting, and/or other suitable means into fractions such that the oat bran fraction is not more than 50% of the original starting material and has a total betaglucan content of at least 5.5% (dry-weight basis) and a total dietary fiber content of at least 16.0% (dry-weight basis), and such that at least one-third of the total dietary fiber is soluble fiber." (See AACC International's Definition of "Oat Bran," approved in 1989, available at http://www.aaccnet.org/initiatives/definitions/pages/wholegrain.aspx (last accessed Feb. 11, 2016).)

In some embodiments of a composition comprising at least a portion of grain, the at least a portion of grain is hydrolyzed-starch whole grain (e.g., oat, rice, wheat, sorghum, etc.) comprising gelatinized, hydrolyzed starch. Furthermore, the hydrolyzed-starch whole grain can have, within a tolerance of +/−20%, 15%, 10%, 5%, 2% or 1%) at least one mass ratio selected from the group consisting of: (i) a mass ratio of starch to protein equal to a mass ratio of starch to protein of unhydrolyzed whole grain equivalent in kind and condition to the hydrolyzed-starch whole grain; (ii) a mass ratio of fat to protein equal to a mass ratio of fat to protein of unhydrolyzed whole grain equivalent in kind and condition to the hydrolyzed-starch whole grain; (iii) a mass ratio of dietary fiber to protein equal to a mass ratio of dietary fiber to protein of unhydrolyzed whole grain equivalent in kind and condition to the hydrolyzed-starch whole grain; and (iv) any combination thereof. For example, in some embodiments, if alpha-amylase is used to catalyze the hydrolysis of starch, then the starch will by hydrolyzed, but not protein, fat or fiber. Accordingly, the mass ratio of any one component (protein, fat, dietary fiber, sugar) to another component in at least a portion of pulse and/or grain can remain unchanged or substantially or essentially unchanged unless the mass ratio involves starch. Furthermore, assuming that the mass of starch is unchanged (e.g., because the hydrolysis is controlled and stopped before starch is converted to monosaccharides, disaccharides, simple sugars, and/or non-starch molecules), then the mass ratio of starch to other components will also remain unchanged or substantially or essentially unchanged. Accordingly, a small tolerance can be achieved for the change in the mass ratios of any one component relative to another component (e.g., protein) in at least a portion of pulse and/or grain. Nonetheless, larger tolerances can also be obtained, where desired, or where smaller tolerances are not necessary or as relatively important for a particular application.

As an example of the various ratios of some components in whole grain to other components in whole grain, Table 6 below shows the proximate constituents of whole grain as compiled from USDA data. As an illustration, this data was used to calculate the ratios of the various components, with the results being shown in Table 7.

TABLE 6

Proximate constituents of whole grains (USDA data)

|  | oatmeal | wheat | brown rice | rye | barley | sorghum |
|---|---|---|---|---|---|---|
| Water, wt. % | 8.5 | 12 | 12.2 | 13 | 10.3 | 11.6 |
| Carbohydrate, wt. % | 58.7 | 60.2 | 73.9 | 58.7 | 69.7 | 65.6 |
| Protein, wt. % | 14 | 13.5 | 7.4 | 11.2 | 9.2 | 11 |
| Fat, wt. % | 8 | 2.1 | 2.8 | 2.3 | 1.6 | 3.3 |
| Dietary fiber, wt. % | 9 | 10.6 | 2.3 | 12.8 | 8 | 6.9 |
| Ash, wt. % | 1.8 | 1.6 | 1.4 | 2 | 1.2 | 1.6 |
| Total, wt. % | 100 | 100 | 100 | 100 | 100 | 100 |

TABLE 7

Ratio of components to protein for whole grains (USDA data)

|  | oatmeal | wheat | brown rice | rye | barley | sorghum |
|---|---|---|---|---|---|---|
| Water, g | 0.61 | 0.89 | 1.65 | 1.16 | 1.12 | 1.05 |
| Carbohydrate, g | 4.19 | 4.46 | 9.99 | 5.24 | 7.58 | 5.96 |
| Protein, g | 1.00 | 1.00 | 1.00 | 1.00 | 1.00 | 1.00 |
| Fat, g | 0.57 | 0.16 | 0.38 | 0.21 | 0.17 | 0.30 |
| Dietary fiber, g | 0.64 | 0.79 | 0.31 | 1.14 | 0.87 | 0.63 |
| Ash, g | 0.13 | 0.12 | 0.19 | 0.18 | 0.13 | 0.15 |

Although these ratios of components (e.g., macronutrients) are shown for a whole grain composition with unhydrolyzed starch, the ratios can remain unchanged or substantially or essentially unchanged as starch is subject to controlled hydrolysis as described herein. Furthermore, several Tables herein show examples of various compositions subject to controlled hydrolysis under listed extrusion conditions.

In some embodiments, the at least a portion of grain comprises whole grain. For example, the composition can comprise about 90 to 99.94 wt. % whole grain on a dry basis, at least about 90, 95, 96, 97, 98, 99, 99.94 wt. % whole grain on a dry basis, or any range formed by values contained within the listed ranges. Furthermore, in some embodiments, the whole grain can comprise each component in an original set of components (e.g., comprising starch, fat, dietary fiber, and protein) at an original mass ratio relative to protein within a tolerance of +/−20%, 15%, 10%, 5%, 2% or 1%. For example, the original mass ratio can be the mass ratio of each component relative to protein at a time of harvesting, although it can also be at another reference time, for example, before processes including separation of the anatomical components of the whole grain, grinding, cooking, gelatinization of the starch in the whole grain, hydrolysis of the starch in the whole grain, and/or any combination thereof.

In some embodiments, the at least a portion of grain is hydrolyzed-starch whole grain (e.g., whole grain flour ground from a whole grain); the at least a portion of grain comprises caryopses (e.g., intact, ground, cracked, or flaked); and the caryopses comprise principal anatomical components consisting of starchy endosperm, germ, and bran. For example, the composition can comprise about 90 to 99.94 wt. % hydrolyzed-starch whole grain on a dry basis, at least about 90, 95, 96, 97, 98, 99, 99.94 wt. % hydrolyzed-starch whole grain on a dry basis, or any range formed by values contained within the listed ranges. Furthermore, in some embodiments, the hydrolyzed-starch whole grain has within a tolerance of +/−20% (optionally, 15%, 10%, 5%, 2% or 1%) at least one mass ratio selected from the group consisting of: (i) a mass ratio of germ to endosperm equivalent to a mass ratio of germ to endosperm of unhydrolyzed intact caryopses of the same kind and condition as the caryopses of the hydrolyzed-starch whole grain; (ii) a mass ratio of bran to endosperm equivalent to a mass ratio of bran to endosperm of unhydrolyzed intact caryopses of the same kind and condition as the caryopses of the hydrolyzed-starch whole grain; and (iii) any combination thereof.

In some embodiments, the composition is a first composition comprising a viscosity at 25° C. (e.g., an RVA viscosity at 25° C.) that is at most (e.g., no more than) 75%, 70%, 60%, 50%, 40%, 30%, 20%, 10%, or 5% or equal to about 75-5%, 75-10%, 70-20% (or any range contained in the listed ranges) of a viscosity at 25° C. (e.g., an RVA viscosity at 25° C.) of a viscosity at 25° C. of a second composition that is equivalent to the first composition except that the second composition comprises gelatinized, unhydrolyzed starch in place of gelatinized, hydrolyzed starch.

Tables 8-19 provide examples of compositions with various characteristics (e.g., reduced viscosity) as a result of certain listed extrusion conditions. For example, Table 8 shows a portion of grain, namely oat bran concentrate, before and after extrusion under various extrusion conditions. As can be seen, extruding oat bran concentrate without enzyme catalyzed hydrolysis resulted in some reduction in the RVA peak viscosity of the oat bran concentrate from 7,879 cP to 6,692 cP. However, extrusion with enzyme-catalyzed hydrolysis resulted in greater reduction in the RVA peak viscosity, namely, to 3,028 cP and 2,806 cP, depending on the enzyme concentration. It is worthwhile to point out that the viscosity of the dough can affect the pressure and temperature of the dough within the extruder. For example, greater viscosity can result in greater friction-related temperature increases. Similarly, if pressure is measured at one point, a more viscous composition can result in greater pressure at the same point, as a result of frictional pressure loss as the composition is conveyed. In Table 10, Table 14, and Table 18, pressure was measured at the exit end of the extruder screw. Furthermore, in some embodiments, the screw profiles employed build pressure throughout the screw and/or screws so that the exit end of the screw has the highest pressure. Although, some embodiments can have different screw profiles that result, for example, in pressure increasing and then decreasing along an extruder screw and/or screws.

With reference to the following Tables, it is also worthwhile to note that the listed values pertain to a composition comprising flour, water moisture, optionally tocopherol, and optionally enzyme, as indicated. Accordingly, the mass concentrations in the Tables (e.g., wt. %) are given as a fraction of the mass of the composition. Additionally, the moisture (i.e. water moisture including inherent and added water) in the following tables (e.g., Table 8) was generally determined by measuring the composition before and after dehydration and assuming that the difference in weight was caused by evaporation of water. As used in the following Tables, Below Quantifiable Limits ("BQL") is below 0.20 wt. % for mono- and di-saccharides.

TABLE 8

Oat Bran Concentrate, wt. % of component, with moisture

|  | Stream Description | | | |
|---|---|---|---|---|
| Component | 0 | 1 | 3 | 4 |
| Moisture (water) | 7.9 | 7.24 | 7.72 | 9.34 |
| Starch | 31.95 | 32.95 | 30.02 | 29.81 |
| Fat | 10.94 | 9.65 | 9.69 | 9.44 |
| Protein | 19.21 | 18.87 | 19.08 | 18.86 |
| Total Dietary Fiber ("TDF") | 25.2 | 24.9 | 26.2 | 24.6 |
| Insoluble Dietary Fiber ("IDF") | 21.6 | 15.2 | 19 | 15.6 |
| β-glucan | 11.52 | 11.61 | 12.3 | 12.03 |
| Total sugar | 2.43 | 2.4 | 2.07 | 2.57 |
| Maltose | BQL | BQL | BQL | 0.28 |

TABLE 9

Oat Bran Concentrate

| | wt. % of component, dry basis Stream Description | | | |
|---|---|---|---|---|
| Component | 0 | 1 | 3 | 4 |
| Moisture | 0 | 0 | 0 | 0 |
| Starch | 34.7 | 35.5 | 32.5 | 32.9 |
| Fat | 11.9 | 10.4 | 10.5 | 10.4 |
| Protein | 20.9 | 20.3 | 20.7 | 20.8 |
| Total Dietary Fiber ("TDF") | 27.4 | 26.8 | 28.4 | 27.1 |
| Insoluble Dietary Fiber ("IDF") | 23.5 | 16.4 | 20.6 | 17.2 |
| β-glucan | 12.5 | 12.5 | 13.3 | 13.3 |
| Total sugar | 2.6 | 2.6 | 2.2 | 2.8 |
| Maltose | BQL | BQL | BQL | 0.3 |
| β-glucan MW, Million Dalton | 1.35 | 1.39 | 1.31 | 1.25 |
| RVA peak viscosity, cP | 7879 | 6692 | 3028 | 2806 |

TABLE 10

Oat Bran Concentrate Extrusion Parameters

| | Stream Description | | | |
|---|---|---|---|---|
| Parameter | 0 | 1 | 3 | 4 |
| Type of extruder | N/A | ---Werner & Pfleiderer Extruder ZSK-58--- | | |
| Feed rate of flour, lb./hr. (kg/hr) ** | N/A | 320 (145.15) | 320 (145.15) | 320 (145.15) |
| Tocopherol, wt. % | N/A | 0.1 | 0.1 | 0.1 |
| Enzyme type | N/A | N/A | α | α |
| Enzyme amount, wt. % | N/A | N/A | 0.09 | 0.12 |
| Moisture at preconditioner exit/extruder inlet, wt. % | N/A | 33 | 34 | 34 |
| Dough temperature at preconditioner exit/extruder inlet (e.g., wet mix temperature ["WMT"]), ° F. (° C.) | N/A | 173 (78.33) | 175 (79.44) | 169 (76.11) |
| Extruder screw speed, RPM | N/A | 307 | 307 | 307 |
| Residence time, min | N/A | 1 | 1 | 1 |
| Pressure at exit end of extruder screw, PSI | N/A | 860 | 1072 | 1101 |
| Barrel temperature, ° F. (° C.) | N/A | T | T | T |
| Extruder die wall exit temperature, ° F. (° C.) | N/A | 325 (162.78) | 314 (156.67) | 312 (156.56) |

TABLE 11

Key for Tables 8-10

| | |
|---|---|
| * | not measured |
| BQL | below quantifiable level (present, if at all, at a level that is below detectable limits) |
| ** | The given feed rate in pounds (kilograms) per hour comprises flour, moisture, enzyme and tocopherol, as applicable. Although the mass concentration of flour (i.e., wt. % of flour) as a fraction of the feed rate is not explicitly given as It is for tocopherol, enzyme, and moisture (i.e., water) content, the mass concentration of the flour can be calculated by assuming the composition for which the feed rate is given consists of flour, moisture, and optionally tocopherol and/or enzyme, as indicated in the Tables. Accordingly, anything that is not moisture, tocopherol, and enzyme is deemed to be flour. |
| 0 | flour feed, unextruded, without tocopherol and without enzyme |
| 1 | flour extruded with tocopherol, but without enzyme |

TABLE 11-continued

Key for Tables 8-10

| | |
|---|---|
| 3 | flour extruded with tocopherol and with 0.09 wt. % α-amylase as percentage of total composition including α-amylase |
| 4 | flour extruded with tocopherol and with 0.12 wt. % α-amylase as percentage of total composition including α-amylase |
| N/A | not applicable |
| α | α-amylase |
| T | Temperature (+/−5° F. or 2.8° C.) in adjacent and sequentially ordered extruder barrel zones 1, 2, 3, 4, 5: 170° F. (76.67° C.), 200° F. (93.33° C.), 225° F. (107.22° C.), 275° F. (135° C.), 300° F. (148.89° C.), respectively |

TABLE 12

Chickpea Flour and Oat/Chickpea blend, wt. % of component, with moisture

| | Chickpea flour, 100 wt. % Stream Description | | | Oat/chickpea blend flour, 50/50 wt. % Stream Description | | |
|---|---|---|---|---|---|---|
| Component | 0 | 1 | 4 | 0 | 1 | 4 |
| Moisture (water) | 8.41 | 12.5 | * | 8.54 | 12.23 | 12.26 |
| Starch | 40.95 | 39.93 | * | 48.6 | 46.88 | 44.75 |
| Fat | 6.63 | 6.35 | * | 6.85 | 6.9 | 6.58 |
| Protein | 22.55 | 20.92 | * | 17.54 | 16.13 | 16.52 |
| Total Dietary Fiber ("TDF") | 8.5 | 11 | * | 10.2 | 8.5 | 9.3 |
| Insoluble Dietary Fiber ("IDF") | 8 | 7.4 | * | 8.1 | 6.3 | 7.2 |
| β-glucan | BQL | BQL | * | 1.77 | 2.02 | 1.95 |
| Total sugar | 2.88 | 3.06 | * | 2.38 | 2 | 1.78 |

TABLE 13

Chickpea Flour and Oat/Chickpea blend, wt. % of component, dry basis

| | Chickpea flour, 100 wt. % Stream Description | | | Oat/chickpea blend flour, 50/50 wt. % Stream Description | | |
|---|---|---|---|---|---|---|
| Component | 0 | 1 | 4 | 0 | 1 | 4 |
| Moisture (water) | 0 | 0 | * | 0 | 0 | 0 |
| Starch | 44.7 | 45.6 | * | 53.1 | 53.4 | 51.0 |
| Fat | 7.2 | 7.3 | * | 7.5 | 7.9 | 7.5 |
| Protein | 24.6 | 23.9 | * | 19.2 | 18.4 | 18.8 |
| Total Dietary Fiber ("TDF") | 9.3 | 12.6 | * | 11.2 | 9.7 | 10.6 |
| Insoluble Dietary Fiber ("IDF") | 8.7 | 8.5 | * | 8.9 | 7.2 | 8.2 |
| β-glucan | * | * | * | 1.9 | 2.3 | 2.2 |
| Total sugar | 3.1 | 3.5 | * | 2.6 | 2.3 | 2.0 |
| RVA peak viscosity, CP | 2439 | 1785 | * | 4753 | 2227 | 1043 |

TABLE 14

Chickpea Flour and Oat/Chickpea Blend Extrusion Parameters

| Parameter | Chickpea flour, 100 wt. % Stream Description | | | Oat/Chickpea blend flour, 50/50 wt. % Stream Description | | |
|---|---|---|---|---|---|---|
| | 0 | 1 | 4 | 0 | 1 | 4 |
| Type of extruder | N/A | E | E | N/A | E | E |
| Feed rate of flour, lb/hr (kg/hr)** | N/A | 320 (145.15) | * | N/A | 320 (145.15) | 320 (145.15) |
| Tocopherol, wt. % | N/A | 0.1 | * | N/A | 0.1 | 0.1 |
| Enzyme type | N/A | N/A | * | N/A | N/A | α |
| Enzyme amount, wt. % | N/A | N/A | * | N/A | N/A | 0.12 |
| Moisture at preconditioner exit/extruder inlet, wt. % | N/A | 32 | * | N/A | 33 | 33 |
| Dough temperature at preconditioner exit/extruder inlet (e.g., WMT), °F. (°C.) | N/A | 169 (76.11) | * | N/A | 169 (76.11) | 176 (80) |
| Extruder screw speed, RPM | N/A | 318 | * | N/A | 318 | 318 |
| Residence time, min | N/A | 1 | * | N/A | 1 | 1 |
| Pressure at exit end of extruder screw, PSI | N/A | 365 | * | N/A | 437 | 260 |
| Barrel temperature, °F. (°C.) | N/A | T | * | N/A | T | T |
| Extruder die wall exit temperature, °F. (°C.) | N/A | 309 (153.89) | * | N/A | 302 (150) | 300 (148.89) |

TABLE 15

Key for Tables 12-14

| | |
|---|---|
| * | not measured |
| ** | The given feed rate in pounds (kilograms) per hour comprises flour, moisture, enzyme and tocopherol, as applicable. Although the mass concentration of flour (i.e., wt. % of flour) as a fraction of the feed rate is not explicitly given as It is for tocopherol, enzyme, and moisture (i.e., water) content, the mass concentration of the flour can be calculated by assuming the composition for which the feed rate is given consists of flour, moisture, and optionally tocopherol and/or enzyme, as indicated in the Tables. Accordingly, anything that is not moisture, tocopherol, and enzyme is deemed to be flour. |
| E | Werner & Pfleiderer Extruder ZSK-58 |
| 0 | flour feed, unextruded, without tocopherol and without enzyme |
| 1 | flour extruded with tocopherol, but without enzyme |
| 4 | flour extruded with tocopherol and with 0.12 wt. % α-amylase as percentage of total composition including α-amylase |
| BQL | below quantifiable level (present, if at all, at a level that is below detectable limits) |
| N/A | not applicable |
| α | α-amylase |
| T | Temperature (+/−5° F. or 2.8° C.) in adjacent and sequentially ordered extruder barrel zones 1, 2, 3, 4, 5: 170° F. (76.67° C.), 200° F. (93.33° C.), 225° F. (107.22° C.), 275° F. (135° C.), 300° F. (148.89° C.), respectively |

TABLE 16

Chickpea Flour and Brown Rice/Chickpea blend, wt. % of component, with moisture *

| Component | Chickpea flour, 100 wt. % Stream Description | | | Brown Rice/chickpea blend flour, 50/50 wt. % Stream Description | | |
|---|---|---|---|---|---|---|
| | 0 | 1 | 4 | 0 | 1 | 4 |
| Moisture (water) | 9.27 | 11.4 | 11 | 10.2 | 10.6 | 10.6 |
| Starch | 41.5 | 40.1 | 40.8 | 56.2 | 55.7 | 55.7 |
| Fat | 5.78 | 5.79 | 5.88 | 4.9 | 5.05 | 4.95 |
| Protein | 21.9 | 21.1 | 21.4 | 14.2 | 14.6 | 14.2 |
| Total Dietary Fiber ("TDF") | 8.3 | 7.6 | 8 | 5.8 | 5.6 | 5.9 |
| Total sugar | 2.5 | 2.4 | 2.6 | 2.2 | 2.1 | 2.2 |

TABLE 17

Chickpea Flour and Brown Rice/Chickpea blend, wt. % of component, dry basis

| Component | Chickpea flour, 100 wt. % Stream Description | | | Brown Rice/chickpea blend flour, 50/50 wt. % Stream Description | | |
|---|---|---|---|---|---|---|
| | 0 | 1 | 4 | 0 | 1 | 4 |
| Moisture (water) | 0 | 0 | 0 | 0 | 0 | 0 |
| Starch | 45.7 | 45.3 | 45.8 | 62.6 | 62.3 | 62.3 |
| Fat | 6.4 | 6.5 | 6.6 | 5.5 | 5.6 | 5.5 |
| Protein | 24.1 | 23.8 | 24.0 | 15.8 | 16.3 | 15.9 |
| Total Dietary Fiber ("TDF") | 9.1 | 8.6 | 9.0 | 6.5 | 6.3 | 6.6 |
| Total sugar | 2.8 | 2.7 | 2.9 | 2.4 | 2.3 | 2.5 |
| RVA peak viscosity, CP | 2428 | 1590 | 890 | 4110 | 1058 | 700 |
| Starch Avg. MW, Da | 1.95E+08 | 2.23E+07 | 1.37E+07 | 2.79E+08 | 3.42E+07 | 2.40E+07 |

TABLE 18

Chickpea Flour and Oat/Chickpea Blend Extrusion Parameters

| Parameter | Chickpea flour, 100 wt. % Stream Description | | | Oat/chickpea blend flour, 50/50 wt. % Stream Description | | |
|---|---|---|---|---|---|---|
| | 0 | 1 | 4 | 0 | 1 | 4 |
| Type of extruder | N/A | E | E | N/A | E | E |
| Feed rate of flour, lb/hr (kg/hr)** | N/A | 320 (145.15) | 320 (145.15) | N/A | 320 (145.15) | 320 (145.15) |
| Tocopherol, wt. % | N/A | 0.1 | 0.1 | N/A | 0.1 | 0.1 |
| Enzyme type | N/A | N/A | α | N/A | N/A | α |
| Enzyme amount, wt. % | N/A | N/A | 0.12 | N/A | N/A | 0.1 |
| Moisture at pre-conditioner exit/ extruder inlet, wt. % | N/A | 31 | 30 | N/A | 32 | 30 |
| Dough temperature at pre-conditioner exit/ extruder inlet (e.g., WMT), ° F. (° C.) | N/A | 172 (77.78) | 167 (75.00) | N/A | 171 (72.22) | 173 (78.33) |
| Extruder screw speed, RPM | N/A | 338 | 348 | N/A | 338 | 348 |
| Residence time, min | N/A | 1 | 1 | N/A | 1 | 1 |
| Pressure at exit end of extruder screw, PSI | N/A | 1504 | 1388 | N/A | 1446 | 1645 |
| Barrel temperature, ° F. (° C.) | N/A | T | T | N/A | T | T |
| Extruder die wall exit temperature, ° F. (° C.) | N/A | 290 (143.33) | 286 (141.11) | N/A | 287 (141.67) | 285 (140.56) |

TABLE 19

Key for Tables 16-18

| E | Werner & Pfleiderer Extruder ZSK-58 |
|---|---|
| * | Values do not add to 100 wt. % because, for example, certain components (e.g., ash) are not listed |
| 0 | flour feed, unextruded, without tocopherol and without enzyme |
| 1 | flour extruded with tocopherol, but without enzyme |
| 4 | flour extruded with tocopherol and with 0.12 wt. % α-amylase as percentage of total composition including α-amylase |
| BQL | below quantifiable level (not present or present at a level that is below detectable limits) |
| N/A | not applicable |
| α | α-amylase |
| T | Temperature (+/−5° F. or 2.8° C.) in adjacent and sequentially ordered extruder barrel zones 1, 2, 3, 4, 5: 170° F. (76.67° C.), 200° F. (93.33° C.), 225° F. (107.22° C.), 275° F. (135° C.), 300° F. (148.89° C.), respectively |

The Rapid Visco Analyzer ("RVA") peak viscosity of the compositions in Tables 9, 13, and 17 was measured using the following protocol. First, a mixture was formed consisting of a composition comprising at least a portion of pulse and/or grain, a specified wt. % tocopherol, a specified weight percentage of deactivated α-amylase, and a remainder of water. Water was added in an amount to provide the mixture with 14.3 wt. % solids. In other words, if the mixture were completely dehydrated by evaporating away the moisture, 14.3 wt. % solids would remain.

Second, the mixture was mixed by turning a shaft with a paddle at 500 rpm (for 5 seconds) until the composition, the tocopherol, and the deactivated α-amylase have absorbed an equilibrium amount of the water and are fully dispersed in the water to form the dispersion (e.g., generally homogeneous mixture, and to avoid clumps that can cause viscosity measurement errors).

Third, the dispersion was continuously mixed by turning a shaft with a paddle at 160 rpm and the viscosity of the dispersion was continuously measured while subjecting the dispersion to the following temperature profile: (i) holding the dispersion at about 25° C. for about 2 min; (ii) heating the dispersion to about 95° C. over about 5 minutes; (iii) holding the dispersion at about 95° C. for about 3 minutes; (iv) cooling the dispersion from about 95° C. to about 25° C. over about 5 minutes; (v) holding the dispersion at about 25° C. for about 3 min. The RVA peak viscosity was the maximum viscosity measured during steps (ii) and (iii).

Using a method such as the RVA peak viscosity measurement protocol can be useful, for example, to provide a way to compare the viscosity of compositions that are consumed after their starch has been gelatinized. This is so because the RVA peak viscosity measurement protocol involves heating and hydrating the composition, which gelatinizes starch in the composition if the starch has not already been gelatinized.

In some embodiments, the composition is a first composition comprising a viscosity at 25° C. (e.g., an RVA viscosity at 25° C.) that is at most 75%, 70%, 60%, 50%, 40%, 30%, 20%, 10%, or 5% or equal to about 75-5%, 75-10%, 70-20% (or any range contained in the listed ranges) of a viscosity at 25° C. (e.g., an RVA viscosity at 25° C.) of a second composition. For example, the first composition can consist of each ingredient in a first set of ingredients at a specified weight percentage, and the first set of ingredients can comprise the at least a portion of pulse, the at least a portion of grain, and water. Furthermore, the second composition can consist of the first set of ingredients in the specified weight percentages, except that the at least a portion of pulse comprising gelatinized, hydrolyzed starch is replaced with at least a portion of pulse comprising gelatinized, unhydrolyzed starch, and except that the at least a portion of grain comprising gelatinized, hydrolyzed starch is replaced with at least a portion of grain comprising gelatinized, unhydrolyzed starch.

In some embodiments, the average molecular weight of the gelatinized, hydrolyzed starch molecules in the composition is a fraction of the molecular weight of gelatinized, unhydrolyzed starch molecules equivalent (e.g., in kind and condition) to the gelatinized, hydrolyzed starch molecules, except that the gelatinized, unhydrolyzed starch molecules have not been hydrolyzed. For example, the fraction can be selected from the group consisting of about 0.90 to 0.47, 0.80 to 0.47, 0.70 to 0.47, 0.60 to 0.47, 0.50 to 0.47, less than about 0.90, less than about 0.80, less than about 0.70, less than about 0.60, less than about 0.50, and any range formed from values contained in the listed ranges.

Tables 20-21 below provide examples of the percentage change in the average molecular weight (in Daltons) of starch in whole oat flour as it undergoes controlled hydrolysis during extrusion to provide SoluOat flour. As can be seen, the average molecular weight of the starch in both sample 1 and sample 2 decreased by more than 50%. Accordingly, the molecular weight of the SoluOat flour is only a fraction of the molecular weight of the original whole oat flour starting material. Furthermore, as can be seen, there was only a small change in the wt. % of the starch as a component of the flour. This change was a small increase in sample 1 and a small decrease in sample 2. It should be noted that in some circumstances the experimental data can be affected by measurement error, detection limits, natural variation in the mass concentration of a component in native plants, or variation in the mass concentration of a component with location in a batch as a result of imperfect mixing throughout the volume of the batch.

Tables 20-21 show how a certain mass of the starch can be shifted from higher molecular weight to lower molecular weight starch. For example, the high molecular weight amylopectin ("HMW-Amylopectin") decreases as a weight percentage of the starch and decreases in average molecular weight. Low molecular weight amylopectin ("LMW-Amylopectin") increases substantially as a weight percentage of the starch and decreases slightly in average molecular weight. The weight percentage of amylose increases slightly as a weight percentage of the starch and decreases substantially in average molecular weight. Accordingly, the average molecular weight of the starch decreases from about $3.7 \times 10^6$ to $1.7 \times 10^6$ Dalton.

TABLE 20

| | Starch Component | | | | | | | |
|---|---|---|---|---|---|---|---|---|
| | Starch | | HMW-Amylopectin | | LMW-Amylopectin | | Amylose | |
| Sample 1 | in flour wt. % | Avg. MW Da | in starch wt. % | Avg. MW Da | in starch wt. % | Avg. MW Da | in starch wt. % | Avg. MW Da |
| Whole oat flour | 60.34 | 3.667E+06 | 54.76 | 5.886E+06 | 20.51 | 1.744E+06 | 24.73 | 3.501E+05 |
| SoluOat flour | 61.02 | 1.729E+06 | 35.71 | 2.782E+06 | 39.23 | 1.703E+06 | 25.06 | 2.697E+05 |
| % change | 1.13 | −52.85 | −34.79 | −52.74 | 91.27 | −2.35 | 1.33 | −22.96 |

TABLE 21

| | Starch Component | | | | | | | |
|---|---|---|---|---|---|---|---|---|
| | Starch | | HMW-Amylopectin | | LMW-Amylopectin | | Amylose | |
| Sample 2 | in flour wt. % | Avg. MW Da | in starch wt. % | Avg. MW Da | in starch wt. % | Avg. MW Da | in starch wt. % | Avg. MW Da |
| Whole oat flour | 59.9 | 3.873E+06 | 54.17 | 6.243E+06 | 22.44 | 1.983E+06 | 23.38 | 1.962E+05 |
| SoluOat flour | 59.54 | 1.820E+06 | 34.91 | 3.034E+06 | 38.68 | 1.849E+06 | 26.42 | 1.709E+05 |
| % change | −0.60 | −53.02 | −35.55 | −51.40 | 72.37 | −6.76 | 13.00 | −12.90 |

In some embodiments, the average molecular weight of the gelatinized, hydrolyzed starch molecules in the at least a portion of grain is a fraction of the molecular weight of gelatinized, unhydrolyzed starch molecules equivalent (e.g., in kind and condition) to the gelatinized, hydrolyzed starch molecules in the at least a portion of grain, except that the gelatinized, unhydrolyzed starch molecules have not been hydrolyzed. For example, the fraction can be selected from the group consisting of about 0.90 to 0.47, 0.80 to 0.47, 0.70 to 0.47, 0.60 to 0.47, 0.50 to 0.47, less than about 0.90, less than about 0.80, less than about 0.70, less than about 0.60, less than about 0.50, and any range formed from values contained in the listed ranges.

more than about 60%, 50%, 40%, 30%, 20%, 10%, 9%, 8%, 7%, 6%, 5%, 4%, 3%, 2%, or 1% of the original molecular weight). This is so, because, for example, the starch molecules can be selectively reduced (e.g., using enzymes with only endo activity) in molecular weight to the smallest molecules that still constitute starch, but without being converted into molecules that are not starch, such as sugar (e.g., monosaccharides or disaccharides).

Tables 22-26 illustrate further examples of characteristics and extrusion conditions for at least a portion of pulse and/or grain (e.g., a flour) of various types. The extrusion conditions for the various flours shown in Tables 22-26 are provided in Table 22. Table 23 provides a key for various symbols and terms used in Tables 22 and 24-26.

TABLE 22

Extrusion Parameters for Streams of Various Flour Types

| Parameter | Stream Description | | | | | | | | | | |
|---|---|---|---|---|---|---|---|---|---|---|---|
| | 7 | 8 | 9 | 10 | 11 | 12 | 13 | 14 | 15 | 16 | 17 |
| Type of extruder | E | E | E | E | E | E | E | E | E | E | E |
| Feed rate of flour, lb/hr ** | 200 (90.7) | 200 (90.7) | 260 (118) | 260 (118) | 260 (118) | 260 (118) | 200 (90.7) | 200 (90.7) | 200 (90.7) | 200 (90.7) | 200 (90.7) |
| Tocopherol, wt. % | 0.5 | 0.5 | 0.5 | 0.5 | 0.5 | 0.5 | 0.5 | 0.5 | 0.5 | 0.5 | 0.5 |
| Enzyme type | α | α | α | α | α | α | α | α | α | α | α |
| Enzyme amount, wt. % | 0.12 | 0.12 | 0.12 | 0.06 | 0.06 | 0.15 | 0.096 | 0.1 | 0.1 | 0.1 | 0.1 |
| Moisture at pre-conditioner exit/ extruder inlet, wt. % | 32 | 32 | 29 | 29 | * | 31 | 31 | 31 | 31 | 33 | 33 |
| Dough temp. at preconditioner exit/extruder inlet (e.g., WMT), ° F./° C. | 171/ 77.22 | 167/ 75.00 | 168/ 75.56 | 172/ 77.78 | 172/ 77.78 | 174/ 78.89 | 166/ 74.44 | 166/ 74.44 | 168/ 75.56 | 166/ 74.44 | 168/ 75.56 |
| Extruder screw speed, RPM | 280 | 260 | 330 | 330 | 330 | 330 | 260 | 260 | 260 | 260 | 260 |
| Residence time, min | 1 | 1 | 1 | 1 | 1 | 1 | 1 | 1 | 1 | 1 | 1 |
| Pressure at exit end of extruder screw, PSI | * | * | * | * | * | * | * | * | * | * | * |
| Barrel temp., ° F./° C. | T | T | T | T | T | T | T | T | T | T | T |
| Extruder die wall exit temperature, ° F./° C. | 285/ 140.56 | 290/ 143.33 | 288/ 142.22 | 284/ 140.00 | 285/ 140.56 | 285/ 140.56 | 300/ 148.89 | 287/ 141.67 | 284/ 140.00 | 287/ 141.67 | 290/ 143.33 |

In some embodiments, the average molecular weight of the gelatinized, hydrolyzed starch molecules in the at least a portion of pulse is a fraction of the molecular weight of gelatinized, unhydrolyzed starch molecules equivalent (e.g., in kind and condition) to the gelatinized, hydrolyzed starch molecules in the at least a portion of pulse, except that the gelatinized, unhydrolyzed starch molecules have not been hydrolyzed. For example, the fraction can be selected from the group consisting of about 0.90 to 0.47, 0.80 to 0.47, 0.70 to 0.47, 0.60 to 0.47, 0.50 to 0.47, less than about 0.90, less than about 0.80, less than about 0.70, less than about 0.60, less than about 0.50, and any range formed from values contained in the listed ranges.

Moreover, in some embodiments, the average molecular weight of the hydrolyzed starch molecules can be reduced to a fraction of the original average molecular weight (e.g., no

TABLE 23

Key for Tables 22 and 24-26

| | |
|---|---|
| * | not measured |
| 7 | Green Groat |
| 8 | HiFi oat |
| 9 | Oat bran |
| 10 | Brown rice |
| 11 | White rice |
| 12 | RM blend (about 70 wt. % oat, 10 wt. % barley, 10 wt. % rye and 10 wt. % wheat); |
| 13 | Barley |
| 14 | Quinoa |
| 15 | Amaranth |

TABLE 23-continued

Key for Tables 22 and 24-26

| | |
|---|---|
| 16 | Oat + Yellow pea, 50:50 wt. % blend |
| 17 | Oat + Pinto bean, 50:50 wt. % blend |
| E | Werner & Pfleiderer Extruder ZSK-58 |
| α | α-amylase |
| T | barrel position 1, 2, 3, 4, 5: 170° F. (76.67° C.), 200° F. (93.33° C.), 225° F. (107.22° C.), 275° F. (135° C.), 300° F. (148.89° C.) |

Table 24 provides particle size analysis using laser diffraction for the at least a portion of pulse and/or grain after extrusion. Providing a desired particle size can be useful to provide a desired degree of dispersibility. In some embodiments, the average particle size (e.g., average equivalent spherical diameter on a volume-weighted basis) equal to about 50-200 (e.g., 94.5-193.4, 50-150, or any range contained within the listed ranges) microns, for example, as measured using laser-diffraction-based, particle-size measurement equipment (e.g., a Malvern Mastersizer 3000 equipped with a multi-angle log-spaced diode array type of detector, available from Malvern Instruments Ltd of Malvern, Worcestershire, United Kingdom). As used herein, the equivalent spherical diameter of a particle is determined by calculating the diameter of a sphere that would cause a measured result (e.g., in this case, light diffraction) for the particle.

In some embodiments, 10% by volume of the powder 118 particles have a particle size smaller than about 56.4 (optionally, 55, 50, 45, 40, 35, 30, or 25) microns; 50% by volume of the powder particles have a particle size smaller than about 190 (optionally, 185.1, 180, 170, 160, 150, 140, or 130) microns; 90% by volume of the powder particles have a particle size smaller than about 340 (optionally, 336.7, 320, 300, 280, 260, 240, 220, 200, 180) microns; or any combination thereof, where the particle size is the diameter of a sphere that would provide the same laser diffraction measurements as the particle. Furthermore, as a skilled person would understand after reading the present disclosure, additional embodiments can be provided in which a characteristic listed herein (e.g., Dx (10)) is equal to a first range whose endpoints are selected from any values listed herein (e.g., 33.8-52 µm). Moreover, additional embodiments can be provided in which a listed characteristic is equal to a second range whose endpoints are selected from any values contained within the first range.

In some embodiments, relatively smaller particle sizes decrease dispersibilty in a liquid and increase absorption of the liquid, while larger particles sizes increase dispersibility in a liquid and decrease absorption of the liquid.

TABLE 24

Malvern Particle Size Analysis Using Laser Diffraction for Various Streams of Flour After Extrusion and Milling

| Equivalent Spherical Diameter | Stream Description | | | | | | | | | | |
|---|---|---|---|---|---|---|---|---|---|---|---|
| | 7 | 8 | 9 | 10 | 11 | 12 | 13 | 14 | 15 | 16 | 17 |
| Dx (10), µm | 33.8 | 24.7 | 39.4 | 44 | 56.4 | 42.3 | 52 | 55.2 | * | 38.9 | * |
| Dx (50), µm | 119.7 | 82.6 | 141.2 | 143.4 | 155.3 | 139.4 | 185.1 | 150.9 | * | 130.2 | * |
| Dx (90), µm | 238.2 | 181.6 | 273.5 | 291.5 | 299.4 | 259.4 | 336.7 | 271.2 | * | 249.6 | * |
| D [4, 3], µm | 130.3 | 94.5 | 151.5 | 157.8 | 168.4 | 147.3 | 193.4 | 159 | * | 139.2 | * |

Key

| | |
|---|---|
| Equivalent Spherical Diameter | size of a particle determined by calculating the diameter of a sphere that would cause the measured result (e.g., in this case, light diffraction) for the particle |
| Dx (10) | 10% by volume of particles in a sample have a size below the Dx (10) size |
| Dx (50) | 50% by volume of particles in a sample have a size below the Dx (50) size |
| Dx (90) | 90% by volume of particles in a sample have a size below Dx (90) size |
| D [4, 3] | mean diameter for particles in a sample on a volume-weighted basis |

Table 25 provides various measured characteristics for at least a portion of pulse and/or grain before and after extrusion. As can be seen in Table 25, the viscosity (and other characteristics) of various native grains and/or pulses vary. Additionally, the viscosity (and other characteristics) can vary among varieties of the same species of grain and/or pulse. Furthermore, the viscosity (and other characteristics) of even a single variety of grain and/or pulse can vary with factors such as season, location, growing conditions, etc.

TABLE 25

Characteristics for Streams of Various Types of Flour Before and After Extrusion

| Characteristic | Stream Description | | | | | | | | | | |
|---|---|---|---|---|---|---|---|---|---|---|---|
| | 7 | 8 | 9 | 10 | 11 | 12 | 13 | 14 | 15 | 16 | 17 |
| starch content before, wt. % | 51.4 | 48.7 | 44.0 | 61.0 | 72.7 | 55.7 | 55.0 | 52.1 | 52.6 | 48.1 | 51.4 |
| starch content after, wt. % | 55.1 | 47.5 | 47.8 | 62.1 | 68.8 | 52.8 | 54.5 | 55.3 | 51.7 | 47.7 | 44.8 |
| % difference | 7.2 | −2.5 | 8.6 | 1.8 | −5.4 | −5.2 | −0.9 | 6.1 | −1.7 | −0.8 | −12.8 |
| fiber content before, wt. % | 10.2 | 12.2 | 15.8 | 4.2 | 1.2 | 10.9 | 13.3 | 6.3 | 7.7 | 5.1 | 8.9 |
| fiber content after, wt. % | 10.2 | 10.6 | 11.5 | 5.5 | 1.2 | 10.5 | 10.9 | 6.2 | 7.3 | 7.6 | 11.7 |
| % difference | 0.0 | −13.1 | −27.2 | 31.0 | 0.0 | −3.7 | −18.0 | −1.6 | −5.2 | 49.0 | 31.5 |
| RVA peak viscosity before, cP | 8076 | 7849 | 7979 | 9407 | 12442 | 8587 | 8005 | 5825 | 2031 | 5163 | 4978 |
| RVA peak viscosity after, cP | 1973 | 2256 | 3389 | 1910 | 949 | 1024 | 2203 | 517 | 30 | 2457 | 1857 |
| % difference | −75.6 | −71.3 | −57.5 | −79.7 | −92.4 | −88.1 | −72.5 | −91.1 | −98.5 | −52.4 | −62.7 |
| RVA Viscosity at 25° C. before, cP | 1015 | 1012 | 861 | 350 | 439 | 714 | 980 | 97 | 175 | 320 | 340 |
| RVA Viscosity at 25° C. after, cP | 312 | 166 | 145 | 50 | 33 | 142 | 78 | 37 | 20 | 72 | 107 |
| % difference | −69.3 | −83.6 | −83.2 | −85.7 | −92.5 | −80.1 | −92.0 | −61.9 | −88.6 | −77.5 | −68.5 |

The Rapid Visco Analyzer ("RVA") peak viscosity of the compositions in Table 25 was measured using the protocol discussed with reference to Tables 9, 13, and 17. The RVA viscosity at 25° C. of the compositions in Table 25 was measured using the following protocol. First, a mixture was formed consisting of a composition comprising at least a portion of pulse and/or grain, a specified wt. % tocopherol, a specified weight percentage of deactivated α-amylase, and a remainder of water. Water was added in an amount to provide the mixture with 6 wt. % solids. In other words, if the mixture were completely dehydrated by evaporating away the moisture, 6 wt. % solids would remain.

Second, the mixture was mixed by turning a shaft with a paddle at 500 rpm (for 5 seconds) until the composition, the tocopherol, and the deactivated α-amylase have absorbed an equilibrium amount of the water and are fully dispersed in the water to form the dispersion (e.g., generally homogeneous mixture, and to avoid clumps that can cause viscosity measurement errors).

Third, the dispersion was continuously mixed by turning a shaft with a paddle at 160 rpm and the viscosity of the dispersion was continuously measured while subjecting the dispersion to the following temperature profile: (i) heating the dispersion to about 95° C. over about 1 minute (ii) holding the dispersion at about 95° C. for about 11 minutes; (iii) cooling the dispersion to about 70° C. over about 1 minute; (iv) holding the dispersion at about 70° C. for about 5 minutes; (v) cooling the dispersion from about 70° C. to about 25° C. over about 8 minutes; (vi) holding the dispersion at about 25° C. for about 6 minutes. The RVA viscosity at 25° C. is the viscosity measured immediately after the dispersion has been subject to the temperature profile. In other words, the RVA viscosity at 25° C. is the viscosity measured immediately after holding the dispersion at about 25° C. for about 6 minutes.

Using a measurement protocol such as the protocol for the RVA viscosity at 25° C. can be useful, for example, to provide a way to compare the viscosity of compositions that are consumed or used after starch gelatinization. This is so because the RVA viscosity measurement protocol involves heating and hydrating the composition, which gelatinizes starch in the composition.

Table 26 provides various sensory characteristics for at least a portion of pulse and/or grain after extrusion. The sensory characteristics were characterized using a trained panel with 9 people. The individuals on the panel were given samples in duplicate and the results were averaged. Each sample was a slurry consisting of 5 wt. % of an extruded flour as shown and 95 wt. % water (e.g., 5 grams of the extruded flour was added to 95 grams of water). The results indicate the percentage of panelists who perceived the sample to have the listed characteristic (e.g., sticky).

TABLE 26

Sensory (Mouthfeel) Characteristics for Streams of Various Types of Flour After Extrusion

| Characteristic | Stream Description | | | | | | | | | | |
|---|---|---|---|---|---|---|---|---|---|---|---|
| | 7 | 8 | 9 | 10 | 11 | 12 | 13 | 14 | 15 | 16 | 17 |
| Sticky | 38% | 31% | 31% | 19% | * | 31% | 25% | 6% | * | 19% | * |
| Filmy | 94% | 94% | 81% | 44% | * | 69% | 88% | 63% | * | 56% | * |
| Oily | 0% | 13% | 13% | 6% | * | 0% | 13% | 0% | * | 6% | * |

TABLE 26-continued

Sensory (Mouthfeel) Characteristics for Streams of Various Types of Flour After Extrusion

| Characteristic | Stream Description | | | | | | | | | | |
|---|---|---|---|---|---|---|---|---|---|---|---|
| | 7 | 8 | 9 | 10 | 11 | 12 | 13 | 14 | 15 | 16 | 17 |
| Gritty | 6% | 0% | 6% | 25% | * | 13% | 13% | 19% | * | 19% | * |
| Grainy | 6% | 0% | 6% | 0% | * | 6% | 6% | 0% | * | 13% | * |
| Chalky | 63% | 44% | 44% | 75% | * | 75% | 50% | 56% | * | 69% | * |

Although various embodiments of the invention have been described herein, the features, elements, and/or steps of the embodiments and equivalent features, elements, and/or steps can be combined, interchanged, and/or omitted to form further embodiments, for example, as appropriate in light of the disclosure or as would be apparent to a person having ordinary skill in the art upon reading the disclosure. As an illustration, in some embodiments, the pulse product 914 from the extruder 934 can be added to or combined with another food (e.g., soup, beverage, dough) in a second mixer 942, (e.g., without pelletizing 1008, drying, 1009, granulating 1010, or any combination thereof). As another example, in some embodiments a mixer (e.g., the first mixer 930 and/or the second mixer 942) can be a homogenizer. Similarly, the steps of the methods described herein can be reordered to form further embodiments, for example, as appropriate in light of the disclosure or as would be apparent to a person having ordinary skill in the art upon reading the disclosure.

Additional Embodiments

The following clauses are offered as further description of the disclosed invention:
1. A beverage comprising soluble oat flour, wherein the beverage provides ½ to 1 serving of whole grain per 8 oz. serving of the beverage.
2. The beverage of clause 1 wherein the beverage is selected from the group consisting of ready-to-drink juice-based beverages and ready-to-drink milk-based beverages.
3. The beverage of clause 1 wherein the beverage is a juice-based smoothie, a milk-based smoothie, or oat-milk.
4. A method of making a beverage of clause 1 comprising hydrating soluble oat flour comprising mixing the soluble oat flour with a liquid at a temperature of 4 to 30° C., wherein the amount of soluble oat flour in the liquid is 1 wt. % to 10 wt. % based on total weight of the liquid; and adding the hydrated soluble oat flour to beverage components to form the beverage.
5. A semi-solid dairy product comprising soluble oat flour in an amount of 2 to 11 wt. % based on total weight of the semi-solid dairy product.
6. The semi-solid dairy product of clause 5 selected from the group consisting of dips, yogurt, ice-cream, and processed cheeses comprising hydrated soluble oat flour in an amount to provide ½ to 1 serving of whole grain per 4 oz. to 8 oz. serving of dairy product.
7. The semi-solid dairy product of clause 5 wherein the semi-solid dairy product is selected from the group consisting of yogurt, ice-cream, dips, and processed cheeses.
8. The semi-solid dairy product of clause 5 wherein the product is a reduced fat cream-based dip, wherein the dip contains 50% less fat compared to a full fat dip, and whereby the full fat dip and reduced fat cream-based dip have a viscosity of about 600,000 cp.
9. A method of making a semi-solid dairy product of clause 5 comprising hydrating soluble oat flour comprising mixing the soluble oat flour with a liquid at a temperature of 4 to 30° C., wherein the amount of soluble oat flour in the liquid is 2 wt. % to 11 wt. % based on total weight of the liquid; and adding the hydrated soluble oat flour to components to form the semi-solid dairy products.
10. An instant powder for preparing cold beverages comprising 25 to 60 wt. % soluble oat flour wherein, when hydrated in liquid, the beverage provides ½ to 1 serving of whole grain per 8 oz. serving of the beverage.
11. The instant powder of clause 10 wherein the beverage is selected from the group consisting of fruit juice, vegetable juice, milk beverage, water, shakes, and smoothies.
12. An instant powder comprising 25 to 35 wt. % soluble oat flour wherein, when hydrated in liquid, the powder provides ½ to 1 whole serving of whole grain per 4 to 8 oz. serving of product.
13. The instant powder of clause 12, wherein the instant powder further comprises components for preparing comestibles served hot and wherein, when hydrated in liquid, the comestible provides ½ to 1 whole serving of whole grain per 6 oz. serving of the comestible.
14. The instant powder of clause 13 wherein the comestibles are selected from the group consisting of hot chocolate, congee, gravy, sauce, and soup.
15. The instant powder of clause 12, wherein the instant powder further comprises components for preparing a semi-solid comestible product.
16. The instant powder of clause 15 wherein the semi-solid comestible product is selected from the group consisting of puddings, mousses, custards, and gelatins.
17. A bakery product selected from the group consisting of muffins, cookies, breads, bagels, pizza crust, cakes, crepes, and pancakes prepared from ingredients comprising soluble oat flour in an amount of 2 to 10 wt. % as a texturizer.
18. The bakery product of clause 17 wherein the product is a cookie comprising about 15-35 wt. % oat flour wherein the oat flour further comprises oat flakes, oat flour, and soluble oat flour.
19. The bakery product of clause 18 wherein oat flakes and oat flour comprise about 15-25 wt. % of the cookie and soluble oat flour comprises about 2-5 wt. % of the cookie.
20. The bakery product of clause 17 wherein the product is a muffin comprising about 20-30% wt. % flour and wherein about 5-10% of the oat flour is soluble oat flour.
21. The bakery product of clause 17 wherein the soluble oat flour provides at least 2 serving of whole grains.
22. Instant oatmeal comprising oat flakes and a powder, wherein the powder comprises flavors, sweeteners, and at least one texturizer; wherein the at least one texturizer comprises 0.09 to 0.3 wt. % soluble oat flour.

23. The instant oatmeal of clause 22 wherein the at least one texturizer consists of soluble oat flour and guar gum.

24. The instant oatmeal of clause 22 wherein the at least one texturizer consists of soluble oat flour.

25. A ready-to-eat soup comprising about 2 to 10 wt. % of soluble oat flour based on total weight of the soup wherein the soluble oat flour provides at least ½ serving of whole grains per 8 oz. serving.

26. A frozen commodity selected from the group consisting of ice cream and slushies comprising soluble oat flour in an amount of 2 to 10 wt. % based on total weight of the frozen commodity.

27. The frozen commodity of clause 26 wherein the frozen commodity is a slushie that exhibits antifoaming properties.

28. A method of producing a soluble oat or barley flour comprising:
combining a whole oat or barley flour starting mixture and a suitable enzyme to form an enzyme starting mixture;
heating the enzyme starting mixture to between about 48.89° C. and about 93.33° C. to begin to hydrolyze the starch molecules; and
extruding the resultant mixture to continue hydrolyzing the starch and further to gelatinize and cook the mixture to form the soluble oat or barley flour.

29. The method of clause 28 wherein the whole oat or barley flour starting mixture comprises whole oat or barley flour, granulated sugar, and at least one antioxidant.

30. The method of clause 29 wherein the whole oat or barley flour starting mixture further comprises a maltodextrin.

31. The method of clause 28 wherein the whole oat or barley flour starting mixture comprises about 50 to about 95% whole oat or barley flour, about 3 to about 15% granulated sugar, 0 to about 15% maltodextrin, and an effective amount of at least one antioxidant.

32. The method of clause 31 wherein the whole oat flour or barley starting mixture comprises about 80 to about 95% whole oat or barley flour.

33. The method of clause 31 wherein the whole oat flour or barley starting mixture comprises about 90 to about 95% whole oat or barley flour.

34. The method of clause 28 further comprising forming pelletized soluble oat or barley flour.

35. The method of clause 34 further comprising granulating the pelletized soluble oat or barley flour.

36. The method of clause 28 wherein the extruding occurs at a barrel temperature of about 60° C. to about 121.11° C.

37. The method of clause 28 wherein the extruding occurs at a dough temperature of about 100° C. to about 126.67° C.

38. The method of clause 28 wherein the enzyme starting mixture is heated to 60° C. to about 82.22° C.

39. A method for preparing a beverage containing a soluble oat or barley flour comprising:
combining a whole oat or barley flour starting mixture and a suitable enzyme to form an enzyme starting mixture;
heating the enzyme starting mixture to between about 48.89° C. and about 93.33° C. to begin to hydrolyze the starch molecules; and
extruding the resultant mixture to continue hydrolyzing the starch and further to gelatinize and cook the mixture to form the soluble oat or barley flour; and
adding the soluble oat or barley flour to a beverage.

40. The method of clause 39 wherein the beverage is selected from the group consisting of fruit juices, dairy beverages, and carbonated soft drinks.

41. The method of clause 40 wherein the soluble flour is added to provide a beverage having 1 to 25% soluble fiber based on total weight of the beverage.

42. A beverage prepared in accordance with the method of clause 39.

43. A method for preparing a food product containing a soluble oat or barley flour comprising:
combining a whole oat or barley flour starting mixture and a suitable enzyme to form an enzyme starting mixture;
heating the enzyme starting mixture to between about 48.89° C. and about 93.33° C. to begin to hydrolyze the starch molecules; and
extruding the resultant mixture to continue hydrolyzing the starch and further to gelatinize and cook the mixture to form the soluble oat or barley flour; and
adding the soluble oat or barley flour to a mixture for a food product.

44. The method of clause 43 wherein the food product is selected from the group consisting of bars, cereals, puddings, smoothies, ice cream, cookies, and crackers.

45. A method comprising:
combining at least a portion of pulse (e.g., a portion of a pulse, whole pulse, or whole pulse flour) and a suitable enzyme to form an enzyme-pulse starting mixture, wherein the enzyme-pulse starting mixture comprises starch;
heating the enzyme-pulse starting mixture to between about 120° F. (48.89° C.) and about 200° F. (93.33° C.) to begin to hydrolyze the starch (e.g., starch molecules), thereby providing a heated pulse mixture; and
extruding the heated pulse mixture to continue hydrolyzing the starch and further to gelatinize and cook the heated pulse mixture thereby providing a pulse product (e.g., at least a portion of pulse) comprising gelatinized, hydrolyzed starch.

46. The method of any method clause listed herein, excepting those clauses that are expressly contradictory to the present clause, wherein the enzyme-pulse starting mixture further comprises sugar (e.g., granulated sugar) and at least one antioxidant; and
wherein the pulse is selected from the group consisting of peas, lentils, chickpeas, navy beans, black turtle beans, cranberry beans, kidney beans, pinto beans, small red beans, Dutch brown beans, pink beans, and any combination thereof.

47. The method of clause 46 wherein the enzyme-pulse starting mixture further comprises a maltodextrin.

48. The method of any method clause listed herein, excepting those clauses that are expressly contradictory to the present clause:
wherein the at least a portion of pulse is pulse flour;
wherein the enzyme-pulse starting mixture comprises:
a mass ratio of sugar (e.g., granulated sugar) to pulse flour from about 0.03 to about 0.3;
a mass ratio of maltodextrin to pulse flour from about 0 to about 0.3; and
an effective amount of at least one antioxidant.

49. The method of clause 48 wherein the pulse flour is whole pulse flour.

50. The method of clause 48 wherein a pulse starting mixture comprises the at least a portion of pulse;
wherein the pulse starting mixture is combined with the suitable enzyme to form the enzyme-pulse starting mixture; and
wherein the pulse starting mixture comprises about 90 to about 95% by weight pulse flour (e.g., whole pulse flour).

51. The method of any method clause listed herein, excepting those clauses that are expressly contradictory to the present clause, further comprising pelletizing the pulse product to form pelletized pulse product (e.g., pellets or pelletized pulse flour).

52. The method of clause 51 further comprising granulating the pelletized pulse product to form granulated pulse product (e.g., granulated pulse flour).

53. The method of any method clause listed herein, excepting those clauses that are expressly contradictory to the present clause, wherein the extruding occurs at a barrel temperature selected from the group consisting of about 60° C. to about 176.67° C., about 132.22° C. to about 154.44° C., and about 143.33° C.

54. The method of any method clause listed herein, excepting those clauses that are expressly contradictory to the present clause, wherein during the extruding the heated pulse mixture is heated to a temperature of about 100° C. to about 176.67° C.

55. The method of any method clause listed herein, excepting those clauses that are expressly contradictory to the present clause, wherein during the heating the enzyme-pulse starting mixture is heated to 60° C. to about 82.22° C.

56. The method of any method clause listed herein, excepting those clauses that are expressly contradictory to the present clause, further comprising:
adding the pulse product to a beverage to provide a product composition.

57. The method of clause 56 wherein the beverage is selected from the group consisting of fruit juices, dairy beverages, and carbonated soft drinks.

58. The method of clause 57 wherein the pulse product is added to the beverage to provide the product composition with 1 to 25% soluble fiber based on total weight of the product composition.

59. A product composition prepared in accordance with the method of clause 56, wherein the product composition is a beverage.

60. The method of any method clause listed herein, excepting those clauses that are expressly contradictory to the present clause, further comprising:
adding the pulse product to a mixture for a food product (e.g. to provide a product composition).

61. The method of clause 60 wherein the food product is selected from the group consisting of bars, cereals, puddings, smoothies, ice cream, cookies, and crackers.

62. The method of any method clause listed herein, excepting those clauses that are expressly contradictory to the present clause:
wherein the combining step comprises combining the at least a portion of pulse, at least a portion of grain, and the suitable enzyme to form the enzyme-pulse starting mixture;
wherein the enzyme-pulse starting mixture is an enzyme-pulse-and-grain starting mixture;
wherein the heating step comprises heating the enzyme-pulse-and-grain starting mixture to between about 48.89° C. and about 93.33° C. to begin to hydrolyze the starch (e.g., starch molecules), thereby providing a heated pulse-and-grain mixture; and
wherein the extruding step comprises extruding the heated pulse-and-grain mixture to continue hydrolyzing the starch and further to gelatinize and cook the heated pulse-and-grain mixture thereby providing a pulse-and-grain product (e.g., at least a portion of pulse) comprising gelatinized, hydrolyzed starch.

63. The method of clause 62 wherein the enzyme-pulse-and-grain starting mixture further comprises sugar (e.g., granulated sugar) and at least one antioxidant;
wherein the pulse is selected from the group consisting of peas, lentils, chickpeas, navy beans, black turtle beans, cranberry beans, kidney beans, pinto beans, small red beans, Dutch brown beans, pink beans, and any combination thereof; and
wherein the grain is selected from the group consisting of wheat, oat, barley, corn, white rice, brown rice, barley, millet, sorghum, rye, triticale, teff, spelt, buckwheat, *quinoa*, amaranth, kaniwa, cockscomb, green groat, and any combination thereof.

64. The method of clause 63 wherein the enzyme-pulse-and-grain starting mixture further comprises a maltodextrin.

65. The method of clause 62
wherein the at least a portion of pulse is pulse flour;
wherein the at least a portion of grain is grain flour;
wherein the enzyme-pulse-and-grain starting mixture comprises:
a mass ratio of sugar (e.g., granulated sugar) to the combined pulse flour and grain flour from about 0.03 to about 0.3, optionally 0.03 to 0.15;
a mass ratio of maltodextrin to the combined pulse flour and grain flour from about 0 to about 0.3, optionally 0.03 to 0.15; and
an effective amount of at least one antioxidant.

66. The method of clause 65 wherein the grain flour is whole grain flour.

67. The method of clause 65 wherein a pulse starting mixture comprises the at least a portion of pulse;
wherein a grain starting mixture comprises the at least a portion of grain;
wherein the pulse starting mixture and the grain starting mixture are combined with the suitable enzyme to form the enzyme-pulse-and-grain starting mixture;
wherein the pulse starting mixture comprises about 90 to about 95% by weight pulse flour (e.g., whole pulse flour);
wherein the pulse starting mixture comprises about 90 to about 95% by weight pulse flour (e.g., whole pulse flour).

68. The method of clause 62 further comprising pelletizing the pulse-and-grain product to form pelletized pulse-and-grain product (e.g., pulse-and-grain pellets or pulse-and-grain flour).

69. The method of clause 68 further comprising granulating the pelletized pulse-and-grain product to form granulated pulse-and-grain product (e.g., granulated pulse-and-grain flour).

70. The method of clause 62 wherein the extruding occurs at a barrel temperature of about 60° C. to about 176.67° C.

71. The method of clause 62 wherein during the extruding the heated pulse-and-grain mixture is heated to a temperature of about 100° C. to about 160° C.

72. The method of clause 62 wherein during the heating the enzyme-pulse-and-grain starting mixture is heated to 60° C. to about 82.22° C.

73. The method of clause 63 further comprising:
adding the pulse-and-grain product to a beverage to provide a product composition.

74. The method of clause 73 wherein the beverage is selected from the group consisting of fruit juices, dairy beverages, and carbonated soft drinks.

75. The method of clause 74 wherein the pulse-and-grain product is added to the beverage to provide the product composition with 1 to 25% soluble fiber based on total weight of the product composition.

76. A product composition prepared in accordance with the method of clause 73, wherein the product composition is a beverage.

77. The method of clause 62 further comprising:
adding the pulse-and-grain product to a mixture for a food product.

78. The method of clause 77 wherein the food product is selected from the group consisting of bars, cereals, puddings, smoothies, ice cream, cookies, and crackers.

79. A composition comprising:

at least a portion of pulse (e.g., whole pulse, whole pulse flour, extruded whole pulse flour);

wherein the at least a portion of pulse comprises gelatinized, hydrolyzed starch.

80. The composition of any composition clause listed herein, excepting those clauses that are expressly contradictory to the present clause:

wherein the at least a portion of pulse is hydrolyzed-starch pulse (e.g., beans, peas, chickpeas, etc.) and optionally hydrolyzed-starch whole pulse comprising gelatinized, hydrolyzed starch; and wherein the hydrolyzed-starch pulse has, within a tolerance of +/−20% (optionally, 15%, 10%, 5%, 2% or 1%), at least one mass ratio selected from the group consisting of:

a mass ratio of starch to protein equal to a mass ratio of starch to protein of unhydrolyzed pulse (e.g., pulse comprising gelatinized, unhydrolyzed starch or whole pulse comprising gelatinized, unhydrolyzed starch) equivalent in kind and condition to the hydrolyzed-starch pulse;

a mass ratio of fat to protein equal to a mass ratio of fat to protein of unhydrolyzed pulse equivalent in kind and condition to the hydrolyzed-starch pulse;

a mass ratio of dietary fiber to protein equal to a mass ratio of dietary fiber to protein of unhydrolyzed pulse equivalent in kind and condition to the hydrolyzed-starch pulse; and any combination thereof.

81. The composition of any composition clause listed herein, excepting those clauses that are expressly contradictory to the present clause, wherein, at a time of harvesting the at least a portion of pulse (e.g., whole pulse), the at least a portion of pulse comprises an original set of components comprising starch and protein, wherein at the time of harvesting the at least a portion of pulse, the at least a portion of pulse comprises each component in the original set of components at an original mass ratio relative to the protein;

wherein the at least a portion of pulse comprises each component in the original set of components at the original mass ratio relative to the protein, within a tolerance of +/−20% (optionally 15%, 10%, 5%, 2% or 1%);

optionally, wherein the composition comprises at least about 90, 95, 96, 97, 98, 99, 99.94 wt. % pulse on a dry basis, about 90 to 99.94 wt. % pulse on a dry basis, or any range formed by values contained within the listed ranges;

optionally, wherein the at least a portion of pulse comprises whole pulse.

82. The composition of any composition clause listed herein, excepting those clauses that are expressly contradictory to the present clause, further comprising:

deactivated amylase enzyme (e.g., α-amylase enzyme).

83. The composition of any composition clause listed herein, excepting those clauses that are expressly contradictory to the present clause, wherein the at least a portion of pulse comprises (optionally, consists of) pulse (e.g., whole pulse) selected from the group consisting of peas, lentils, chickpeas, navy beans, black turtle beans, cranberry beans, kidney beans, pinto beans, small red beans, Dutch brown beans, pink beans and combinations thereof.

84. The composition of any composition clause listed herein, excepting those clauses that are expressly contradictory to the present clause, wherein the composition comprises on a dry basis at least about 90 wt. % (optionally, about 95, 96, 97, 98, 99, or 99.94 wt. %, or about 90 to 99.94, or any range formed by values contained within the listed ranges) of the at least a portion of pulse.

85. The composition of any composition clause listed herein, excepting those clauses that are expressly contradictory to the present clause, wherein the composition comprises water.

86. The composition of any composition clause listed herein, excepting those clauses that are expressly contradictory to the present clause, wherein the composition comprises at least 80 wt. % water (for example, from a water-based liquid (e.g., pure water, milk, fruit juice, etc.).

87. The composition of any composition clause listed herein, excepting those clauses that are expressly contradictory to the present clause, wherein the composition comprises at least about 3.0 wt. % of the at least a portion of pulse (e.g., whole pulse flour).

88. The composition of any composition clause listed herein, excepting those clauses that are expressly contradictory to the present clause, wherein the composition comprises at least about 10 wt. % of the at least a portion of pulse (e.g., whole pulse flour).

89. The composition of any composition clause listed herein, excepting those clauses that are expressly contradictory to the present clause, wherein the composition comprises about 3.3 wt. % to about 6.6 wt. % of the at least a portion of pulse (e.g., whole pulse flour), optionally wherein the composition is a beverage.

90. The composition of any composition clause listed herein, excepting those clauses that are expressly contradictory to the present clause, wherein the at least a portion of pulse is made by hydrolyzing starch in pulse (e.g., whole pulse).

91. The composition of any composition clause listed herein, excepting those clauses that are expressly contradictory to the present clause, wherein the composition is a first composition, and wherein the first composition has a viscosity at 25° C. (e.g., an RVA viscosity at 25° C.) that is at most 75% (or 70%, 60%, 50%, 40%, 30%, 20%, 10% or 5%) of a viscosity at 25° C. (e.g., an RVA viscosity at 25° C.) of a second composition that is equivalent to the first composition except that the second composition comprises gelatinized, unhydrolyzed starch in place of gelatinized, hydrolyzed starch.

92. The composition of any composition clause listed herein, excepting those clauses that are expressly contradictory to the present clause, wherein the composition is a first composition;

wherein the first composition consists of a first set of ingredients;

wherein the first set of ingredients comprises the at least a portion of pulse and water;

wherein the first composition consists of each ingredient in the first set of ingredients at a specified weight percentage;

wherein the first composition comprises a viscosity at 25° C. (e.g., an RVA viscosity at 25° C.) that is at most 75% (or 70%, 60%, 50%, 40%, 30%, 20%, 10% or 5%) of a viscosity at 25° C. (e.g., an RVA viscosity at 25° C.) of a second composition;

wherein the second composition consists of the first set of ingredients in the specified weight percentages, except that the at least a portion of pulse comprising gelatinized, hydrolyzed starch is replaced with at least a portion of pulse comprising gelatinized, unhydrolyzed starch.

93. The composition of any composition clause listed herein, excepting those clauses that are expressly contradictory to the present clause, further comprising:
 at least a portion of grain (e.g., starchy endosperm, germ, bran, whole grain, or whole grain flour); and
 wherein the at least a portion of grain comprises gelatinized, hydrolyzed starch.

94. The composition of clause 93:
 wherein the at least a portion of grain is hydrolyzed-starch bran (e.g., oat, rice, wheat, sorghum, etc.) comprising gelatinized, hydrolyzed starch; and
 wherein the hydrolyzed-starch bran has within a tolerance of +/−20% (optionally, 15%, 10%, 5%, 2% or 1%) at least one mass ratio selected from the group consisting of:
 a mass ratio of starch to protein equal to a mass ratio of starch to protein of unhydrolyzed bran (e.g., bran comprising gelatinized, unhydrolyzed starch) equivalent in kind and condition to the hydrolyzed-starch bran;
 a mass ratio of fat to protein equal to a mass ratio of fat to protein of unhydrolyzed bran equivalent in kind and condition to the hydrolyzed-starch bran;
 a mass ratio of dietary fiber to protein equal to a mass ratio of dietary fiber to protein of unhydrolyzed bran equivalent in kind and condition to the hydrolyzed-starch bran; and
 any combination thereof.

95. The composition of clause 94:
 wherein the hydrolyzed-starch bran is oat bran;
 wherein the oat bran comprises:
 at least about 5.5 wt. % beta-glucan on a total dry weight basis (e.g., after removing any water by dehydrating); and
 at least about 16.0 wt. % dietary fiber on a total dry weight basis;
 wherein at least one-third of the total dietary fiber is soluble fiber.

96. The composition of clause 93:
 wherein the at least a portion of grain is hydrolyzed-starch whole grain (e.g., oat, rice, wheat, sorghum, etc.) comprising gelatinized, hydrolyzed starch; and
 wherein the hydrolyzed-starch whole grain has within a tolerance of +/−20% (optionally, 15%, 10%, 5%, 2% or 1%) at least one mass ratio selected from the group consisting of:
 a mass ratio of starch to protein equal to a mass ratio of starch to protein of unhydrolyzed whole grain equivalent in kind and condition to the hydrolyzed-starch whole grain;
 a mass ratio of fat to protein equal to a mass ratio of fat to protein of unhydrolyzed whole grain equivalent in kind and condition to the hydrolyzed-starch whole grain;
 a mass ratio of dietary fiber to protein equal to a mass ratio of dietary fiber to protein of unhydrolyzed whole grain equivalent in kind and condition to the hydrolyzed-starch whole grain; and
 any combination thereof.

97. The composition of clause 93, wherein the at least a portion of grain is whole grain;
 wherein, at a time of harvesting the whole grain, the whole grain comprises an original set of components comprising starch, fat, dietary fiber, and protein,
 wherein at the time of harvesting the whole grain, the whole grain comprises each component in the original set of components at an original mass ratio relative to the protein;
 wherein the at least a portion of grain comprises each component in the original set of components at the original mass ratio relative to the protein within a tolerance of +/−20% (optionally, 15%, 10%, 5%, 2% or 1%);
 optionally, wherein the composition comprises at least about 90, 95, 96, 97, 98, 99, 99.94 wt. % whole grain on a dry basis, about 90 to 99.94 wt. % whole grain on a dry basis, or any range formed by values contained within the listed ranges.

98. The composition of clause 93,
 wherein the at least a portion of grain is hydrolyzed-starch whole grain (e.g., whole grain flour ground from a whole grain);
 wherein the at least a portion of grain comprises caryopses (e.g., intact, ground, cracked, or flaked);
 wherein the caryopses comprise principal anatomical components;
 wherein the principal anatomical components consist of starchy endosperm, germ, and bran;
 wherein the hydrolyzed-starch whole grain has within a tolerance of +/−20% (optionally, 15%, 10%, 5%, 2% or 1%) at least one mass ratio selected from the group consisting of:
 a mass ratio of germ to endosperm equivalent to a mass ratio of germ to endosperm of unhydrolyzed intact caryopses of the same kind and condition as the caryopses of the hydrolyzed-starch whole grain;
 a mass ratio of bran to endosperm equivalent to a mass ratio of bran to endosperm of unhydrolyzed intact caryopses of the same kind and condition as the caryopses of the hydrolyzed-starch whole grain; and
 any combination thereof;
 optionally, wherein the composition comprises at least about 90, 95, 96, 97, 98, 99, 99.94 wt. % hydrolyzed starch whole grain on a dry basis, about 90 to 99.94 wt. % hydrolyzed-starch whole grain on a dry basis, or any range formed by values contained within the listed ranges.

99. The composition of clause 93, further comprising:
 deactivated amylase enzyme (e.g., α-amylase).

100. The composition of clause 93, wherein the at least a portion of grain is an extruded whole grain flour.

101. The composition of clause 93, wherein the at least a portion of grain comprises whole grain selected from the group consisting of wheat, oat, barley, corn, white rice, brown rice, barley, millet, sorghum, rye, triticale, teff, spelt, buckwheat, *quinoa*, amaranth, kaniwa, cockscomb, green groat (e.g., dehulled oats that are not heat treated by kilning or otherwise) and combinations thereof.

102. The composition of clause 93, wherein the composition comprises (optionally, comprises on a dry basis about 90 to 99.94 wt. %, at least about 90, 95, 96, 97, 98, 99, 99.94 wt. %, or any range formed using these values as endpoints) a combination of pulse flour (e.g., whole pulse flour) and whole grain flour.

103. The composition of clause 93, wherein the composition comprises water.

104. The composition of clause 93, wherein the composition comprises at least about 80 wt. % water (for example, from a water-based liquid (e.g., pure water, milk, fruit juice, etc.)).

105. The composition of clause 93, wherein the composition comprises at least about 1 wt. % of the at least a portion of grain (e.g., whole grain flour).

106. The composition of clause 93, wherein the composition comprises about 6.6 wt. % to about 15 wt. % of the at least a portion of grain (e.g., whole grain flour), optionally about 6.6 wt. % to about 12 wt. % or about 12 wt. % to about 15 wt. %.

107. The composition of clause 93, wherein the composition comprises about 3.3 wt. % to about 6.6 wt. % of the at least a portion of grain (e.g., whole grain flour).

108. The composition of clause 93, wherein the at least a portion of grain is whole grain flour; and
 wherein the whole grain flour is made by hydrolyzing a whole grain.

109. The composition of clause 93, wherein the composition is a first composition, and wherein the first composition has a viscosity at 25° C. (e.g., an RVA viscosity at 25° C.) that is at most (e.g., no more than) 75% (optionally, 70%, 60%, 50%, 40%, 30%, 20%, 10% or 5%) of a viscosity at 25° C. (e.g., an RVA viscosity at 25° C.) of a second composition that is equivalent to the first composition except that the second composition comprises gelatinized, unhydrolyzed starch in place of gelatinized, hydrolyzed starch.

110. The composition of clause 93, wherein the composition is a first composition;
wherein the first composition consists of a first set of ingredients;
wherein the first set of ingredients comprises the at least a portion of pulse, the at least a portion of grain, and water;
wherein the first composition consists of each ingredient in the first set of ingredients at a specified weight percentage;
wherein the first composition comprises a viscosity at 25° C. (e.g., an RVA viscosity at 25° C.) that is at most (e.g., no more than) 75% (optionally, 70%, 60%, 50%, 40%, 30%, 20%, 10% or 5%) of a viscosity at 25° C. (e.g., an RVA viscosity at 25° C.) of a second composition;
wherein the second composition consists of the first set of ingredients in the specified weight percentages, except that the at least a portion of pulse comprising gelatinized, hydrolyzed starch is replaced with at least a portion of pulse comprising gelatinized, unhydrolyzed starch, and except that the at least a portion of grain comprising gelatinized, hydrolyzed starch is replaced with at least a portion of grain comprising gelatinized, unhydrolyzed starch.

111. The composition of clause 93, wherein the average molecular weight of the gelatinized, hydrolyzed starch molecules in the composition is a fraction of the molecular weight of gelatinized, unhydrolyzed starch molecules equivalent (e.g., in kind and condition) to the gelatinized, hydrolyzed starch molecules, except that the gelatinized, unhydrolyzed starch molecules have not been hydrolyzed;
wherein the fraction is selected from the group consisting of about 0.90 to 0.47, 0.80 to 0.47, 0.70 to 0.47, 0.60 to 0.47, 0.50 to 0.47, less than about 0.90, less than about 0.80, less than about 0.70, less than about 0.60, and less than about 0.50.

112. The composition of clause 93, wherein the average molecular weight of the gelatinized, hydrolyzed starch molecules in the at least a portion of grain is a fraction of the molecular weight of gelatinized, unhydrolyzed starch molecules equivalent (e.g., in kind and condition) to the gelatinized, hydrolyzed starch molecules in the at least a portion of grain, except that the gelatinized, unhydrolyzed starch molecules have not been hydrolyzed;
wherein the fraction is selected from the group consisting of about 0.90 to 0.47, 0.80 to 0.47, 0.70 to 0.47, 0.60 to 0.47, 0.50 to 0.47, less than about 0.90, less than about 0.80, less than about 0.70, less than about 0.60, and less than about 0.50.

113. The composition of clause 93, wherein the average molecular weight of the gelatinized, hydrolyzed starch molecules in the at least a portion of pulse is a fraction of the molecular weight of gelatinized, unhydrolyzed starch molecules equivalent (e.g., in kind and condition) to the gelatinized, hydrolyzed starch molecules in the at least a portion of pulse, except that the gelatinized, unhydrolyzed starch molecules have not been hydrolyzed;
wherein the fraction is selected from the group consisting of about 0.90 to 0.47, 0.80 to 0.47, 0.70 to 0.47, 0.60 to 0.47, 0.50 to 0.47, less than about 0.90, less than about 0.80, less than about 0.70, less than about 0.60, and less than about 0.50.

114. The composition of clause 93, wherein the at least a portion of grain is green groat;
wherein solid particles in the composition (or the at least a portion of grain) are characterized by at least one particle size distribution criterion selected from the group of particle size distribution criteria consisting of:
a first criterion that 10% by volume of the solid particles have a particle size no more than about 37.2 microns (e.g., no more than about 33.8 microns);
a second criterion that 50% by volume of the solid particles have a particle size no more than about 131.7 microns (e.g., no more than about 119.7 microns);
a third criterion that 90% by volume of the solid particles have a particle size no more than about 262.1 microns (e.g., no more than about 238.2 microns);
a fourth criterion that the solid particles have a volume-weighted average particle size no more than about 143.4 microns (e.g., no more than about 130.3 microns, or from about 117.2 to about 143.4 microns); and
any combination thereof;
optionally, wherein the particle size is the average equivalent spherical diameter of a particle on a volume-weighted basis as measured using laser-diffraction-based, particle-size measurement equipment (e.g., a Malvern Mastersizer 3000 equipped with a multi-angle log-spaced diode array type of detector), and wherein an equivalent spherical diameter of the particle is determined by calculating the diameter of a sphere that would cause a measured result (e.g., a measured light diffraction) for the particle.

115. The composition of clause 93, wherein the at least a portion of grain is HiFi variety oat (e.g., HiFi variety oat registered under the Plant Protection Act, with certificate number 200300193 to NDSU Research foundation, having a mean groat protein content of about 18.7 wt. % dry basis and a mean groat Beta-glucan content of about 6.42 wt. % dry basis);
wherein solid particles in the composition (or the at least a portion of grain) are characterized by at least one particle size distribution criterion selected from the group of particle size distribution criteria consisting of:
a first criterion that 10% by volume of the solid particles have a particle size no more than about 27.2 microns (e.g., no more than about 24.7 microns);
a second criterion that 50% by volume of the solid particles have a particle size no more than about 90.9 microns (e.g., no more than about 82.6 microns);
a third criterion that 90% by volume of the solid particles have a particle size no more than about 199.8 microns (e.g., no more than about 181.6 microns);
a fourth criterion that the solid particles have a volume-weighted average particle size no more than about 104.0 microns (e.g., no more than about 94.5 microns, or from about 85.0 to about 104.0 microns); and
any combination thereof.

116. The composition of clause 93, wherein the at least a portion of grain is oat bran;
wherein solid particles in the composition (or the at least a portion of grain) are characterized by at least one particle size distribution criterion selected from the group of particle size distribution criteria consisting of:
a first criterion that 10% by volume of the solid particles have a particle size no more than about 43.4 microns (e.g., no more than about 39.4 microns);

a second criterion that 50% by volume of the solid particles have a particle size no more than about 155.4 microns (e.g., no more than about 141.2 microns);

a third criterion that 90% by volume of the solid particles have a particle size no more than about 300.9 microns (e.g., no more than about 273.5 microns);

a fourth criterion that the solid particles have a volume-weighted average particle size no more than about 166.7 microns (e.g., no more than about 151.5 microns, or from about 136.3 to about 166.7 microns); and any combination thereof.

117. The composition of clause 93, wherein the at least a portion of grain is brown rice;

wherein solid particles in the composition (or the at least a portion of grain) are characterized by at least one particle size distribution criterion selected from the group of particle size distribution criteria consisting of:

a first criterion that 10% by volume of the solid particles have a particle size no more than about 48.4 microns (e.g., no more than about 44.0 microns);

a second criterion that 50% by volume of the solid particles have a particle size no more than about 157.8 microns (e.g., no more than about 143.4 microns);

a third criterion that 90% by volume of the solid particles have a particle size no more than about 320.7 microns (e.g., no more than about 291.5 microns);

a fourth criterion that the solid particles have a volume-weighted average particle size no more than about 173.6 microns (e.g., no more than about 157.8 microns, or from about 142.0 to about 173.6 microns); and any combination thereof.

118. The composition of clause 93, wherein the at least a portion of grain is white rice;

wherein solid particles in the composition (or the at least a portion of grain) are characterized by at least one particle size distribution criterion selected from the group of particle size distribution criteria consisting of:

a first criterion that 10% by volume of the solid particles have a particle size no more than about 62.1 microns (e.g., no more than about 56.4 microns);

a second criterion that 50% by volume of the solid particles have a particle size no more than about 170.9 microns (e.g., no more than about 155.3 microns);

a third criterion that 90% by volume of the solid particles have a particle size no more than about 329.4 microns (e.g., no more than about 299.4 microns);

a fourth criterion that the solid particles have a volume-weighted average particle size no more than about 185.3 microns (e.g., no more than about 168.4 microns, or from about 151.5 to about 185.3 microns); and any combination thereof.

119. The composition of clause 93, wherein the at least a portion of grain is RM blend (e.g., about 70 wt. % oat, 10 wt. % barley, 10 wt. % rye and 10 wt. % wheat with a tolerance of +/−10% of the wt. % of each cereal grain component);

wherein solid particles in the composition (or the at least a portion of grain) are characterized by at least one particle size distribution criterion selected from the group of particle size distribution criteria consisting of:

a first criterion that 10% by volume of the solid particles have a particle size no more than about 46.6 microns (e.g., no more than about 42.3 microns);

a second criterion that 50% by volume of the solid particles have a particle size no more than about 153.4 microns (e.g., no more than about 139.4 microns);

a third criterion that 90% by volume of the solid particles have a particle size no more than about 285.4 microns (e.g., no more than about 259.4 microns);

a fourth criterion that the solid particles have a volume-weighted average particle size no more than about 162.1 microns (e.g., no more than about 147.3 microns, or from about 132.5 to about 162.1 microns); and any combination thereof.

120. The composition of clause 93, wherein the at least a portion of grain is barley;

wherein solid particles in the composition (or the at least a portion of grain) are characterized by at least one particle size distribution criterion selected from the group of particle size distribution criteria consisting of:

a first criterion that 10% by volume of the solid particles have a particle size no more than about 57.2 microns (e.g., no more than about 52.0 microns);

a second criterion that 50% by volume of the solid particles have a particle size no more than about 203.7 microns (e.g., no more than about 185.1 microns);

a third criterion that 90% by volume of the solid particles have a particle size no more than about 370.4 microns (e.g., no more than about 336.7 microns);

a fourth criterion that the solid particles have a volume-weighted average particle size no more than about 212.8 microns (e.g., no more than about 193.4 microns, or from about 174.0 to about 212.8 microns); and any combination thereof.

121. The composition of clause 93, wherein the at least a portion of grain is *quinoa;* wherein solid particles in the composition (or the at least a portion of grain) are characterized by at least one particle size distribution criterion selected from the group of particle size distribution criteria consisting of:

a first criterion that 10% by volume of the solid particles have a particle size no more than about 60.8 microns (e.g., no more than about 55.2 microns);

a second criterion that 50% by volume of the solid particles have a particle size no more than about 166.0 microns (e.g., no more than about 150.9 microns);

a third criterion that 90% by volume of the solid particles have a particle size no more than about 298.4 microns (e.g., no more than about 271.2 microns);

a fourth criterion that the solid particles have a volume-weighted average particle size no more than about 174.9 microns (e.g., no more than about 159.0 microns, or from about 143.1 to about 174.9 microns); and any combination thereof.

122. The composition of clause 93, wherein the at least a portion of grain is 50 wt. % oat and 50 wt. % yellow pea;

wherein solid particles in the composition (or the at least a portion of grain) are characterized by at least one particle size distribution criterion selected from the group of particle size distribution criteria consisting of:

a first criterion that 10% by volume of the solid particles have a particle size no more than about 42.8 microns (e.g., no more than about 38.9 microns);

a second criterion that 50% by volume of the solid particles have a particle size no more than about 143.3 microns (e.g., no more than about 130.2 microns);

a third criterion that 90% by volume of the solid particles have a particle size no more than about 274.6 microns (e.g., no more than about 249.6 microns);

a fourth criterion that the solid particles have a volume-weighted average particle size no more than about 153.2 microns (e.g., no more than about 139.2 microns, or from about 125.2 to about 153.2 microns); and any combination thereof.

123. The composition of clause 93,
wherein a 6 wt. % standardized dynamic viscosity of a measured composition is a dynamic viscosity of a dispersion comprising the measured composition taken at about 25° C. immediately after performing the following steps in the following order:
forming a mixture consisting essentially of (or consisting of) the measured composition, about 0.5 wt. % tocopherol (which can be present in the measured composition or added if not present), a specific weight percentage of deactivated α-amylase (which can be present in the measured composition or added if not present), and a remainder of water, wherein the mixture comprises about 6 wt. % dry solids;
mixing the mixture by turning a shaft with a paddle at 500 rpm (e.g., for about 5 seconds) until the measured composition, the tocopherol, and the deactivated α-amylase have absorbed an equilibrium amount of the water and are fully dispersed in the water to form the dispersion (e.g., homogeneous mixture, to avoid clumps that can cause viscosity measurement errors);
heating the dispersion from room temperature (e.g. 25° C.) to about 95° C. over about 1 minute while mixing the dispersion by turning a shaft with a paddle at 160 rpm;
holding the dispersion at about 95° C. for about 11 minutes while mixing the dispersion by turning a shaft with a paddle at 160 rpm;
cooling the dispersion from about 95° C. to about 70° C. over about 1 minute while mixing the dispersion by turning a shaft with a paddle at 160 rpm;
holding the dispersion at about 70° C. for about 5 minutes while mixing the dispersion by turning a shaft with a paddle at 160 rpm;
cooling the dispersion from about 70° C. to about 25° C. over about 8 minutes while mixing the dispersion by turning a shaft with a paddle at 160 rpm;
holding the dispersion at about 25 C for about 6 minutes while mixing the dispersion by turning a shaft with a paddle at 160 rpm;
wherein the 6 wt. % standardized dynamic viscosity of the at least a portion of grain is no more than about 90% (optionally 80%, 70%, 60%, 50%, 40%, 30%, 20%, 10% or 5%) of the 6 wt. % standardized dynamic viscosity of a reference sample that is equivalent to (e.g., of the same kind and/or condition, as) the at least a portion of grain, except that the reference sample comprises unhydrolyzed starch in place of the hydrolyzed starch of the at least a portion of grain.

124. The composition of clause 123,
wherein the at least a portion of grain is whole grain green groat flour;
wherein the specific weight percentage of the deactivated α-amylase is about 0.12 wt. %; and
wherein the 6 wt. % standardized dynamic viscosity of the at least a portion of grain is no more than about 90% (optionally, 80%, 70%, 60%, 50%, 40%, or 31%) of the 6 wt. % standardized dynamic viscosity of the reference sample.

125. The composition of clause 123,
wherein the at least a portion of grain is whole grain HiFi variety oat flour;
wherein the specific weight percentage of the deactivated α-amylase is about 0.12 wt. %; and
wherein the 6 wt. % standardized dynamic viscosity of the at least a portion of grain is no more than about 90% (optionally, 80%, 70%, 60%, 50%, 40%, 30%, 20%, or 17%) of the 6 wt. % standardized dynamic viscosity of the reference sample.

126. The composition of clause 123,
wherein the at least a portion of grain is oat bran flour;
wherein the specific weight percentage of the deactivated α-amylase is about 0.12 wt. %; and
wherein the 6 wt. % standardized dynamic viscosity of the at least a portion of grain is no more than about 90% (optionally, 80%, 70%, 60%, 50%, 40%, 30%, 20%, or 17%) of the 6 wt. % standardized dynamic viscosity of the reference sample.

127. The composition of clause 123,
wherein the at least a portion of grain is whole grain brown rice flour;
wherein the specific weight percentage of the deactivated α-amylase is about 0.06 wt. %; and
wherein the 6 wt. % standardized dynamic viscosity of the at least a portion of grain is no more than about 90% (optionally, 80%, 70%, 60%, 50%, 40%, 30%, 20%, or 15%) of the 6 wt. % standardized dynamic viscosity of the reference sample.

128. The composition of clause 123,
wherein the at least a portion of grain is whole grain white rice flour;
wherein the specific weight percentage of the deactivated α-amylase is about 0.06 wt. %; and
wherein the 6 wt. % standardized dynamic viscosity of the at least a portion of grain is no more than about 90% (optionally, 80%, 70%, 60%, 50%, 40%, 30%, 20%, 10%, or 7.6%) of the 6 wt. % standardized dynamic viscosity of the reference sample.

129. The composition of clause 123,
wherein the at least a portion of grain is whole grain RM blend flour;
wherein the specific weight percentage of the deactivated α-amylase is about 0.15 wt. %; and
wherein the 6 wt. % standardized dynamic viscosity of the at least a portion of grain is no more than about 90% (optionally, 80%, 70%, 60%, 50%, 40%, 30%, or 20%) of the 6 wt. % standardized dynamic viscosity of the reference sample.

130. The composition of clause 123,
wherein the at least a portion of grain is whole grain barley flour;
wherein the specific weight percentage of the deactivated α-amylase is about 0.096 wt. %; and
wherein the 6 wt. % standardized dynamic viscosity of the at least a portion of grain is no more than about 90% (optionally, 80%, 70%, 60%, 50%, 40%, 30%, 20%, 10%, or 8.0%) of the 6 wt. % standardized dynamic viscosity of the reference sample.

131. The composition of clause 123,
wherein the at least a portion of grain is whole grain *quinoa* flour;
wherein the specific weight percentage of the deactivated α-amylase is about 0.1 wt. %; and
wherein the 6 wt. % standardized dynamic viscosity of the at least a portion of grain is no more than about 90% (optionally, 80%, 70%, 60%, 50%, 40%, or 39%) of the 6 wt. % standardized dynamic viscosity of the reference sample.

132. The composition of clause 123,
wherein the at least a portion of grain is whole grain amaranth flour;
wherein the specific weight percentage of the deactivated α-amylase is about 0.1 wt. %; and
wherein the 6 wt. % standardized dynamic viscosity of the at least a portion of grain is no more than about 90%

(optionally, 80%, 70%, 60%, 50%, 40%, 30%, 20%, or 12%) of the 6 wt. % standardized dynamic viscosity of the reference sample.

133. The composition of clause 93:
a mass ratio of starch to protein equal to about 3.51-4.87 (e.g., within a tolerance of +/−30%, 20%, 10%, 5%, or 1% of the mass ratio of starch to protein);
a mass ratio of fat to protein equal to about 0.39-0.58 (e.g., within a tolerance of +/−30%, 20%, 10%, 5%, or 1% of the mass ratio of fat to protein);
a mass ratio of dietary fiber to protein equal to about 0.61-0.84 (e.g., within a tolerance of +/−30%, 20%, 10%, 5%, or 1% of the mass ratio of dietary fiber to protein); and
any combination thereof.

134. The composition of clause 93:
wherein the at least a portion of grain is whole grain wheat comprising gelatinized, hydrolyzed starch; and
wherein the at least a portion of grain comprises at least one mass ratio selected from the group consisting of:
a mass ratio of starch to protein equal to about 4.61-6.28 (e.g., within a tolerance of +/−30%, 20%, 10%, 5%, or 1% of the mass ratio of starch to protein);
a mass ratio of fat to protein equal to about 0.19-0.20 (e.g., within a tolerance of +/−30%, 20%, 10%, 5%, or 1% of the mass ratio of fat to protein);
a mass ratio of dietary fiber to protein equal to about 0.81-1.36 (e.g., within a tolerance of +/−30%, 20%, 10%, 5%, or 1% of the mass ratio of dietary fiber to protein); and
any combination thereof.

135. The composition of clause 93:
wherein the at least a portion of grain is whole grain rice (e.g., brown rice) comprising gelatinized, hydrolyzed starch; and
wherein the at least a portion of grain comprises at least one mass ratio selected from the group consisting of:
a mass ratio of starch to protein equal to about 9.55-9.85 (e.g., within a tolerance of +/−30%, 20%, 10%, 5%, or 1% of the mass ratio of starch to protein);
a mass ratio of fat to protein equal to about 0.38-0.42 (e.g., within a tolerance of +/−30%, 20%, 10%, 5%, or 1% of the mass ratio of fat to protein);
a mass ratio of dietary fiber to protein equal to about 0.48-0.64 (e.g., within a tolerance of +/−30%, 20%, 10%, 5%, or 1% of the mass ratio of dietary fiber to protein); and
any combination thereof.

136. The composition of clause 93:
wherein the at least a portion of grain is whole grain rye comprising gelatinized, hydrolyzed starch; and
wherein the at least a portion of grain comprises at least one mass ratio selected from the group consisting of:
a mass ratio of starch to protein equal to about 5.78 (e.g., within a tolerance of +/−30%, 20%, 10%, 5%, or 1% of the mass ratio of starch to protein);
a mass ratio of fat to protein equal to about 0.16 (e.g., within a tolerance of +/−30%, 20%, 10%, 5%, or 1% of the mass ratio of fat to protein);
a mass ratio of dietary fiber to protein equal to about 1.46 (e.g., within a tolerance of +/−30%, 20%, 10%, 5%, or 1% of the mass ratio of dietary fiber to protein); and
any combination thereof.

137. The composition of clause 93:
wherein the at least a portion of grain is whole grain barley comprising gelatinized, hydrolyzed starch; and
wherein the at least a portion of grain comprises at least one mass ratio selected from the group consisting of:
a mass ratio of starch to protein equal to about 4.44 (e.g., within a tolerance of +/−30%, 20%, 10%, 5%, or 1% of the mass ratio of starch to protein);
a mass ratio of fat to protein equal to about 0.18 (e.g., within a tolerance of +/−30%, 20%, 10%, 5%, or 1% of the mass ratio of fat to protein);
a mass ratio of dietary fiber to protein equal to about 1.39 (e.g., within a tolerance of +/−30%, 20%, 10%, 5%, or 1% of the mass ratio of dietary fiber to protein); and
any combination thereof.

138. The composition of clause 93:
wherein the at least a portion of grain is whole grain sorghum comprising gelatinized, hydrolyzed starch; and
wherein the at least a portion of grain comprises at least one mass ratio selected from the group consisting of:
a mass ratio of starch to protein equal to about 5.92-8.08 (e.g., within a tolerance of +/−30%, 20%, 10%, 5%, or 1% of the mass ratio of starch to protein);
a mass ratio of fat to protein equal to about 0.33-0.40 (e.g., within a tolerance of +/−30%, 20%, 10%, 5%, or 1% of the mass ratio of fat to protein);
a mass ratio of dietary fiber to protein equal to about 0.63-0.78 (e.g., within a tolerance of +/−30%, 20%, 10%, 5%, or 1% of the mass ratio of dietary fiber to protein); and
any combination thereof.

139. A composition according to any method clause listed herein.

While this invention has been particularly shown and described with reference to preferred embodiments, it will be understood by those skilled in the art that various changes in form and detail can be made therein without departing from the spirit and scope of the invention. Accordingly, the invention can be embodied in other specific forms without departing from the spirit or essential characteristics thereof. The foregoing embodiments, therefore, are to be considered in all respects illustrative rather than limiting the invention described herein. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method comprising:
combining at least a portion of pulse that contains starch and an enzyme to form an enzyme-pulse starting mixture;
heating the enzyme-pulse starting mixture to between about 48.89° C. and about 93.33° C. to provide a heated pulse mixture; and
extruding the heated pulse mixture for about 0.5 to about 1.5 minutes to partially hydrolyze the starch and to gelatinize and cook the heated pulse mixture to provide a pulse product comprising gelatinized, partially hydrolyzed starch having the following characteristics:
an average molecular weight of the gelatinized, partially hydrolyzed starch is 0.60 to 0.07 times an original average molecular weight of the starch wherein the original average molecular weight of the starch is an average molecular weight of the starch before the gelatinization and the hydrolysis that provides the gelatinized, partially hydrolyzed starch; a mass ratio of starch to protein in the at least a portion of pulse is equal to an original mass ratio of starch to protein in the at least a portion of pulse within a tolerance of +/−10% wherein (i) the original mass ratio of the starch to protein is a mass ratio of starch to protein in the at least a portion of pulse before the gelatinization and the hydrolysis that provides the gelatinized, partially hydrolyzed starch, (ii) the mass ratio of starch to protein in the at least a portion of pulse is equal to the mass of starch divided by the mass of protein in the at least a portion of pulse, and (iii) the original mass ratio of starch to protein in the at least a portion of pulse is equal to the mass of starch divided by the mass of protein in the at least a portion of pulse before the gelatinization and the hydrolysis that provides the gelatinized, hydrolyzed starch.

2. The method of claim 1 further comprising combining sugar and at least one antioxidant with the pulse and enzyme and wherein the pulse is selected from the group consisting of peas, lentils, chickpeas, navy beans, black turtle beans, cranberry beans, kidney beans, pinto beans, small red beans, Dutch brown beans, pink beans, and any combination thereof.

3. The method of claim 2 further comprising combining maltodextrin with the pulse, enzyme, sugar, and at least one flour.

4. The method of claim 1:
wherein the at least a portion of pulse is pulse flour;
wherein the enzyme-pulse starting mixture comprises:
a mass ratio of sugar to pulse flour from about 0.03 to about 0.3;
a mass ratio of maltodextrin to pulse flour from about 0 to about 0.3; and
an effective amount of at least one antioxidant.

5. The method of claim 4 wherein the pulse flour is whole pulse flour.

6. The method of claim 4 wherein the pulse starting mixture comprises about 90 to about 95% by weight pulse flour.

7. The method of claim 1 further comprising pelletizing the pulse product to form a pelletized pulse product.

8. The method of claim 7 further comprising granulating the pelletized pulse product to form a granulated pulse product.

9. The method of claim 1 wherein the extruding occurs at a barrel temperature of about 60.00° C. to about 176.67° C.

10. The method of claim 1 wherein during the extruding the heated pulse mixture is heated to a temperature of about 100° C. to about 176.67° C.

11. The method of claim 1 wherein during the heating the enzyme-pulse starting mixture is heated to 60° C. to about 82.2° C.

12. The method of claim 1 further comprising adding the pulse product to a beverage to provide a product composition.

13. The method of claim 12 wherein the beverage is selected from the group consisting of fruit juices, dairy beverages, and carbonated soft drinks.

14. The method of claim 13 wherein the pulse product is added to the beverage to provide the product composition with 1 to 25% soluble fiber based on total weight of the product composition.

15. A product composition prepared in accordance with the method of claim 12, wherein the product composition is a beverage.

16. The method of claim 1 further comprising adding the pulse product to a mixture for a food product.

17. The method of claim 16 wherein the food product is selected from the group consisting of bars, cereals, puddings, smoothies, ice cream, cookies, and crackers.

18. The method of claim 1:
wherein the combining step comprises combining the at least a portion of pulse, at least a portion of grain, and the enzyme to form an enzyme-pulse-and-grain starting mixture;
wherein the heating step comprises heating the enzyme-pulse-and-grain starting mixture to between about 48.89° C. and about 93.33° C. to provide a heated pulse-and-grain mixture; and
wherein the extruding step comprises extruding the heated pulse-and-grain mixture for about 0.5 to about 1.5 minutes to partially hyrdolyze the starch and to gelatinize and cook the heated pulse-and-grain mixture to provide a pulse-and-grain product comprising gelatinized, partially hydrolyzed starch.

19. The method of claim 18 further comprising combining sugar and at least one antioxidant with the at least a portion of pulse, at least a portion of grain, and the enzyme;
wherein the pulse is selected from the group consisting of peas, lentils, chickpeas, navy beans, black turtle beans, cranberry beans, kidney beans, pinto beans, small red beans, Dutch brown beans, pink beans, and any combination thereof; and
wherein the grain is selected from the group consisting of wheat, oat, barley, corn, white rice, brown rice, barley, millet, sorghum, rye, triticale, teff, spelt, buckwheat, quinoa, amaranth, kaniwa, cockscomb, green groat, and any combination thereof.

20. The method of claim 1 wherein a temperature of the heated mixture during the extruding increases to deactivate the enzyme.

* * * * *